(12) United States Patent
Cicchetti et al.

(10) Patent No.: US 12,411,147 B2
(45) Date of Patent: *Sep. 9, 2025

(54) ERYTHROCYTE-DERIVED EXTRACELLULAR VESICLES AND PROTEINS ASSOCIATED WITH SUCH VESICLES AS BIOMARKERS FOR PARKINSON'S DISEASE

(71) Applicant: Université Laval, Québec (CA)

(72) Inventors: Francesca Cicchetti, Québec (CA); Eric Boilard, Québec (CA)

(73) Assignee: Université Laval, Québec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,992

(22) Filed: Sep. 5, 2023

(65) Prior Publication Data

US 2023/0408532 A1 Dec. 21, 2023

Related U.S. Application Data

(63) Continuation of application No. 16/484,073, filed as application No. PCT/CA2018/050150 on Feb. 9, 2018, now Pat. No. 11,662,352.

(60) Provisional application No. 62/457,350, filed on Feb. 10, 2017.

(51) Int. Cl.
| | |
|---|---|
| *G01N 33/68* | (2006.01) |
| *C12Q 1/32* | (2006.01) |
| *C12Q 1/34* | (2006.01) |
| *G01N 1/28* | (2006.01) |
| *G01N 33/50* | (2006.01) |
| *G01N 33/573* | (2006.01) |

(52) U.S. Cl.
CPC .......... *G01N 33/6896* (2013.01); *C12Q 1/32* (2013.01); *C12Q 1/34* (2013.01); *G01N 1/28* (2013.01); *G01N 33/5076* (2013.01); *G01N 33/573* (2013.01)

(58) Field of Classification Search
CPC .... G01N 33/6896; G01N 1/28; G01N 33/573; G01N 33/5076; C12Q 1/32; C12Q 1/34
See application file for complete search history.

(56) References Cited

U.S. PATENT DOCUMENTS

| | | | |
|---|---|---|---|
| 10,914,748 B2* | 2/2021 | Cicchetti | G01N 33/6896 |
| 11,662,352 B2* | 5/2023 | Cicchetti | G01N 1/28 435/7.1 |
| 2020/0271672 A1 | 8/2020 | Cicchetti et al. | |

FOREIGN PATENT DOCUMENTS

| | | |
|---|---|---|
| WO | 2018/145211 A1 | 8/2018 |

OTHER PUBLICATIONS

Coumans, F.A.W., et al., "Bulk immunoassays for analysis of extracellular vesicles," Platelets, vol. 28; No. 3; 242-248 (2017).
Cox, J. and Mann, M., "MaxQuant enables high peptide identification rates, individualized p.p.b.-range mass accuracies and proteome-wide protein quantification," Nature Biotechnology, vol. 26; No. 12; 1367-1372 (2008).
Cvjetkovic, A., et al., "Detailed Analysis of Protein Topology of Extracellular Vesicles—Evidence of Unconventional Membrane Protein Orientation," Scientific Reports, Article No. 36338; 12 pages (2016).
Final Office Action for U.S. Appl. No. 16/484,073, mailed Oct. 19, 2022.
Havlis, J. et al., "Fast-Response Proteomics by Accelerates In-Gel Digestion of Proteins," Anal. Chem, vol. 75; 1300-1306 (2003).
Lacroix, R. et al., "Impact of pre-analytical parameters on the measurement of circulating microparticles: towards standardization of protocol," Journal of Thrombosis and Haemostasis, vol. 10; 437-446 (2012).
International Search Report for International Application No. PCT/CA2018/050150, titled: "Erythrocyte-Derived Extracellular Vesicles And Proteins Associated With Such Vesicles As Biomarkers For Parkinson's Disease," mailed Apr. 23, 2018.
Lotvall, J. et al., "Minimal experimental requirements for definition of extracellular vesicles and their functions: a position statement from the International Society for Extracellular Vesicles," Journal of Extracellular Vesicles, vol. 3; 26913; 6 pages (2014).
Maere, S. et al., "BiNGO: A Cytoscape plugin to assess over-representation of Gene Ontology categories in Biological Networks," BioInformatics, vol. 21; No. 16; 3448-3449 (2005).
Mantel, P.-Y., et al., "Malaria infected erythrocyte-derived microvesicles mediate cellular communication within the parasite population and with the host immune system," Cell Host Microbe, vol. 13; No. 5; 521-534 (2013).
Martinez-Martin, P. et al., "Parkinson's disease severity levels and MDS-Unified Parkinson's Disease Rating Scale," Parkinsonism and Related Disorders, vol. 21; 50-54 (2015).
Matsumoto, J., et al., "Transmission of α-synuclein-containing erythrocyte-derived extracellular vesicles across the blood-brain barrier via adsorptive mediated transcytosis: another mechanism for initiation and progression of Parkinson's disease?," Acta Neuropathologica Communications, vol. 5; No. 71; 16 pages (2017).
Minetti, G. et al., "Differential sorting of tyrosine kinases and phosphotyrosine phosphatases acting on band 3 during vesiculation of human erythrocytes," Biohem J., vol. 377; 489-497 (2004).
Non-Final Office Action for U.S. Appl. No. 16/484,073, mailed May 12, 2022.
Notice of Allowance for U.S. Appl. No. 16/484,073, mailed Jan. 20, 2023.
Notification of Transmittal of International Preliminary Report on Patentability for International Application No. PCT/CA2018/050150, mailed Aug. 22, 2019.

(Continued)

*Primary Examiner* — Olga N Chernyshev
(74) *Attorney, Agent, or Firm* — Hamilton, Brook, Smith & Reynolds, P.C.

(57) ABSTRACT

The present description relates to methods for clinically assessing Parkinson's disease in a subject using protein biomarkers of erythrocyte-derived extracellular vesicles (EEV).

10 Claims, 17 Drawing Sheets

Specification includes a Sequence Listing.

(56) References Cited

OTHER PUBLICATIONS

Rousseau, M. et al., "Detection and Quantification of Microparticles from Different Cellular Lineages Using Flow Cytometry. Evaluation of the Impact of Secreted Phospholipase A2 on Microparticle Assessment," PLoS, vol. 10; No. 1; 0116812; 27 pages (2015).
Shevchenko, A. et al., "Mass Spectrometric Sequencing of Proteins from Silver-Stained Polyacrylamide Gels," Anal. Chem., vol. 68; 850-858 (1996).
Suzuki, R. et al., "Pvclust: an R package for assessing the uncertainty in hierarchical clustering," Bioinformatics, vol. 22; No. 12; 1540-1542 (2006).
Wither, M.J. et al., "Mass Spectrometry-Based Bottom-Up Proteomics: Sample Preparation, LC-MS/MS Analysis, and Database Query Strategies," Current Protocols in Protein Science, 16.4.1-16.4.20; 21 pages (2016).
Written Opinion for International Application No. PCT/CA2018/050150, titled: "Erythrocyte-Derived Extracellular Vesicles And Proteins Associated With Such Vesicles As Biomarkers For Parkinson's Disease," mailed Apr. 23, 2018.
Xu, R., et al., "Extracellular vesicle isolation and characterization: toward clinical application," The Journal of Clinical Investigation, vol. 126; No. 4; 1152-1162 (2016).

\* cited by examiner

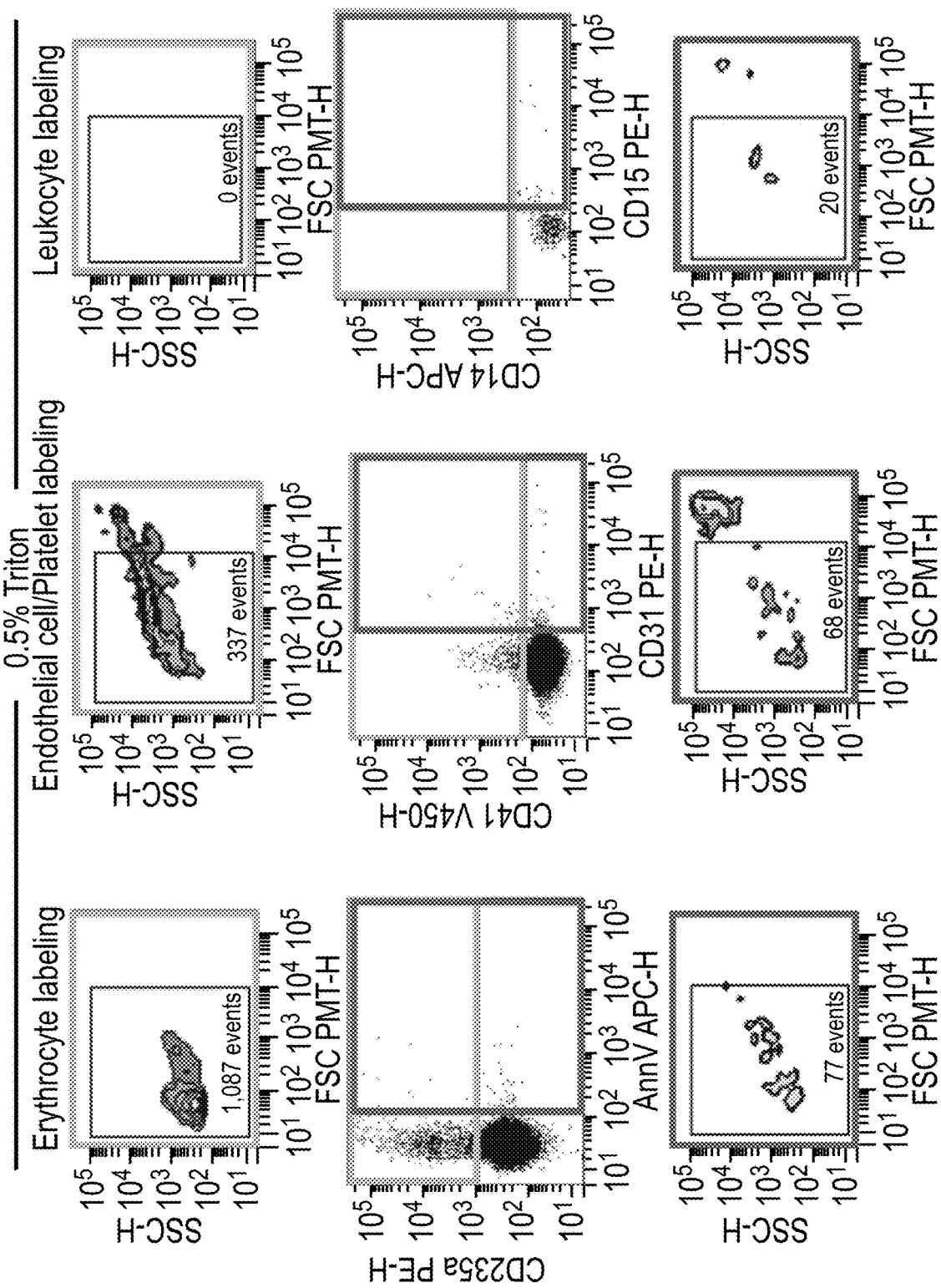

Fig. 4A

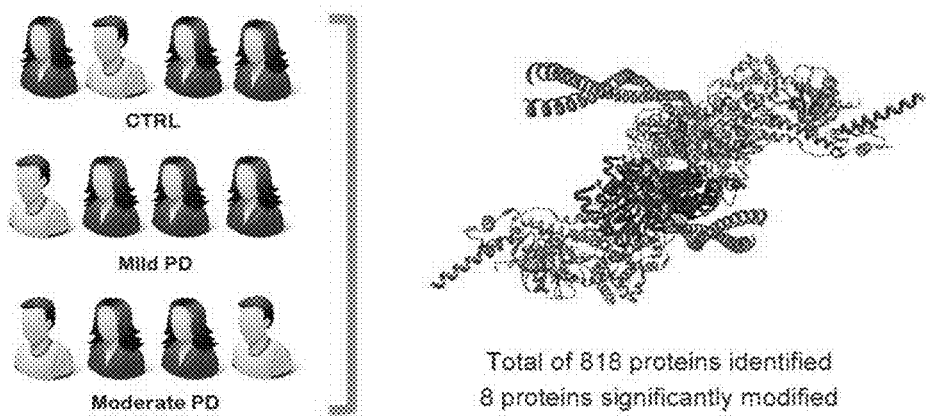

Total of 818 proteins identified
8 proteins significantly modified

Fig. 4B

| Groups | Protein biomarker | Uniprot ID | SEQ ID NO: | Corresponding gene name |
|---|---|---|---|---|
| I (Control) | Axin interactor, dorsalization-associated protein | Q96BJ3 | 1 | AIDA |
| | Alpha/beta hydrolase domain-containing protein 14B | Q96IU4 | 2 | ABHD14B |
| | Glutamine-dependent NAD(+) synthetase | E9PNF5 | 3 | NADSYN1 |
| II (mild PD) | Dihydropteridine reductase | P09417 | 4 | QDPR |
| | Alcohol dehydrogenase [NADP(+)] | P14550 | 5 | AKR1A1 |
| | CB1 cannabinoid receptor-interacting protein 1 | B8ZZB8 | 6 | CNRIP1 |
| III (moderate PD) | Ubiquitin carboxyl-terminal hydrolase 24 | Q9UPU5 | 7 | USP24 |
| | ATP synthase subunit alpha, mitochondrial | K7EQH4 | 8 | ATP5A1 |

```
SEQUENCE LISTING

Sequence total quantity: 8
SEQ ID NO: 1         moltype = AA  length = 306
FEATURE              Location/Qualifiers
REGION               1..306
                     note = MISC_FEATURE - AIDA
source               1..306
                     mol_type = protein
                     organism = Homo sapiens
SEQUENCE: 1
MSEVTRSLLQ RWGASFRRGA DFDSWGQLVE AIDEYQILAR HLQKEAQAQH NNSEFTEEQK    60
KTIGKIATCL ELRSAALQST QSQEEFKLED LKKLEPILKN ILTYNKEFPF DVQPVPLRRI   120
LAPGEEENLE FEEDEEEGGA GAGSPDSFPA RVPGTLLPRL PSEPGMTLLT IRIEKIGLKD   180
AGQCIDPYIT VSVKDLNGID LTPVQDTPVA SRKEDTYVHF NVDIELQKHV EKLTKGAAIF   240
FEFKHYKPKK RFTSTKCFAF MEMDEIKPGP IVIELYKKPT DFKRKKLQLL TKKPLYLHLH   300
QTLHKE                                                             306

SEQ ID NO: 2         moltype = AA  length = 210
FEATURE              Location/Qualifiers
REGION               1..210
                     note = MISC_FEATURE - ABHD14B
source               1..210
                     mol_type = protein
                     organism = Homo sapiens
SEQUENCE: 2
MAASVEQREG TIQVQGQALF FREALPGSGQ ARFSVLLLHG IRFSSETWQN LGTLHRLAQA    60
GYRAVAIDLP GLGHSKEAAA PAPIGELAPG SFLAAVVDAL ELGPPVVISP SLSGMYSLPF   120
LTAPGSQLPG FVPVAPICTD KINAANYASV KTPALIVYGD QDPMGQTSFE HLKQLPNHRV   180
LIMKGAGHPC YLDKPEEWHT GLLDFLQGLQ                                   210

SEQ ID NO: 3         moltype = AA  length = 446
FEATURE              Location/Qualifiers
REGION               1..446
```

```
                        note = MISC_FEATURE - NADSYN1
source                  1..446
                        mol_type = protein
                        organism = Homo sapiens
SEQUENCE: 3
MGISGQEVLT ATLDLEDVRS YRAEISSRNL AASRASPYPR VKVDFALSCH EDLLAPISEP    60
IEWKYHSPEE EISLGPACWL WDFLRRSQQA GFLLPLSGGV DSAATACLIY SMCCQVCEAV   120
RSGNEEVLAD VRTIVNQISY TPQDPRDLCG RILTTCYMAS KNSSQETCTR ARELAQQIGS   180
HHISLNIDPA VKAVMGIFSL VTGKSPLFAA HGGSSRENLA LQNVQARIRM VLAYLFAQLS   240
LWSRGVHGGL LVLGSANVDE SLLGYLTKYD CSSADINPIG GISKTDLRAF VQFCIQRFQL   300
PALQSILLAP ATAELEPLAD GQVSQTDEED MGMTYAELSV YGKLRKVAKM GPYSMFCKLL   360
GMWRHICTPR QVADKVKRFF SKYSMNRHKM TTLTPAYHAE NYSPEDNRFD LRPFLYNTSW   420
PWQFRCIENQ VLQLERAEPQ SLDGVD                                        446

SEQ ID NO: 4            moltype = AA   length = 213
FEATURE                 Location/Qualifiers
REGION                  1..213
                        note = MISC_FEATURE - QDPR
source                  1..213
                        mol_type = protein
                        organism = Homo sapiens
SEQUENCE: 4
MAAAAAAGEA RRVLVYGGRG ALGSRCVQAF RARNWVTAEV GKLLGEEKVD AILCVAGGWA    60
GGNAKSKSLF KNCDLMWKQS IWTSTISSHL ATKHLKEGGL LTLAGAKAAL DGTPGMIGYG   120
MAKGAVHQLC QSLAGKNSGM PPGAAAIAVL PVTLDTPMNR KSMPEADFSS WTPLEFLVET   180
FHDWITGKNR PSSGSLIQVV TTEGRTELTP AYF                                213

SEQ ID NO: 5            moltype = AA   length = 325
FEATURE                 Location/Qualifiers
REGION                  1..325
                        note = MISC_FEATURE - AKR1A1
source                  1..325
                        mol_type = protein
                        organism = Homo sapiens
SEQUENCE: 5
MAASCVLLHT GQKMPLIGLG TWKSEPGQVK AAVKYALSVG YRHIDCAAIY GNEPEIGEAL    60
KEDVGPGKAV PREELFVTSK LWNTKHHPED VEPALRKTLA DLQLEYLDLY LMHWPYAFER   120
GDNPFPKNAD GTICYDSTHY KETWKALEAL VAKGLVQALG LSNFNSRQID DILSVASVRP   180
AVLQVECHPY LAQNELIAHC QARGLEVTAY SPLGSSDRAW RDPDEPVLLE EPVVLALAEK   240
YGRSPAQILL RWQVQRKVIC IPKSITPSRI LQNIKVFDFT FSPEEMKQLN ALNKNWRYIV   300
PMLTVDGKRV PRDAGHPLYP FNDPY                                         325

SEQ ID NO: 6            moltype = AA   length = 137
FEATURE                 Location/Qualifiers
REGION                  1..137
                        note = MISC_FEATURE - CNRIP1
source                  1..137
                        mol_type = protein
                        organism = Homo sapiens
SEQUENCE: 6
MGDLPGLVRL SIALRIQPND GPVFYKVDGQ RFGQNRTIKL LTGSSYKVEV KIKPSTLQVE    60
NISIGGVLVP LELKSKEPDG DRVVYTGTYD TEGVTPTKSG ERQPIQITMP VRLACGYRSM   120
VPWKMETTEK KTITISL                                                  137

SEQ ID NO: 7            moltype = AA   length = 2620
FEATURE                 Location/Qualifiers
REGION                  1..2620
                        note = MISC_FEATURE - USP24
source                  1..2620
                        mol_type = protein
                        organism = Homo sapiens
SEQUENCE: 7
MESEEEQHMT TLLCMGFSDP ATIRKALRLA KNDINEAVAL LTNERPGLDY GGYEPMDSGG    60
GPSPGPGGGP RGDGGGDGGG GGPSRGGSTG GGGGFDPPPA YHEVVDAEKN DENGNCSGEG   120
IEFPTTNLYE LESRVLTDHW SIPYKREESL GKCLLASTYL ARLGLSESDE NCRRFMDRCM   180
PEAFKKLLTS SAVHKWGTEI HEGIYNMLML LIELVAERIK QDPIPTGLLG VLTMAFNPDN   240
EYHFKNRMKV SQRNWAEVFG EGNMFAVSPV STFQKEPHGW VVDLVNKFGE LGGFAAIQAK   300
LHSEDIELGA VSALIQPLGV CAEYLNSSVV QPMLDPVILT TIQDVRSVEE KDLKDKRLVS   360
IPELLSAVKL LCMRFQPDLV TIVDDLRLDI LLRMLKSPHF SAKMNSLKEV TKLIEDSTLS   420
KSVKNAIDTD RLLDWLVENS VLSIALEGNI DQAQYCDRIK GIIELLGSKL SLDELTKIWK   480
IQSGQSSTVI ENIHTIIAAA AVKFNSDQLN HLFVLIQKSW ETESDRVQRK LLSLIGRIGR   540
EARFETTSGK VLDVLWELAH LPTLPSSLIQ QALEEHLTIL SDAYVKEAI KRSYIIKCIE    600
DIKRPGEWSG LEKNKKDGFK SSQLNNPQFV WVPALRQLH EITRSFIKQT YQKQDKSIIQ    660
DLKKNFEIVK LVTGSLIACH RLAAAVAGPG GLSGSTLVDG RYTYREYLEA HLKFLAFFLQ   720
EATLYLGWNR AKEIWECLVT GQDVCELDRE MCFEWFTKGQ HDLESDVQQQ LFKEKILKLE   780
SYEITMNGFN LFKTFFENVN LCDHRLKRQG AQLYVEKLEL IGMDFIWKIA MESPDEEIAN   840
EAIQLIINYS YINLNPRLKK DSVSLHKKFI ADCYTRLEAA SSALGGPTLT HAVTRATKML   900
TATAMPTVAT SVQQSPYRSTK LVIIERLLLL AERYVITIED FYSVPRTILP HGASFHGHLL   960
TLNVTYESTK DTFTVEAHSN ETIGSVRWKI AKQLCSPVDN IQIFTNDSLL TVNKDQKLLH  1020
```

```
QLGFSDEQIL TVKTSGSGTP SGSSADSSTS SSSSSSGVFS SSYAMEQEKS LPGVVMALVC  1080
NVFDMLYQLA NLEEPRITLR VRKLLLLIPT DPAIQEALDQ LDSLGRKKTL LSESSSQSSK  1140
SPSLSSKQQH QPSASSILES LFRSFAPGMS TFRVLYNLEV LSSKLMPTAD DDMARSCAKS  1200
FCENFLKAGG LSLVVNVMQR DSIPSEVDYE TRQGVYSICL QLARFLLVGQ TMPTLLDEDL  1260
TKDGIEALSS RPFRNVSRQT SRQMSLCGTP EKSSYRQLSV SDRSSIRVEE IIPAARVAIQ  1320
TMEVSDFTST VACFMRLSWA AAAGRLDLVG SSQPIKESNS LCPAGIRNRL SSSGSNCSSG  1380
SEGEPVALHA GICVRQQSVS TKDSLIAGEA LSLLVTCLQL RSQQLASFYN LPCVADFIID  1440
ILLGSPSAEI RRVACDQLYT LSQTDTSAHP DVQKPNQFLL GVILTAQLPL WSPTSIMRGV  1500
NQRLLSQCME YFDLRCQLLD DLTTSEMEQL RISPATMLED EITWLDNFEP NRTAECETSE  1560
ADNILLAGHL RLIKTLLSLC GAEKEMLGSS LIKPLLDDFL FRASRIILNS HSPAGSAAIS  1620
QQDFHPKCST ANSRLAAYEV LVMLADSSPS NLQIIIKELL SMHHQPDPAL TKEFDYLPPV  1680
DSRSSSGFVG LRNGGATCYM NAVFQQLYMQ PGLPESLLSV DDDTDNPDDS VFYQVQSLFG  1740
HLMESKLQYY VPENFWKIFK MWNKELYVRE QQDAYEFFTS LIDQMDEYLK KMGRDQIFKN  1800
TFQGIYSDQK ICKDCPHRYE REEAFMALNL GVTSCQSLEI SLDQFVRGEV LEGSNAYYCE  1860
KCKEKRITVK RTCIKSLPSV LVIHLMRFGF DWESGRSIKY DEQIRFPWML NMEPYTVSGM  1920
ARQDSSSEVG ENGRSVDQGG GGSPRKKVAL TENYELVGVI VHSGQAHAGH YYSFIKDRRG  1980
CGKGKWYKFN DTVIEEFDLN DETLEYECFG GEYRPKVYDQ TNPYTDVRRR YWNAYMLFYQ  2040
RVSDQNSPVL PKKSRVSVVR QEAEDLSLSA PSSPEISPQS SPRPHRPNND RLSILTKLVK  2100
KGEKKGLFVE KMPARIYQMV RDENLKFMKN RDVYSSDYFS FVLSLASLNA TKLKHPYYPC  2160
MAKVSLQLAI QFLFQTYLRT KKKLRVDTEE WIATIEALLS KSFDACQWLV EYFISSEGRE  2220
LIKIFLLECN VREVRVAVAT ILEKTLDSAL FYQDKLKSLH QLLEVLLALL DKDVPENCKN  2280
CAQYFFLFNT FVQKQGIRAG DLLLRHSALR HMISFLLGAS RQNNQIRRWS SAQAREFGNL  2340
HNTVALLVLH SDVSSQRNVA PGIFKQRPPI SIAPSSPLLP LHEEVEALLF MSEGKPYLLE  2400
VMFALRELTG SLLALIEMVV YCCFCNEHFS FTMLHFIKNQ LETAPPHELK NTFQLLHEIL  2460
VIEDPIQVER VKFVFETENG LLALMHHSNH VDSSRCYQCV KFLVTLAQKC PAAKEYFKEN  2520
SHHWSWAVQW LQKKMSEHYW TPQSNVSNET STGKTFQRTI SAQDTLAYAT ALLNEKEQSG  2580
SSNGSESSPA NENGDRHLQQ GSESPMMIGE LRSDLDDVDP                       2620

SEQ ID NO: 8          moltype = AA  length = 221
FEATURE               Location/Qualifiers
REGION                1..221
                      note = MISC_FEATURE - ATP5A1
source                1..221
                      mol_type = protein
                      organism = Homo sapiens
SEQUENCE: 8
MLSVRVAAAV VRALPRRAGL VSRNALGSSF IAARNFHASN THLQKTGTAE MSSILEERIL  60
GADTSVDLEE TGRVLSIGDG IARVHGLRNV QAEEMVEFSS GLKGMSLNLE PDNVGVVVFG  120
NDKLIKEGDI VKRTGAIVDV PVGEELLGRV VDALGNAIDG KGPIGSKTRR RVGLKAPGII  180
PRISVREPMQ TGIKAVDSLV PIGRGQRELI IGDRQTGNTG W                     221
```

ERYTHROCYTE-DERIVED EXTRACELLULAR VESICLES AND PROTEINS ASSOCIATED WITH SUCH VESICLES AS BIOMARKERS FOR PARKINSON'S DISEASE

RELATED APPLICATIONS

This application is a Continuation of U.S. patent application Ser. No. 16/484,073, which is the U.S. National Stage of International Application No. PCT/CA2018/050150, filed Feb. 9, 2018, which designates the U.S., published in English, and claims the benefit of U.S. Provisional Application No. 62/457,350, filed Feb. 10, 2017. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:
   a) File name: 54931003003_Sequence_Listing.xml; created Apr. 25, 2023, 15,256 Bytes in size. The computer readable form is incorporated herein by reference.

| SEQ ID NO: | Protein sequence of: | Uniprot ID |
|---|---|---|
| 1 | Axin interactor, dorsalization-associated protein | Q96BJ3 |
| 2 | Alpha/beta hydrolase domain-containing protein 14B | Q96IU4 |
| 3 | Glutamine-dependent NAD(+) synthetase | E9PNF5 |
| 4 | Dihydropteridine reductase | P09417 |
| 5 | Alcohol dehydrogenase [NADP(+)] | P14550 |
| 6 | CB1 cannabinoid receptor-interacting protein 1 | B8ZZB8 |
| 7 | Ubiquitin carboxyl-terminal hydrolase 24 | Q9UPU5 |
| 8 | ATP synthase subunit alpha, mitochondrial | K7EQH4 |

BACKGROUND

Parkinson's disease (PD) is one of the most common neurodegenerative disorders affecting millions of people worldwide. Definite diagnosis for PD can only be made postmortem, for instance, by the characteristic accumulation of the protein alpha-synuclein into Lewy body inclusions observed within neurons. Currently, the diagnosis of PD is based on fitting observed symptoms and their severity into clinical rating scales such as the Unified Parkinson's Disease Rating Scale (UPDRS) or the Hoehn & Yahr scale. Current clinical assessments are subjective, however, and would benefit from improved methods of clinically assessing PD, particularly at early stages of the disease when therapeutic options are likely to be most efficient.

SUMMARY

The present description relates to Parkinson's disease. More particularly, the present description relates to extracellular vesicles originating from erythrocytes, and protein biomarkers associated erythrocyte-derived extracellular vesicles, for use in clinically assessing Parkinson's disease in a subject.

The present description relates to the proteomic analysis of erythrocyte-derived extracellular vesicles (EEV) from healthy control subjects, subjects with mild Parkinson's disease, and subjects with moderate Parkinson's disease, as well as the identification of protein biomarkers for which expression within EEV was found to be significantly modified therebetween. Accordingly, the present description generally relates to methods of clinically assessing Parkinson's disease based on the detection and/or quantification of the expression level of one or more protein biomarker(s) within EEV.

In some aspects, the present description may relate to one or more of the following items:

1. An in vitro method for clinically assessing Parkinson's disease, the method comprising obtaining a preparation of isolated erythrocyte-derived extracellular vesicles (EEV) from a blood sample of a subject having or suspected of having Parkinson's disease; and determining the expression level(s) of one or more protein biomarker(s) in the preparation of isolated EEV, wherein the one or more protein biomarker(s) comprises: (i) Alpha/beta hydrolase domain-containing protein 14B, if the subject has or is suspected of having mild or moderate Parkinson's disease; (ii) Alcohol dehydrogenase [NADP(+)], if the subject has or is suspected of having mild Parkinson's disease; (iii) ATP synthase subunit alpha, mitochondrial, if the subject has or is suspected of having moderate Parkinson's disease; or (iv) any combination of (i) to (iii), wherein the expression level of one or more of the protein biomarker(s) is indicative of, or correlates with, the subject's Parkinson's disease state.
2. An in vitro method for clinically assessing Parkinson's disease, the method comprising: obtaining a preparation of isolated erythrocyte-derived extracellular vesicles (EEV) from a blood sample of a subject having or suspected of having Parkinson's disease; and determining the expression level(s) of one or more protein biomarker(s) in the preparation of isolated EEV, wherein the expression level of one or more of the protein biomarker(s) is indicative of, or correlates with, the subject's Parkinson's disease state.
3. The method of item 2, wherein the one or more protein biomarker(s) comprises at least one of: (a) Axin interactor, dorsalization-associated protein; (b) Alpha/beta hydrolase domain-containing protein 14B; (c) Glutamine-dependent NAD(+) synthetase; (d) Dihydropteridine reductase; (e) Alcohol dehydrogenase [NADP(+)]; (f) CB1 cannabinoid receptor-interacting protein 1; (g) Ubiquitin carboxyl-terminal hydrolase 24; and (h) ATP synthase subunit alpha, mitochondrial.
4. The method of item 3, wherein the one or more protein biomarkers comprises at least two of (a) to (h).
5. The method of item 3, wherein the one or more protein biomarkers comprises at least three of (a) to (h).
6. The method of item 3, wherein the one or more protein biomarkers comprises at least four of (a) to (h).
7. The method of item 3, wherein the one or more protein biomarkers comprises at least five of (a) to (h).
8. The method of item 3, wherein the one or more protein biomarkers comprises at least six of (a) to (h).
9. The method of item 3, wherein the one or more protein biomarkers comprises at least seven of (a) to (h).
10. The method of any one of items 2 to 9, wherein the one or more protein biomarkers comprises (a).
11. The method of any one of items 2 to 10, wherein the one or more protein biomarkers comprises (b).
12. The method of any one of items 2 to 11, wherein the one or more protein biomarkers comprises (c).

13. The method of any one of items 2 to 12, wherein the one or more protein biomarkers comprises (d).
14. The method of any one of items 2 to 13, wherein the one or more protein biomarkers comprises (e).
15. The method of any one of items 2 to 14, wherein the one or more protein biomarkers comprises (f).
16. The method of any one of items 2 to 15, wherein the one or more protein biomarkers comprises (g).
17. The method of any one of items 2 to 16, wherein the one or more protein biomarkers comprises (h).
18. The method of any one of items 2 to 17, further comprising determining the expression level(s) of one or more of the EEV protein(s) listed in Table 4, wherein the one or more EEV protein(s) does not comprise (a) to (h).
19. The method of any one of items 2 to 18, further comprising normalizing the expression level(s) of the one or more protein biomarker(s) to one or more of the EEV protein(s) as defined in item 18.
20. The method of any one of items 1 to 19, wherein the preparation of isolated EEV is obtained after inducing the calcium-dependent production of EEV from activated erythrocytes in the blood sample of the subject.
21. The method of any one of items 1 to 20, wherein the preparation of isolated erythrocyte-derived extracellular vesicles (EEV) is obtained by separating the EEV by flow cytometry, differential centrifugation, nanomembrane ultrafiltration, immunoabsorbent capture, size-exclusion chromatography, ultracentrifugation, magnetic activated cell sorting (MACS), nanoparticle tracking analysis, light scattering, electrophoretic light scattering, dynamic light scattering, electron microscopy, or any combination thereof.
22. The method of any one of items 1 to 21, wherein the EEV are CD235a+ extracellular vesicles.
23. The method of any one of items 1 to 22, wherein the EEV are TSG101+, Rabs+, CD9+, CD63+, CD81+, or any combination thereof.
24. The method of any one of items 1 to 23, wherein the EEV are between about 20 nm and about 1000 nm in diameter.
25. The method of any one of items 1 to 24, wherein said EEV are greater than about 100 nm in diameter.
26. The method of any one of items 1 to 25, further comprising removing hemoglobin from the preparation of isolated EEV prior to determining the expression level(s) of the one or more protein biomarker(s).
27. The method of any one of items 1 to 26, wherein determining the expression level(s) of one or more of the protein biomarker(s) in the preparation of isolated EEV comprises contacting the protein biomarker with an antibody directed against the protein biomarker.
28. The method of any one of items 1 to 27, wherein determining the expression level(s) of one or more of the protein biomarker(s) in the preparation of isolated EEV comprises mass spectrometry.
29. The method of item 28, wherein determining the expression level(s) of one or more of the protein biomarker(s) in the preparation of isolated EEV comprises nano liquid chromatography tandem mass spectrometry (nanoLC-MS/MS).
30. The method of any one of items 1 to 29, wherein clinically assessing Parkinson's disease comprises diagnosing Parkinson's disease.
31. The method of any one of items 1 to 30, wherein clinically assessing Parkinson's disease in the subject comprises staging Parkinson's disease.
32. The method of any one of items 1 to 31, wherein clinically assessing Parkinson's disease comprises monitoring the progression of Parkinson's disease.
33. The method of any one of items 1 to 32, wherein clinically assessing Parkinson's disease comprises monitoring the effectiveness of treatment of a Parkinson's disease subject.
34. The method of item 32 or 33, comprising determining the expression level(s) of one or more of the protein biomarker(s) in a preparation of isolated EEV from a further blood sample of the subject obtained at a later point of time.
35. A method for analyzing proteins of erythrocyte-derived extracellular vesicles (EEV), the method comprising: (i) isolating erythrocyte-derived extracellular vesicles (EEV) from a blood sample of a subject and forming an EEV preparation therefrom; (ii) extracting proteins from the EEV preparation; (iii) removing hemoglobin from the EEV preparation to obtain a hemoglobin-free EEV preparation; and (iv) detecting EEV proteins present in the hemoglobin-free EEV preparation.
36. The method of item 35, wherein: step (iii) comprises removing a hemoglobin-containing fraction of proteins from the EEV preparation to obtain a hemoglobin-depleted EEV preparation and a hemoglobin-rich fraction; and step (iv) comprises detecting EEV proteins present in the hemoglobin-free EEV preparation and EEV proteins present in the hemoglobin-rich fraction.
37. The method of item 35 or 36, wherein the EEV proteins detected comprise the protein biomarkers as defined in any one of items 3 to 17.
38. The method of any one of items 35 to 37, wherein the preparation of isolated EEV is obtained after inducing the calcium-dependent production of EEV from activated erythrocytes in the blood sample of the subject.
39. The method of any one of items 35 to 38, wherein the preparation of isolated erythrocyte-derived extracellular vesicles (EEV) is obtained as defined in item 21.
40. The method of any one of items 35 to 39, wherein the EEV are as defined in any one of items 21 to 24.
41. The method of any one of items 35 to 40, wherein the EEV proteins are detected as defined in any one of items 26 to 28.
42. Use of one or more erythrocyte-derived extracellular vesicle (EEV) protein biomarker(s) as defined in any one of items 3 to 17 for clinically assessing Parkinson's disease in a subject.
43. The use of item 42, wherein the clinical assessment is as defined in any one of items 30 to 33.
44. A method of treating a subject with Parkinson's disease, the method comprising: (i) clinically assessing the subject according to the method of any one of items 1 to 41; and (ii) beginning or modifying the subject's Parkinson's disease treatment based on the clinical assessment in (i).

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an", when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A-1F. Optimization of EV detection: controls for flow cytometry. FIG. 1A: To properly set the EV gate, fluorescent silica beads of 100 nm (Red), 500 nm (Blue) and 1000 nm (Yellow) were acquired on a flow cytometer Canto II modified with a FSC-PMT small particles option. The EV gate was used throughout the experiments. FIG. 1B: Serial dilutions (1, 2, 4 and 10) of erythrocyte-derived EV (EEV) to confirm the linearity of the quantification. FIG. 1C: FSC-PMT/SSC gates of platelet-free plasma (PFP) stained with annexin V and respective fluorochrome-conjugated antibodies directed against erythrocyte (CD235a+), endothelial (CD31+/CD41−)/platelets (CD41+) and leukocytes (CD14+CD45+, monocytes; CD15+CD45+, granulocytes)-derived EV. Controls for EV labeling. FIG. 1D: Treatment with the ion chelator EDTA inhibited the binding of annexin V to phosphatidylserine. FIG. 1E: Minimal background was observed using antibodies in absence of PFP. This background was subtracted from all subsequent EV quantifications. FIG. 1F: EV sensitivity to 0.5% Triton™ was assessed. Abbreviations: AnnV, annexin V; FSC PMT-H, forward scatter photomultiplier; PBS, phosphate buffered saline; PFP, platelet free plasma; SSC-H, side scatter.

FIG. 2A shows the correlations between the number of erythrocyte-derived extracellular vesicles (EEV; expressed as CD235a+ EV/total number of erythrocytes) and the Unified Parkinson's Disease Rating Scale (UPDRS) of subjects (n=20). Robust correlations between the number of EEV/total number of erythrocytes and UPDRS scores (PD, n=20), displayed a clear split between mild and moderate patients, supporting the potential of EEV as a biomarker for disease state. Additional information on five patients (identified as 1-5) derived from each correlation is provided (number of EEV/total number of erythrocytes and levodopa dose equivalent) to illustrate that levodopa dosing cannot account for differences in EEV counts. Note that patient no. 5, which falls outside the confidence boundary, is the only patient on a regimen of anti-inflammatory drugs to manage arthritis. FIG. 2B shows the results of a similar analysis as in FIG. 2A, but performed on Huntington's disease subjects (n=42) using the Unified Huntington's Disease Rating Scale (UHDRS). The numbers of EEV are expressed as CD235a+ EV/total number of erythrocytes. No statistically significant correlations were found between the number of EEV/total number of erythrocytes and UHDRS scores. This argues in favor of EEV being a specific biomarker of PD. Distributions were determined using unpaired t-test with Welch's correction (PD) or one-way ANOVA (HD). Correlations were determined using Pearson's correlation, *p<0.05. Abbreviations: CD235a, glycophorin A; CTRL, Controls; EEV, erythrocyte-derived extracellular vesicle; EV, extracellular vesicle; HD, Huntington's disease; LEDD, Levodopa equivalent daily dose; PD, Parkinson's disease; Pre-HD, Pre-manifest; UHDRS, Unified Huntington's Disease Rating Scale; UPDRS, Unified Parkinson's Disease Rating Scale.

FIG. 3A: Representative scanning electron microscopy observations of resting and activated erythrocytes (treated with calcium ionophore A23187 to generate EEV) in both PD patients and healthy sex- and age-matched CTRL. Scale bar: 2 μm. FIG. 3B: Representative transmission electron microscopy images of immunogold labeling for α-Syn and α-Syn pS129 in activated erythrocytes and EEV (some examples delineated by dotted lines). Arrowheads point to positive immunolabeling for either α-Syn or α-Syn pS129. Scale bar: 100 nm.

FIGS. 4A-4D. Specific protein signature of EEV in PD patients. FIG. 4A: NanoLC-MS/MS Label-free analysis of EEV in PD patients and healthy age-matched CTRL (PD, n=4; CTRL, n=4) revealed a total of 818 proteins, with 8 of which the expression was significantly modified as a function of PD states. FIG. 4B: The 8 differentially expressed proteins are referenced according to the gene to which they are associated, and further separated into 3 groups in relation to their expression variations in comparison to CTRL (Group I), mild PD (Group II) or moderate PD (Group III).

FIG. 4C: Normalized expression (intensity) of the proteins associated with the Group I genes AIDA, ABHD14B, and NADSYN1; the Group II genes QDPR, AKR1A1, and CNRIP1; and the Group III genes USP24 and ATP5A1. FIG. 4D: Heatmap establishing correlations between disease states and the abundance of the variable proteins. Cold (C) and hot (H) colors represent low and high correlation levels, respectively. The AU p value is indicated for each node. Protein modulation was determined by unpaired t-tests with Welch's correction using the criteria of a p value under 0.05 and a minimum of 2-fold change between groups, *p<0.05,

**p<0.01. Abbreviations: AU, Approximately Unbiased; CTRL Control; PD, Parkinson's disease.

Figure 5A:
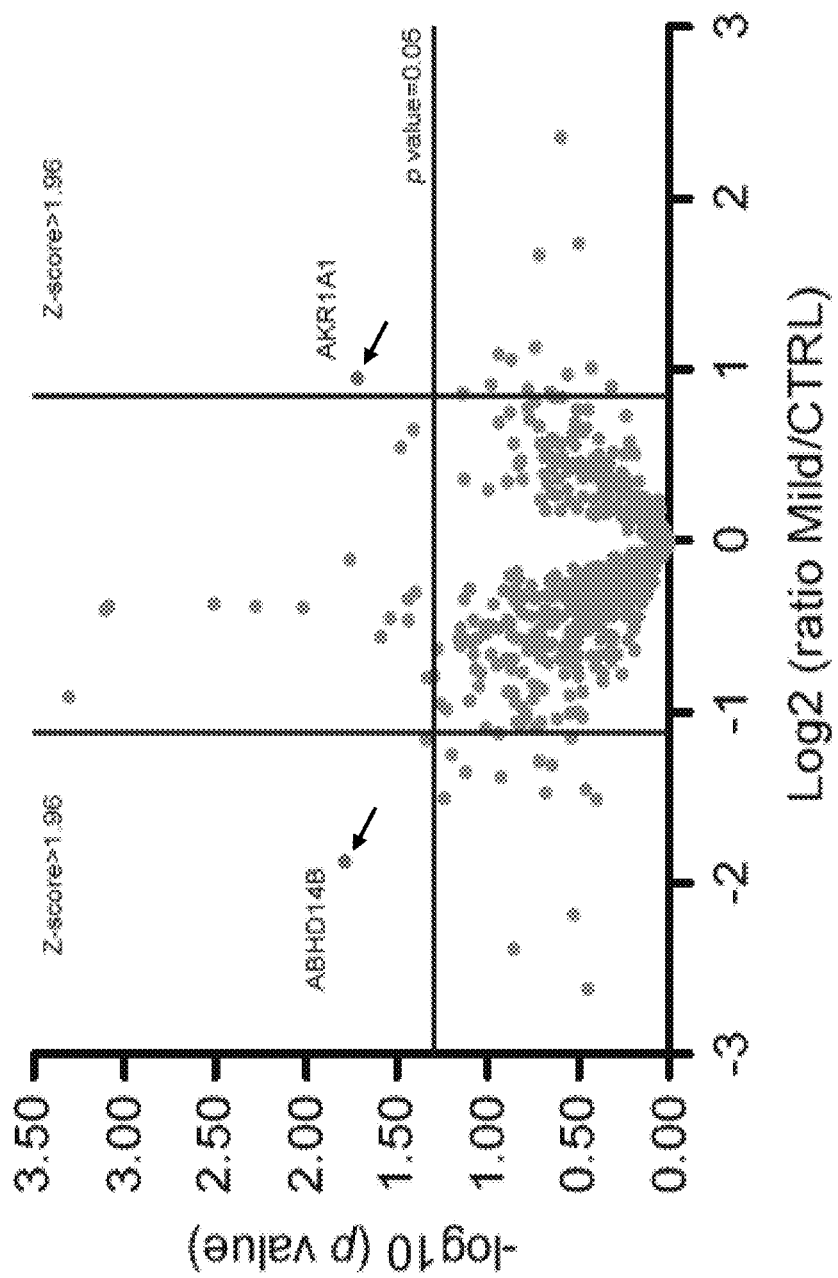
Figure 5B:
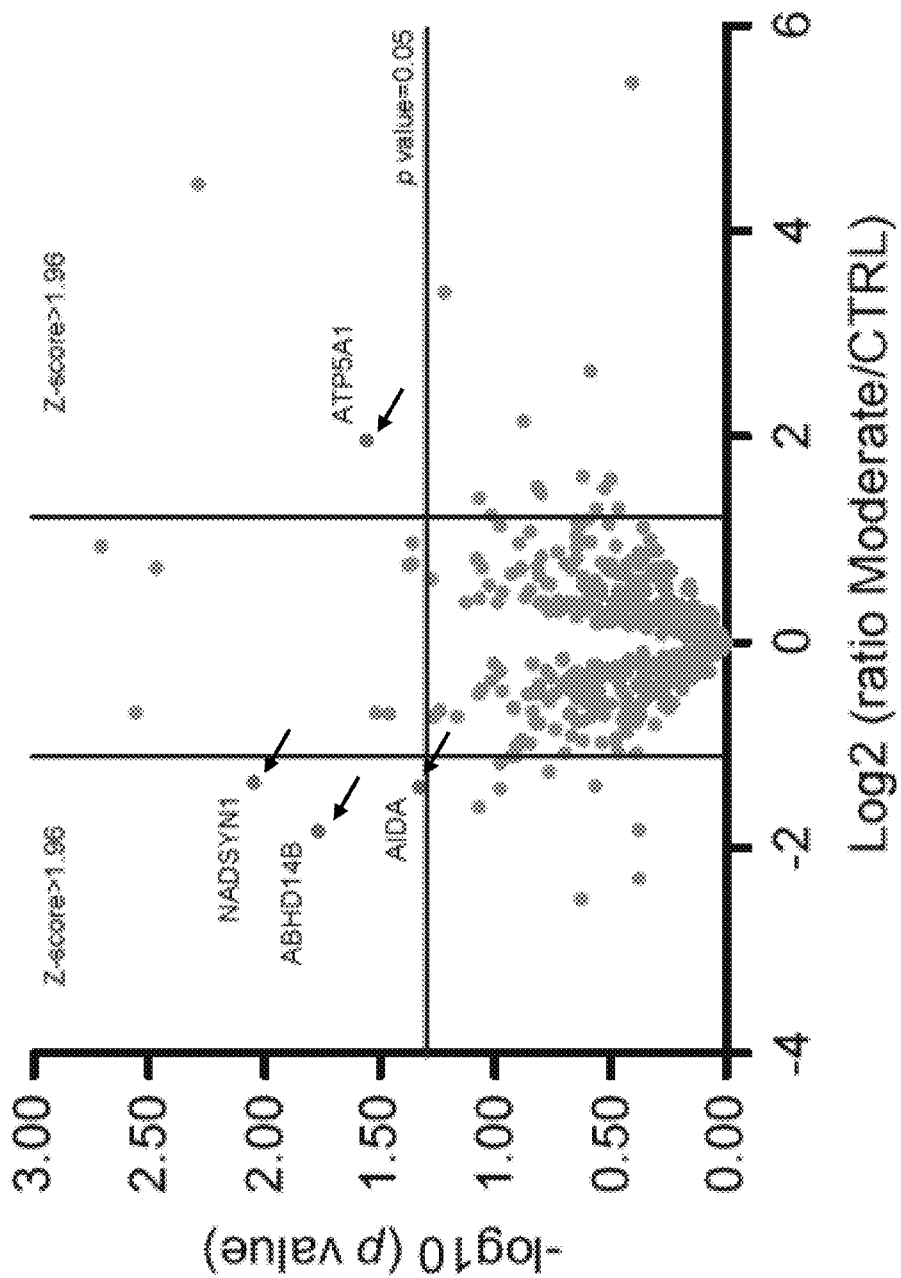
Figure 5C:
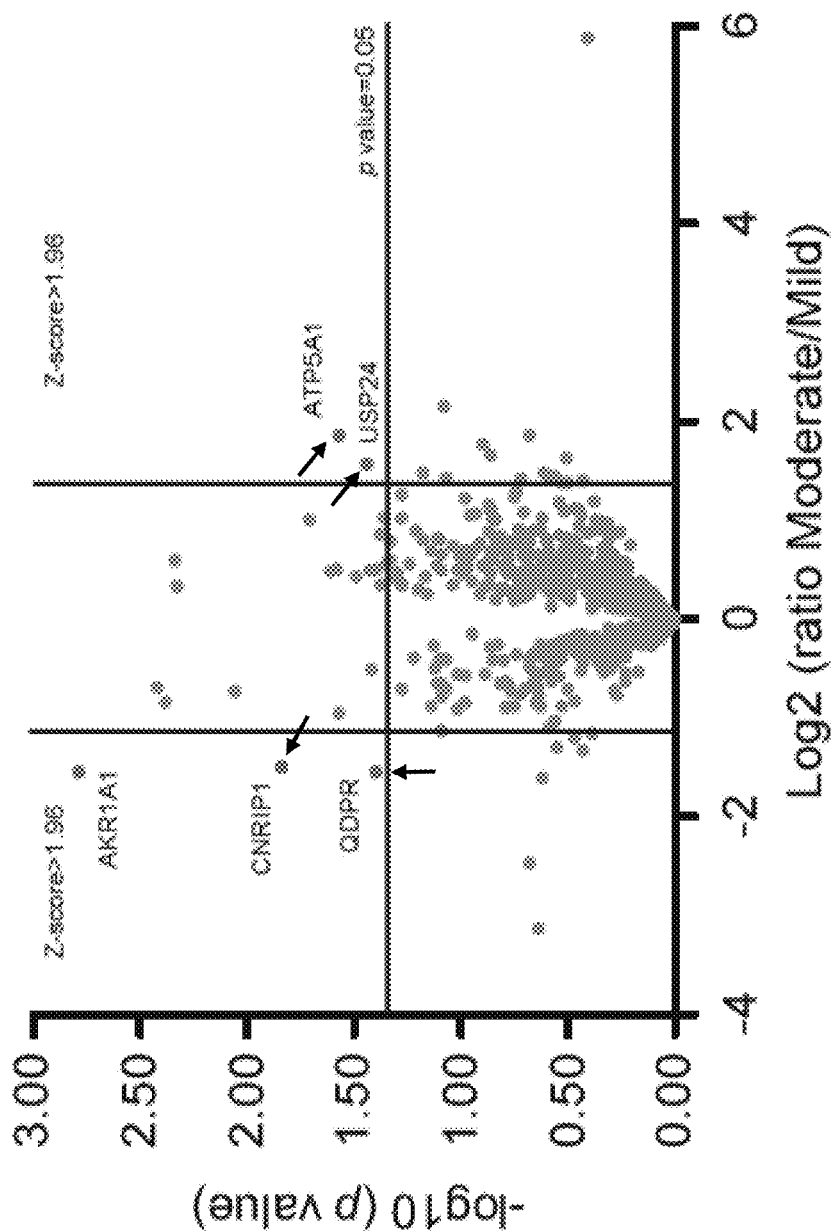

FIGS. 5A-5C. Confirmation of EEV proteins selectively modified in PD patients by Volcano plots. The protein ratios (log 2(ratio)) of the three comparison (FIG. 5A: mild PD/CTRL, FIG. 5B: moderate PD/CTRL, and FIG. 5C: moderate PD/mild PD) were plotted over the corresponding Welch's test p value (−log 10(p-value)). The graphs display a V shape, as expected, and only the proteins falling outside the limits of a p value<0.05 and absolute value of z-score>1.96 (identified by black lines) were considered as variant proteins (arrows). Two variant proteins were excluded given that they were quantified using only one peptide. Abbreviations: CTRL: Control; PD, Parkinson's disease.

DETAILED DESCRIPTION

The present description relates to the proteomic analysis of erythrocyte-derived extracellular vesicles (EEV) and the identification of protein biomarkers whose expression levels within EEV correlate with different Parkinson's disease (PD) states.

In one aspect, the present description relates to a method for clinically assessing Parkinson's disease in a human subject, based on the expression level of one or more protein biomarker(s) that may correlate with or be indicative of the subject's Parkinson's disease state. As used herein, the expression "clinically assessing" or "clinical assessment" in the context of PD refers to an evaluation of a subject's PD state, which may or may not occur in a clinical setting, and which may or may not be performed by a health care professional. For example, clinically assessing may comprise screening and/or diagnosing PD in a subject having or suspected of having PD, staging a subject's PD, monitoring the progression of PD in a subject, monitoring the effect of PD medication or treatment (e.g., over time), or any combination thereof. The use of the methods described herein with other methods for clinically assessing PD subjects is also envisaged.

In some aspects, the methods described herein may comprise obtaining a preparation of isolated erythrocyte-derived extracellular vesicles (EEV) from a blood sample of a subject having or suspected of having Parkinson's disease. As used herein, the expression "extracellular vesicles" (EV) refers to subcellular membrane vesicles found in the extracellular environment (e.g., bodily fluids) that originate from cells, and which range in size from about 20 nm to about 1000 nm. EV may comprise exosomes, microvesicles (MV), multivesicular endosomes (MVE), or vesicles produced by apoptotic bodies, or any combination thereof, as well as other types of extracellular vesicles. Whereas the majority of the circulating EV that are detected by flow cytofluorometric assays are likely to be MV, we do not completely exclude the potential contribution of larger exosomes or vesicles produced by apoptotic bodies. In some embodiments, the EV of the present description comprise vesicles between about 30, 40, 50, 60, 70, 80, 90, or 100 nm to about 500, 600, 700, 800, 900, or 1000 nm in size. In some embodiments, the EV of the present description comprise vesicles from 100 nm to 1000 nm in size. In some embodiments, the EV of the present description comprise vesicles between 150 nm to 1000 nm in size. All EV are composed of membrane proteins and lipids, as well as cytoplasmic components of the cell from which they originate, such as mRNA and miRNA, organelles or infectious particles (e.g., prions, virus). A variety of methods may be used to determine the origin of EV. For example, cell surface markers (e.g., with immuno-labeling and/or flow cytometry techniques) may be used to identify, enrich/purify/isolate, and/or quantify EV according to their cell of origin. Examples of such markers include: CD235a+ (erythrocytes), CD31+/CD41-(endothelial cells), CD41+ (platelets), CD45+ (leukocytes), CD45+ CD14+ (monocytes), and CD45+ CD15+(granulocytes). Of particular interest for the present description are markers that are present in (or specific for) EEV that may be used to identify, enrich/purify/isolate, and/or quantify EEV from other types of EV. Examples of such EEV markers include endosome or membrane-bonding proteins such as TSG101 and Rabs (enriched in exosomes), tetraspanins such as CD9, CD63 and CD81 (enriched in exosomes), golgi and mitochondrial proteins (enriched in MVs and absent in exosomes) (Lotvall et al., 2014). In some embodiments, the EEVs of the present description may comprise one or more of the EEV protein(s) listed in Table 4.

As used herein, the expression "[marker]+EV" or "[marker]-positive" in relation to extracellular vesicles refers to the presence or detectability of that marker in an EV population of interest, regardless of whether that marker is actually detected (e.g., using an immunolabel). Conversely, the expression "[marker]-EV" or "[marker]-negative EV" refers to the absence or lack of detectability of that marker in an EV population of interest, regardless of whether that marker is actually detected (e.g., using an immunolabel). For example, the expression "CD235+EV" or "CD235a-positive EV" means EV that comprise the marker CD235a (Glycophorin A).

As used herein, the term "protein biomarker" refers to a molecular indicator that is a polypeptide or protein that is associated with a particular pathological or physiological state (e.g., PD disease state). For example, the expression "Parkinson's disease biomarker" or "PD biomarker" refers to a molecular indicator that is associated with the presence, stage, and/or progression of PD in a subject. Furthermore, the term "EEV protein biomarker" refers to a protein biomarker that is expressed in EEV, whose level of expression is associated with a particular pathological or physiological state (e.g., PD disease state).

In some embodiments, obtaining a preparation of isolated EEV from a blood sample of a subject (e.g., a subject having or suspected of having Parkinson's disease) may involve identifying, enriching/purifying/isolating, and/or quantifying EEV in a blood sample from the subject. In some embodiments, the blood samples may be processed to obtain platelet-free plasma (PFP), and the preparation of isolated EEV may be prepared from PFP. As used herein, the terms "enriched", "purified", "isolated" and the like, refer to either removing contaminants from a biological sample and/or increasing the concentration of an analyte of interest (e.g., EEV) in the sample, to an extent that is not found in nature. In some embodiments, identifying, enriching/purifying/isolating, and/or quantifying EEV may involve flow cytometry, differential centrifugation, nanomembrane ultrafiltration, immunoabsorbent capture, size-exclusion chromatography, ultracentrifugation, magnetic activated cell sorting (MACS), nanoparticle tracking analysis, light scattering, electrophoretic light scattering, dynamic light scattering, electron microscopy or any combination thereof, or using other techniques that can separate vesicles based on their size and/or surface protein expression. Quantifying EEVs may also be performed by methods such as nanoparticle tracking (NTA), biochemical approaches and semi-quantitative electron microscopy approaches. In some embodiments, the methods described herein may further comprise quantifying the level of EEV in a blood sample from a subject. The quantification of EEV may be expressed as a relative value by normalizing the number of EEV (e.g., in terms of the total number of erythrocytes).

In some embodiments, preparations of isolated EEV described herein may comprise at least 70%, 75%, 80%, 85%, 90%, 95%, or 99% (e.g., by weight or number) of EEV, and/or less than 30%, 25%, 20%, 15%, 10%, 5%, or 1% (e.g., by weight or number) of non-EEV.

In some embodiments, the methods described herein may comprise obtaining a blood sample from a subject that is less than 5 mL, less than 4 mL, less than 3 mL, less than 2 mL, less than 1 mL, less than 900 μL, less than 800 μL, less than 700 μL, less than 600 μL, less than 500 μL, less than 400 μL, less than 300 μL, less than 200 μL, less than 100 μL, less than 50 μL, less than 40 μL, less than 30 μL, less than 25 μL, less than 20 μL, or less than 10 μL.

In some embodiments, the methods described herein may comprise detecting or determining the expression level of an EEV protein biomarker that is differentially expressed in controls (e.g., non-PD subjects) and/or in different PD states (e.g., mild, moderate, or severe), for example based on the unified Parkinson's disease rating scale (UPDRS). As used herein, the expression "mild PD patients" are defined as patients characterized by a UPDRS score of lower than 37; "moderate PD patients" are defined as patients characterized by a UPDRS score of between 37 and and "severe PD patients" are defined as patients characterized by a UPDRS score of greater than 75. In some embodiments, the EEV protein biomarkers described herein may be used, for example, to distinguish between mild, moderate and severe PD patients. In some embodiments, the EEV protein biomarkers described herein may be used to distinguish between patients characterized by UPDRS scores within different ranges from those mentioned above. As used herein, "control subjects" or "controls" refer to non-PD subjects (e.g., healthy subjects).

In some embodiments, the methods described herein comprise determining the expression level(s) of one or more protein biomarker(s) in a preparation of isolated EEV, wherein the protein biomarker(s) is/are one or more of the proteins defined in the Table below.

In some embodiments, the protein biomarkers identified herein as belonging to Group I may be differentially expressed in the EEV of healthy or non-PD control subjects, as compared to those of mild and/or moderate PD subjects. In some embodiments, the protein biomarkers identified herein as belonging to Group II may be differentially expressed in the EEV of mild PD subjects, as compared to those of healthy or non-PD control subjects and/or moderate PD subjects. In some embodiments, the protein biomarkers identified herein as belonging to Group III may be differentially expressed in the EEV of moderate PD subjects, as compared to those of healthy or non-PD control subjects and/or mild PD subjects.

In some embodiments, the methods described herein may comprise determining the expression of one or more of the protein biomarkers described herein, based on the PD state which is to be clinically assessed. For example, different protein biomarkers or combinations of protein biomarkers may be selected based on, for example, the differential expression patterns reported herein (e.g., in Table 3.1 and in FIG. 4C). In some embodiments, the methods described herein may comprise determining the expression of: (i) Alpha/beta hydrolase domain-containing protein 14B, if the subject has or is suspected of having mild or moderate Parkinson's disease; (ii) Alcohol dehydrogenase [NADP (+)], if the subject has or is suspected of having mild Parkinson's disease; (iii) ATP synthase subunit alpha, mitochondrial, if the subject has or is suspected of having moderate Parkinson's disease; or (iv) any combination of (i) to (iii). In some embodiments, the subject is determined to have mild or moderate PD when the expression level of alpha/beta hydrolase domain-containing protein 14B in the preparation of isolated EEV from a blood sample of the subject is lower than that corresponding to a control subject (i.e., not having PD). In some embodiments, the subject is determined to have mild PD when the expression level of alcohol dehydrogenase [NADP(+)] in the preparation of isolated EEV from a blood sample of the subject is higher than that corresponding to a control subject (i.e., not having PD). In some embodiments, the subject is determined to have moderate PD when the expression level of ATP synthase subunit alpha, mitochondrial in the preparation of isolated EEV from a blood sample of the subject is higher than that corresponding to a control subject (i.e., not having PD). In some embodiments, the terms "higher" or "lower" may refer to a difference in expression from the reference value of at least 1.5-fold, 2-fold, 2.5-fold, 3-fold, or 3.5-fold. In some embodiments, methods described herein may comprise determining the expression level(s) of at least one, at

| Groups | Protein biomarker | SEQ ID NO: | Related accession no. | Related UniProt ID | Corresponding gene name |
| --- | --- | --- | --- | --- | --- |
| I (Control) | Axin interactor, dorsalization-associated protein | 1 | NP_073742.2 | Q96BJ3 | AIDA |
| | Alpha/beta hydrolase domain-containing protein 14B | 2 | NP_116139.1 | Q96IU4 | ABHD14B |
| | Glutamine-dependent NAD(+) synthetase | 3 | EAW74792.1 | E9PNF5 | NADSYN1 |
| II (mild PD) | Dihydropteridine reductase | 4 | NP_001293069.1 | QDPR | QDPR |
| | Alcohol dehydrogenase [NADP(+)] | 5 | AAP36383.1 | P14550 | AKR1A1 |
| | CB1 cannabinoid receptor-interacting protein 1 | 6 | NP_056278.1 NP_001104571.1 | B8ZZB8 | CNRIP1 |
| III (moderate PD) | Ubiquitin carboxyl-terminal hydrolase 24 | 7 | NP_056121.2 | Q9UPU5 | USP24 |
| | ATP synthase subunit alpha, mitochondrial | 8 | EAX01470.1 | K7EQH4 | ATP5A1 | least two, at least three, at least four, at least five, at least six, at least seven, or all eight of the protein biomarker(s):

(a) Axin interactor, dorsalization-associated protein (represented by SEQ ID NO: 1);

(b) Alpha/beta hydrolase domain-containing protein 14B (represented by SEQ ID NO: 2);

(c) Glutamine-dependent NAD(+) synthetase (represented by SEQ ID NO: 3);
(d) Dihydropteridine reductase (represented by SEQ ID NO: 4);
(e) Alcohol dehydrogenase [NADP(+)] (represented by SEQ ID NO: 5);
(f) CB1 cannabinoid receptor-interacting protein 1 (represented by SEQ ID NO: 6);
(g) Ubiquitin carboxyl-terminal hydrolase 24 (represented by SEQ ID NO: 7); and
(h) ATP synthase subunit alpha, mitochondrial (represented by SEQ ID NO: 8).

In some embodiments, the expression level of one or more of the protein biomarker(s) described herein may be determined by detecting and/or quantifying the presence of a polypeptide fragment of any one of the polypeptides of SEQ ID NOs: 1-8. Such fragments may be comprise or consist of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 95, 100, 125, 150, 175, 200, or more contiguous amino acids of any one of SEQ ID NOs: 1-8. In some embodiments, the polypeptides of any one of SEQ ID NOs: 1-8 may be present in the EEV (or a preparation of isolated EEV) as a fragment of SEQ ID NOs: 1-8. Detection of such fragments are considered within the scope of the present description. In some embodiments, a protein biomarker described herein may comprise one or more fragments of any one of SEQ ID NOs: 1-8, for example a fragment comprising or consisting of: residues 127-192 of SEQ ID NO: 1; residues 188-200 of SEQ ID NO: 2; residues 112-260 or residues 349-446 of SEQ ID NO: 3; residues 1-213 of SEQ ID NO: 4; residues 1-325 of SEQ ID NO: 5; residues 1-110 or residues 84-110 of SEQ ID NO: 6; residues 2570-2620 of SEQ ID NO: 7; or residues 51-161, residues 111-137, or residues 53-152 of SEQ ID NO: 8.

In some embodiments, methods described herein may comprise determining the expression level(s) of at least one, at least two, at least three, at least four, at least five, at least six, at least seven, or all eight of the protein biomarker(s) encoded by the human genes AIDA, ABHD148, NADSYN1, QDPR, AKR1A1, CNRIP1, USP24, and ATP5A1.

In some embodiments, methods described herein may comprise determining the expression level(s) of at least one, at least two, at least three, at least four, at least five, at least six, at least seven, or all eight of the protein biomarker(s) defined by accession numbers: NP_073742.2, NP_116139.1, EAW74792.1, NP_001293069.1, AAP36383.1, NP_056278.1, NP_001104571.1, NP_056121.2, and EAX01470.1.

In some embodiments, protein biomarker (a) may be at least 70%, 75%, 80%, 85%, 90%, or 95% identical to the amino acid sequence of SEQ ID NO: 1. In some embodiments, protein biomarker (b) may be at least 70%, 75%, 80%, 85%, 90%, or 95% identical to the amino acid sequence of SEQ ID NO: 2. In some embodiments, protein biomarker (c) may be at least 70%, 75%, 80%, 85%, 90%, or 95% identical to the amino acid sequence of SEQ ID NO: 3. In some embodiments, protein biomarker (d) may be at least 70%, 75%, 80%, 85%, 90%, or 95% identical to the amino acid sequence of SEQ ID NO: 4. In some embodiments, protein biomarker (e) may be at least 70%, 75%, 80%, 85%, 90%, or 95% identical to the amino acid sequence of SEQ ID NO: 5. In some embodiments, protein biomarker (f) may be at least 70%, 75%, 80%, 85%, 90%, or 95% identical to the amino acid sequence of SEQ ID NO: 6. In some embodiments, protein biomarker (g) may be at least 70%, 75%, 80%, 85%, 90%, or 95% identical to the amino acid sequence of SEQ ID NO: 7. In some embodiments, protein biomarker (f) may be at least 70%, 75%, 80%, 85%, 90%, or 95% identical to the amino acid sequence of SEQ ID NO: 8.

In some embodiments, the methods described herein may comprise determining the expression levels of an EEV protein signature comprising any combination of the protein biomarkers (a) to (h). In some embodiments, the methods described herein may comprise determining the expression levels of at least one of protein biomarkers (a), (b), and (c) [Group I]; at least one of protein biomarkers (d), (e), and (f) [Group II]; and/or at least one of protein biomarkers (g) and (h) [Group III].

In some embodiments, the methods described herein may further comprise comparing the expression level of the protein biomarker(s) so detected and comparing the expression level to a reference value corresponding to that of a control group, non-PD group, mild PD group, moderate PF group, or severe PD group.

In some embodiments, the EEV protein biomarkers described herein do not comprise alpha-synuclein; and/or the methods described herein do not comprise detecting and/or quantifying alpha-synuclein.

In some embodiments, the expression level(s) of one or more of the protein biomarker(s) in the preparation of isolated EEV may comprise contacting the protein biomarker with an antibody directed against the protein biomarker (e.g., an immunoassay). In some embodiments, the antibody specifically binds to the polypeptide of any one of SEQ ID NOs: 1-8. Antibodies against the proteins of SEQ ID NOs: 1-8 are commercially available, for example from Novus Biologicals (e.g., catalog numbers NBP1-88323, NBP2-26122, H00055191-M01, H00005860-M02, NBP2-02164, NBP1-86800, NB100-40830, and NBP2-38525, respectively). In some embodiments, antibodies described herein may bind to, or be raised against, a fragment of any one of SEQ ID NOs: 1-8, for example a fragment comprising or consisting of: residues 127-192 of SEQ ID NO: 1; residues 188-200 of SEQ ID NO: 2; residues 112-260 or residues 349-446 of SEQ ID NO: 3; residues 1-213 of SEQ ID NO: 4; residues 1-325 of SEQ ID NO: 5; residues 84-110 of SEQ ID NO: 6; residues 2570-2620 of SEQ ID NO: 7; or residues 53-152 of SEQ ID NO: 8. In some embodiments, antibodies described herein may bind to an epitope comprising or consisting of at least 5, 6, 7, 8, 9, 10, 11, 12, 13, 14, 16, 17, 18, 19, 20, 21, 22, 23, 24, 25, 26, 27, 28, 29, or 30 contiguous residues of any one of SEQ ID NOs: 1-8.

As used herein, the term "antibody" may encompass any type of antibody, including but not limited to monoclonal antibodies, polyclonal antibodies, "antigen-binding fragments" (or portion), such as Fab, Fab', F(ab')2, Fd, Fv, Fc, etc., of intact antibodies that retain the ability to specifically bind to a given antigen (e.g., an EEV protein described herein), an isolated complementarity determining region (CDR), bispecific antibodies, heteroconjugate antibodies, mutants thereof, fusion proteins having an antibody, or antigen-binding fragment thereof, (e.g., a domain antibody), single chain (ScFv) and single domain antibodies (e.g., shark and camelid antibodies), maxibodies, minibodies, intrabodies, diabodies, triabodies, tetrabodies, v-NAR and bis-scFv, humanized antibodies, chimeric antibodies and any other modified configuration of the immunoglobulin molecule that includes an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the expression level(s) of one or more of the protein biomarker(s) in the preparation of isolated EEV may comprise mass spectrometry (e.g., nano liquid chromatography tandem mass spectrometry (nanoLC MS/MS)).

In some embodiments, the methods described herein may comprise combining the expression of one or more of the protein biomarker(s) in the preparation of isolated EEV with the quantity of EEV to increase the power of a biomarker described herein.

In some embodiments, the methods described herein may further comprise determining the expression level(s) of one or more of the EEV protein(s) listed in Table 4 (Proteins identified in the EEV proteome), wherein the one or more EEV protein(s) does not comprise (a) to (h). The expression level of one or more EEV proteins that are not differentially expressed between PD states may be useful for example as normalization parameters in conjunction with the one or more of the protein biomarkers (a) to (h).

In some embodiments, the methods described herein may comprise determining the expression level(s) of one or more of the EEV protein(s) defined by UniProt ID: P02549, P11277, P16157, P02730, P55072, P16452, P11171, P04040, Q13228, B4DT77, Q8WUM4, P35612, P68871, Q00610, P69905, B4DVE7, J3QLD9, P08758, P09525, O75955, P11142, P32119, P00491, P27105, P00918, P23634, C9JIF9, P00915, P63261, Q5VU58, P30041, E7EU23, Q00013, E7EV01, J3KPS3, Q08495, P23276, P69892, P60174, P62258, O75326, O75340, E7EV99, Q5VZU9, P53396, C9J0K6, P04406, P07738, B7Z319, Q86X55, P07195, P23526, Q32Q12, B7Z7A9, P11166, P22303, Q9NP58, P40925, P00352, F2Z2V0, K7EMC9, F5H7S3, A6NN80, P30043, H7BXD5, P04083, P62937, P37837, Q06830, O75131, P00390, E7EQB2, P07384, P02042, P30086, P35613, Q9H0U4, P63092, P48506, P06702, Q9UBV8, P17931, P28066, P07451, E7EQ12, P50895, P28074, G3V5Z7, P25786, G3V1D3, P49247, Q5T9B7, P25789, B4E022, J3QS39, H0Y7A7, P28070, Q9H4G4, Q9BY43, P48426, P28289, P07911, Q9GZP4, P78417, P25788, O14818, P08107, H0YD13, P61225, P05109, P23528, Q99808, P84077, P31946, C9JIS1, P53990, Q99497, F5H7U0, B7Z7E9, P62834, P04899, P25325, Q9NP79, P00492, Q16531, P22314, P00441, H7BY58, P10768, P09543, P06733, P26038, O75368, K7EQ48, P25787, P49721, F5H8J2, C9J9P4, P09211, B5MDF5, P07900, K7EQ02, Q13630, F5H0T1, P50502, P20618, P62805, P51148, H7C2G2, J3KQ18, H3BPK3, B4DIT7, O43633, B4DQH4, Q9UN37, I3L397, Q9Y5Z4, Q9UKV8, F5H442, H3BLV0, P02008, E7EPV7, P63104, P02724, U3KQE2, Q9NP59, Q5QPM9, C9J8U2, P61981, Q9UQ80, E5RJR5, Q9NRV9, Q9H444, P10599, Q5VSJ9, Q9UK41, Q9Y3I1, P61026, Q14974, P27797, P18669, P54725, P30613, P63000, P05164, F5GWY2, P48637, F5H5V4, G5E9R5, P46976, P28072, P26447, F5GXQ0, P08754, Q99436, P62942, U3KQK0, J3QKR3, P01116, P13489, Q08722, Q5T123, Q8WYQ7, O75695, P00167, Q9Y4D1, P11021, H7C1D4, P07737, M0R389, A6NJA2, P10644, Q9BS40, G5EA52, P53004, Q04656, H9KV70, O00299, F8WF69, G3V2F7, F8WDS9, P60891, K7ESE8, H0YNE3, P16930, F8VSD4, P07203, P62328, E5RIW3, M0R0Y2, P15374, P04921, H0YDI1, B4E220, C9JEN3, F5H2R5, Q53TN4, Q9NZD4, Q8NHG7, Q5JYX0, Q71RC9, E9PNW4, P09105, R4GN98, O75531, Q5T6W5, F5H4Q5, J3QK90, H3BV85, Q9NRX4, H3BS66, E7ESC6, P68402, Q9BRF8, P08246, E9PN50, E7EUC7, B8ZZB8, E9PCS3, P59666, O15400, P00338, P61970, E7EMV0, F5GY90, P61020, Q99828, B4DUA0, C9JTY3, P27348, H0YKZ7, P08238, J3KQP6, A6NMU3, P53985, F6USW4, O14964, P20020, P36959, Q9Y376, Q9Y6M5, Q81Z83, Q99459, P06132, J3KNT0, P49189, H3BNT7, P05023, P34932, K7EMV3, Q8IU68, E7ENZ3, Q5TZA2, Q9P203, Q7LBR1, U3KQ56, H0YJ11, Q9UDT6, P09960, Q5HY54, E9PJL5, G3V2U7, E9PQN4, Q9BSL1, Q04917, B7ZBP9, Q8NDC0, P68133, P69891, S4R3Y4, I3L3E4, Q16570, Q5VY30, E7END7, Q5VU59, P17066, Q04760, D6RD66, K7EM02, P14209, E9PIR7, K7EMQ9, P15531, H7BZT4, O00560, Q9BVM4, K7EKH5, P49773, H0YBY6, Q9Y624, B1AKQ8, K7EKN6, I3L0K2, A8MXY0, O14773, E9PNW0, Q5TDH0, Q96JM4, F5GWT9, F2Z3J2, J3QL74, E9PJC7, Q9H936, D6RD63, Q6B0K9, Q31611, H7BY04, Q9UL25, H7C3P7, P08311, E9PE37, G3V1N2, P00387, O75339, P14324, K7EKG2, P02549, P11277, P16157, P55072, P111714, P35579, Q8WUM4, P02730, P16452, P04040, A0A087WVQ6, P35612, P16157, Q14254, P20073, O75955, P53396, P06753, P49368, P236344, P11142, P60709, Q5T4S7, P78371, P28289, P50395, P27105, P68871, P02730, Q00013, J3KPS3, P00352, Q86VP6, P49327, Q13228, P00915, P50991, P50990, P32119, P50995, P69905, P00558, H7BXK9, P08758, P09525, P07900, P48643, P07384, P22314, P04406, Q08495, Q99832, P29144, P30041, E9PM69, P40227, P50570, E7EQB2, P31948, E7ESC6, E7EV99, P62258, P30613, A0A0G2JIW1, Q16531, P11021, F5H2F4, P07195, P45974, O43242, C9J0K6, P08133, Q13200, P23276, P34932, A0A0A0MSI0, Q9Y230, Q5XPI4, P68871, P60174, P00491, C9JIF9, H7BYY1, P35998, P17987, P09543, Q99460, Q9Y4E8, Q90009, P26038, P04083, P30043, P11166, P00918, P06733, Q5TDH0, B0QZ18, O75326, P05164, Q9Y265, P29401, I3L0N3, Q4VB86, P11277, P13716, P07738, P48506, Q99816, O14818, P23526, P61225, O00231, P11413, P00338, Q99808, A6NJA2, Q06323, or any combination thereof.

In some embodiments, the methods described herein may comprise determining the expression level(s) of one or more of the EEV protein(s) defined by protein accession number: NP_000017.1, NP_000022.3, NP_000028.3, NP_000034.1, NP_000036.2, NP_000043.4, NP_000058.1, NP_000110.2, NP_000128.1, NP_000134.2, NP_000149.3, NP_000166.2, NP_000169.1, NP_000175.1, NP_000185.1, NP_000230.1, NP_000241.1, NP_000260.1, NP_000261.2, NP_000276.2, NP_000280.1, NP_000282.1, NP_000289.1, NP_000311.2, NP_000333.1, NP_000338.3, NP_000356.1, NP_000365.3, NP_000366.1, NP_000382.3, NP_000389.1, NP_000393.4, NP_000410.2, NP_000411.1, NP_000421.1, NP_000445.1, NP_000471.1, NP_000507.1, NP_000508.1, NP_000509.1, NP_000510.1, NP_000549.1, NP_000550.2, NP_000572.2, NP_000623.2, NP_000628.2, NP_000656.1, NP_000678.1, NP_000680.2, NP_000687.3, NP_000691.1, NP_000692.2, NP_000703.2, NP_000704.1, NP_000792.1, NP_000843.1, NP_000886.1, NP_001001323.1, NP_001001396.1, NP_001001521.1, NP_001002021.2, NP_001002857.1, NP_001002858.1, NP_001002860.2, NP_001003938.1, NP_001003945.1, NP_001005360.1, NP_001005361.1, NP_001005362.1, NP_001005386.1, NP_001005753.1, NP_001007068.1, NP_001007069.1, NP_001007070.1, NP_001007071.1, NP_001008390.1, NP_001008800.1, NP_001009185.1, NP_001009186.1, NP_001009570.1, NP_001010935.1, NP_001010942.1, NP_001013275.1, NP_001013454.1, NP_001017963.2, NP_001019397.1, NP_001019398.1, NP_001019399.1, NP_001019820.1, NP_001020029.1, NP_001020276.1, NP_001020560.1, NP_001020561.1, NP_001026897.1, NP_001026997.1, NP_001186041.1, NP_001186054.1, NP_001186092.1,
NP_001027017.1, NP_001028196.1, NP_001028690.1, NP_001186701.1, NP_001186702.1, NP_001186703.1,
NP_001028691.1, NP_001028692.1, NP_001029197.1, NP_001186883.1, NP_001188412.1, NP_001189342.1,
NP_001029249.1, NP_001030611.1, NP_001034221.1, NP_001189343.1, NP_001189360.1, NP_001191331.1,
NP_001034271.1, NP_001034288.1, NP_001034455.1, NP_001191382.1, NP_001191439.1, NP_001192176.1,
NP_001034456.1, NP_001034679.2, NP_001034680.2, NP_001192177.1, NP_001192179.1, NP_001192180.1,
NP_001034708.1, NP_001034891.1, NP_001035517.1, NP_001193469.1, NP_001193665.1, NP_001229573.1,
NP_001035784.1, NP_001035810.1, NP_001035941.1, NP_001229753.1, NP_001229754.1, NP_001229791.1,
NP_001036816.1, NP_001036817.1, NP_001036818.1, NP_001230199.1, NP_001230200.1, NP_001230587.1,
NP_001055.1, NP_001070654.1, NP_001070956.1, NP_001230588.1, NP_001230647.1, NP_001230648.1,
NP_001070957.1, NP_001070958.1, NP_001071643.1, NP_001230865.1, NP_001230869.1, NP_001230870.1,
NP_001071645.1, NP_001073379.1, NP_001077086.1, NP_001230871.1, NP_001230889.1, NP_001231367.1,
NP_001077861.1, NP_001087.2, NP_001091.1, NP_001231653.1, NP_001231867.1, NP_001238846.1,
NP_001092.1, NP_001092006.1, NP_001092925.1, NP_001238847.1, NP_001238850.1, NP_001238851.1,
NP_001096137.1, NP_001096138.1, NP_001098985.1, NP_001238965.1, NP_001238966.1, NP_001238968.1,
NP_001099000.1, NP_001107606.1, NP_001107607.1, NP_001238978.1, NP_001238979.1, NP_001239007.1,
NP_001107608.1, NP_001107609.1, NP_001107610.1, NP_001239008.1, NP_001240752.1, NP_001241682.1,
NP_001107611.1, NP_001108628.1, NP_001112362.1, NP_001242941.1, NP_001243024.1, NP_001243064.1,
NP_001116370.1, NP_001116423.1, NP_001116849.1, NP_001243121.1, NP_001243513.1, NP_001243572.1,
NP_001116850.1, NP_001118.3, NP_001120855.1, NP_001243573.1, NP_001243615.1, NP_001243650.1,
NP_001121776.1, NP_001121777.1, NP_001121778.1, NP_001243692.1, NP_001243728.1, NP_001243838.1,
NP_001122060.3, NP_001122301.1, NP_001122302.1, NP_001244.1, NP_001244126.1, NP_001244127.1,
NP_001122303.1, NP_001123291.1, NP_001123654.1, NP_001244305.1, NP_001244315.1, NP_001244326.1,
NP_001123655.1, NP_001123989.1, NP_001124197.1, NP_001244327.1, NP_001244328.1, NP_001244919.1,
NP_001124321.1, NP_001124322.1, NP_001124384.1, NP_001244928.1, NP_001244955.1, NP_001244957.1,
NP_001128527.1, NP_001128711.1, NP_001129171.1, NP_001245217.1, NP_001245218.1, NP_001247421.1,
NP_001129172.1, NP_001129173.1, NP_001129174.1, NP_001247422.1, NP_001247423.1, NP_001247424.1,
NP_001129293.1, NP_001129294.1, NP_001129333.1, NP_001247425.1, NP_001248341.1, NP_001248342.1,
NP_001129487.1, NP_001129511.1, NP_001135827.1, NP_001252518.1, NP_001252519.1, NP_001252520.1,
NP_001135828.1, NP_001135917.1, NP_001135918.1, NP_001254485.1, NP_001254486.1, NP_001254487.1,
NP_001136336.2, NP_001137359.1, NP_001137430.1, NP_001254488.1, NP_001257291.1, NP_001257292.1,
NP_001137457.1, NP_001138404.1, NP_001138436.1, NP_001257356.1, NP_001257411.1, NP_001257449.1,
NP_001138437.1, NP_001138438.1, NP_001138439.1, NP_001257881.1, NP_001257904.1, NP_001257905.1,
NP_001138440.1, NP_001138441.1, NP_001138442.1, NP_001257906.1, NP_001257907.1, NP_001258522.1,
NP_001138443.1, NP_001138868.1, NP_001138872.1, NP_001258670.1, NP_001258671.1, NP_001258708.1,
NP_001139280.1, NP_001139281.1, NP_001139411.1, NP_001258709.1, NP_001258710.1, NP_001258898.1,
NP_001139412.1, NP_001139501.1, NP_001139502.1, NP_001258899.1, NP_001258900.1, NP_001259025.1,
NP_001139508.2, NP_001139509.1, NP_001139748.1, NP_001263218.1, NP_001263219.1, NP_001263249.1,
NP_001139786.1, NP_001144.1, NP_001145.1, NP_001263382.1, NP_001264693.1, NP_001265118.1,
NP_001146.2, NP_001147.1, NP_001148.1, NP_001265120.1, NP_001265121.1, NP_001265122.1,
NP_001152759.1, NP_001153705.1, NP_001153706.1, NP_001265123.1, NP_001265189.1, NP_001265190.1,
NP_001154840.1, NP_001155059.1, NP_001155238.1, NP_001265191.1, NP_001265192.1, NP_001265193.1,
NP_001155901.1, NP_001156467.1, NP_001156521.1, NP_001265194.1, NP_001265195.1, NP_001265228.1,
NP_001157565.1, NP_001157566.1, NP_001157567.1, NP_001265336.1, NP_001265337.1, NP_001265338.1,
NP_001158095.1, NP_001158302.1, NP_001158886.1, NP_001265362.1, NP_001265443.1, NP_001265543.1,
NP_001158887.1, NP_001158888.1, NP_001159418.1, NP_001265568.1, NP_001265637.1, NP_001265638.1,
NP_001159477.1, NP_001159478.1, NP_001159491.1, NP_001265641.1, NP_001268457.1, NP_001269091.1,
NP_001159528.1, NP_001159529.1, NP_001159583.1, NP_001269098.1, NP_001269153.1, NP_001269332.1,
NP_001159584.1, NP_001159585.1, NP_001159586.1, NP_001269333.1, NP_001269374.1, NP_001269378.1,
NP_001159588.1, NP_001159756.1, NP_001159757.1, NP_001269505.1, NP_001269508.1, NP_001269546.1,
NP_001159897.1, NP_001159932.1, NP_001159933.1, NP_001269547.1, NP_001269548.1, NP_001269549.1,
NP_001159934.1, NP_001159968.1, NP_001160158.1, NP_001269581.1, NP_001269582.1, NP_001269636.1,
NP_001160159.1, NP_001160160.1, NP_001161694.1, NP_001269781.1, NP_001269782.1, NP_001269783.1,
NP_001161971.1, NP_001165131.1, NP_001165132.1, NP_001269836.1, NP_001269838.1, NP_001269879.1,
NP_001165901.1, NP_001165902.1, NP_001165906.1, NP_001269881.1, NP_001269882.1, NP_001269884.1,
NP_001167568.1, NP_001170775.1, NP_001171588.1, NP_001269885.1, NP_001269961.1, NP_001273063.1,
NP_001171589.1, NP_001171649.1, NP_001171650.1, NP_001273102.1, NP_001273103.1, NP_001273104.1,
NP_001171651.1, NP_001171675.1, NP_001171676.1, NP_001273105.1, NP_001273106.1, NP_001273162.1,
NP_001171677.1, NP_001171725.1, NP_001171983.1, NP_001273163.1, NP_001273164.1, NP_001273165.1,
NP_001171984.1, NP_001172006.1, NP_001172007.1, NP_001273166.1, NP_001273178.1, NP_001273300.1,
NP_001177645.1, NP_001177736.1, NP_001177931.1, NP_001273301.1, NP_001273659.1, NP_001273718.1,
NP_001177932.1, NP_001177966.1, NP_001177989.1, NP_001273758.1, NP_001273939.1, NP_001274522.1,
NP_001177990.1, NP_001180262.1, NP_001180446.1, NP_001274523.1, NP_001275508.1, NP_001275509.1,
NP_001180473.1, NP_001182016.1, NP_001182031.1, NP_001275510.1, NP_001275582.1, NP_001276032.1,
NP_001182032.1, NP_001182033.1, NP_001184044.1, NP_001276033.1, NP_001276062.1, NP_001276674.1,
NP_001185739.1, NP_001185771.1, NP_001185797.1, NP_001276675.1, NP_001276840.1, NP_001276977.1,
NP_001185798.1, NP_001185883.1, NP_001186040.1, NP_001277151.1, NP_001277403.1, NP_001278825.1,

NP_001278977.1, NP_001279.2, NP_001280014.1,
NP_001280241.1, NP_001287843.1, NP_001287910.1,
NP_001288169.1, NP_001288170.1, NP_001288171.1,
NP_001288172.1, NP_001288758.1, NP_001288759.1,
NP_001289546.1, NP_001289550.1, NP_001289551.1,
NP_001289745.1, NP_001289746.1, NP_001290182.1,
NP_001290203.1, NP_001290204.1, NP_001291278.1,
NP_001291380.1, NP_001291381.1, NP_001291391.1,
NP_001291392.1, NP_001291394.1, NP_001291395.1,
NP_001291688.1, NP_001291689.1, NP_001293008.1,
NP_001293013.1, NP_001293069.1, NP_001293083.1,
NP_001293084.1, NP_001295030.1, NP_001295119.1,
NP_001295182.1, NP_001296360.1, NP_001296769.1,
NP_001298131.1, NP_001300893.1, NP_001300894.1,
NP_001302466.1, NP_001303270.1, NP_001303283.1,
NP_001303284.1, NP_001303285.1, NP_001303286.1,
NP_001303287.1, NP_001303303.1, NP_001303991.1,
NP_001303992.1, NP_001303993.1, NP_001304262.1,
NP_001304263.1, NP_001304674.1, NP_001304712.1,
NP_001304753.1, NP_001304754.1, NP_001304755.1,
NP_001304852.1, NP_001304924.1, NP_001305051.1,
NP_001305150.1, NP_001305151.1, NP_001305261.1,
NP_001305438.1, NP_001305439.1, NP_001305804.1,
NP_001306001.1, NP_001306002.1, NP_001306013.1,
NP_001306045.1, NP_001306126.1, NP_001306127.1,
NP_001306130.1, NP_001307.2, NP_001307269.1,
NP_001307271.1, NP_001307508.1, NP_001307548.1,
NP_001307627.1, NP_001307629.1, NP_001307631.1,
NP_001307760.1, NP_001308022.1, NP_001308120.1,
NP_001308296.1, NP_001308297.1, NP_001308298.1,
NP_001308967.1, NP_001308968.1, NP_001308969.1,
NP_001308970.1, NP_001309013.1, NP_001309014.1,
NP_001309172.1, NP_001309423.1, NP_001309424.1,
NP_001310245.1, NP_001310246.1, NP_001310307.1,
NP_001310308.1, NP_001310309.1, NP_001310310.1,
NP_001310311.1, NP_001310312.1, NP_001310313.1,
NP_001310314.1, NP_001310316.1, NP_001310317.1,
NP_001310318.1, NP_001310319.1, NP_001310320.1,
NP_001310321.1, NP_001310322.1, NP_001310323.1,
NP_001310324.1, NP_001310325.1, NP_001310326.1,
NP_001310327.1, NP_001310328.1, NP_001310329.1,
NP_001310330.1, NP_001310337.1, NP_001310447.1,
NP_001311057.1, NP_001313507.1, NP_001313508.1,
NP_001313509.1, NP_001316501.1, NP_001316838.1,
NP_001316839.1, NP_001316840.1, NP_001316991.1,
NP_001316992.1, NP_001317092.1, NP_001317099.1,
NP_001317141.1, NP_001317145.1, NP_001317186.1,
NP_001317199.1, NP_001317200.1, NP_001317273.1,
NP_001317275.1, NP_001317280.1, NP_001317389.1,
NP_001317390.1, NP_001317517.1, NP_001317541.1,
NP_001317605.1, NP_001317656.1, NP_001317660.1,
NP_001317706.1, NP_001317959.1, NP_001340.2,
NP_001346.1, NP_001348.2, NP_001395.1, NP_001406.1,
NP_001407.1, NP_001419.1, NP_001485.2, NP_001489.1,
NP_001531.1, NP_001535.1, NP_001605.1, NP_001608.1,
NP_001649.1, NP_001654.1, NP_001670.1, NP_001673.2,
NP_001675.3, NP_001681.2, NP_001684.2, NP_001687.1,
NP_001691.1, NP_001715.1, NP_001716.2, NP_001719.2,
NP_001729.1, NP_001737.1, NP_001743.1, NP_001748.1,
NP_001753.1, NP_001768.1, NP_001782.1, NP_001867.2,
NP_001883.4, NP_001902.1, NP_001905.1, NP_001914.3,
NP_001952.1, NP_001963.1, NP_001966.1, NP_001969.2,
NP_001975.1, NP_001995.1, NP_002005.1, NP_002027.2,
NP_002037.2, NP_002052.1, NP_002055.1, NP_002058.2,
NP_002061.1, NP_002063.2, NP_002070.1, NP_002090.4,
NP_002092.1, NP_002094.2, NP_002145.3, NP_002146.2,
NP_002147.2, NP_002256.2, NP_002287.2, NP_002289.2,
NP_002291.1, NP_002297.2, NP_002299.2, NP_002405.1,
NP_002427.1, NP_002435.1, NP_002464.1, NP_002474.4,
NP_002515.1, NP_002558.1, NP_002563.1, NP_002564.1,
NP_002565.1, NP_002617.3, NP_002620.1, NP_002622.2,
NP_002700.1, NP_002706.1, NP_002717.3, NP_002721.1,
NP_002725.1, NP_002736.3, NP_002755.1, NP_002757.2,
NP_002758.1, NP_002777.1, NP_002778.1, NP_002779.1,
NP_002780.1, NP_002781.2, NP_002783.1, NP_002784.1,
NP_002785.1, NP_002786.2, NP_002787.2, NP_002788.1,
NP_002789.1, NP_002790.1, NP_002793.2, NP_002794.1,
NP_002796.4, NP_002797.3, NP_002798.2, NP_002799.3,
NP_002800.2, NP_002801.1, NP_002802.2, NP_002806.2,
NP_002807.1, NP_002808.3, NP_002856.1, NP_002859.1,
NP_002860.2, NP_002865.1, NP_002875.1, NP_002877.2,
NP_002897.1, NP_002930.2, NP_002952.1, NP_002955.2,
NP_002956.1, NP_003013.1, NP_003042.3, NP_003095.2,
NP_003117.2, NP_003266.1, NP_003282.2, NP_003290.1,
NP_003304.1, NP_003320.2, NP_003325.2, NP_003339.1,
NP_003352.2, NP_003379.3, NP_003391.1, NP_003395.1,
NP_003396.1, NP_003397.1, NP_003464.1, NP_003469.2,
NP_003472.2, NP_003486.1, NP_003509.1, NP_003513.1,
NP_003514.2, NP_003516.1, NP_003517.2, NP_003529.1,
NP_003530.1, NP_003531.1, NP_003532.1, NP_003533.1,
NP_003534.1, NP_003535.1, NP_003536.1, NP_003537.1,
NP_003539.1, NP_003560.2, NP_003565.4, NP_003581.1,
NP_003603.1, NP_003604.3, NP_003618.1, NP_003644.2,
NP_003698.1, NP_003711.1, NP_003741.1, NP_003817.1,
NP_003851.1, NP_003899.2, NP_003900.1, NP_003906.2,
NP_003923.2, NP_003935.2, NP_004025.1, NP_004030.1,
NP_004035.2, NP_004085.1, NP_004090.4, NP_004095.4,
NP_004121.2, NP_004152.1, NP_004153.2, NP_004175.2,
NP_004209.2, NP_004227.1, NP_004277.2, NP_004291.1,
NP_004299.1, NP_004300.1, NP_004334.1, NP_004336.3,
NP_004420.1, NP_004428.1, NP_004449.1, NP_004466.2,
NP_004574.2, NP_004595.2, NP_004604.2, NP_004628.4,
NP_004703.1, NP_004777.1, NP_004818.2, NP_004823.1,
NP_004850.1, NP_004883.3, NP_004888.2, NP_004896.1,
NP_004921.1, NP_004936.2, NP_004960.2, NP_004976.2,
NP_004985.2, NP_005013.1, NP_005019.2, NP_005038.1,
NP_005044.1, NP_005172.1, NP_005177.2, NP_005208.1,
NP_005304.3, NP_005317.2, NP_005322.1, NP_005323.1,
NP_005331.1, NP_005336.3, NP_005337.2, NP_005338.1,
NP_005339.3, NP_005361.2, NP_005393.2, NP_005462.1,
NP_005498.1, NP_005546.2, NP_005557.1, NP_005572.2,
NP_005616.2, NP_005680.1, NP_005713.1, NP_005727.1,
NP_005759.4, NP_005787.1, NP_005794.1, NP_005796.1,
NP_005800.3, NP_005836.2, NP_005850.1, NP_005882.2,
NP_005902.1, NP_005908.1, NP_005909.2, NP_005955.3,
NP_005960.1, NP_005989.3, NP_005993.1, NP_006045.1,
NP_006057.1, NP_006079.1, NP_006084.2, NP_006100.2,
NP_006126.1, NP_006127.1, NP_006136.1, NP_006182.2,
NP_006187.2, NP_006254.1, NP_006280.3, NP_006283.1,
NP_006304.1, NP_006311.2, NP_006312.1, NP_006358.1,
NP_006364.2, NP_006375.2, NP_006382.1, NP_006391.1,
NP_006398.1, NP_006409.3, NP_006420.1, NP_006421.2,
NP_006422.1, NP_006487.1, NP_006494.1, NP_006507.2,
NP_006546.1, NP_006576.2, NP_006588.1, NP_006639.3,
NP_006657.1, NP_006693.3, NP_006695.1, NP_006699.2,
NP_006746.1, NP_006750.3, NP_006752.1, NP_006808.1,
NP_006810.1, NP_006817.1, NP_006818.3, NP_006828.2,
NP_006868.3, NP_008839.2, NP_008846.2, NP_008996.1,
NP_009005.1, NP_009030.1, NP_009057.1, NP_009193.2,
NP_009200.2, NP_015565.1, NP_031381.2, NP_033665.1,
NP_036205.1, NP_036220.1, NP_036286.1, NP_036311.3,
NP_036335.1, NP_036365.1, NP_036457.1, NP_036524.1,
NP_036525.1, NP_036557.1, NP_036611.2, NP_037364.1,
NP_037377.1, NP_037506.2, NP_054735.3, NP_054888.2,

NP_054891.2, NP_055018.2, NP_055063.1, NP_055131.2,
NP_055135.1, NP_055176.1, NP_055268.1, NP_055400.1,
NP_055461.1, NP_055490.4, NP_055576.2, NP_055596.3,
NP_055617.1, NP_055622.3, NP_055629.1, NP_055628.2,
NP_055746.3, NP_055807.1, NP_055814.1, NP_055851.1,
NP_055866.1, NP_055955.1, NP_056060.2, NP_056071.2,
NP_056092.2, NP_056107.1, NP_056121.2, NP_056193.2,
NP_056274.3, NP_056358.1, NP_056425.1, NP_056461.1,
NP_056646.1, NP_056949.4, NP_057038.2, NP_057070.3,
NP_057071.2, NP_057087.2, NP_057159.2, NP_057163.1,
NP_057190.2, NP_057215.3, NP_057226.1, NP_057227.2,
NP_057231.1, NP_057256.2, NP_057292.1, NP_057373.1,
NP_057403.1, NP_057406.2, NP_057460.3, NP_057569.2,
NP_057707.3, NP_057717.1, NP_058131.1, NP_058642.1,
NP_059516.2, NP_059522.1, NP_059980.2, NP_060342.2,
NP_060357.1, NP_060468.2, NP_060522.3, NP_060555.2,
NP_060626.2, NP_060637.1, NP_060705.2, NP_060717.1,
NP_060760.2, NP_060810.2, NP_060895.1, NP_060918.2,
NP_061036.3, NP_061072.3, NP_061327.2, NP_061485.1,
NP_061985.2, NP_062427.1, NP_064505.1, NP_064554.3,
NP_064623.2, NP_064711.1, NP_065086.2, NP_065095.2,
NP_065145.2, NP_065147.1, NP_065208.2, NP_065209.2,
NP_065210.2, NP_065211.2, NP_065213.2, NP_065691.2,
NP_065816.2, NP_066569.1, NP_066932.1, NP_066949.2,
NP_066952.1, NP_066953.1, NP_067017.2, NP_068596.2,
NP_068751.4, NP_068803.1, NP_071347.2, NP_071349.3,
NP_071441.1, NP_071738.1, NP_071933.2, NP_073567.1,
NP_073742.2, NP_073744.2, NP_075266.1, NP_075566.2,
NP_077007.1, NP_077307.2, NP_078850.3, NP_078867.2,
NP_078958.2, NP_078974.1, NP_079005.3, NP_079119.3,
NP_109587.1, NP_109591.1, NP_110379.2, NP_112243.1,
NP_113584.3, NP_113618.2, NP_113657.1, NP_113659.3,
NP_115501.2, NP_115618.3, NP_115661.1, NP_115717.3,
NP_115788.1, NP_115797.1, NP_116139.1, NP_116235.2,
NP_116251.4, NP_149101.1, NP_149124.3, NP_203524.1,
NP_426359.1, NP_463460.1, NP_536350.2, NP_536351.1,
NP_536856.2, NP_563578.2, NP_569057.1, NP_570603.2,
NP_619639.3, NP_620164.1, NP_620407.1, NP_631913.3,
NP_647539.1, NP_653164.2, NP_653179.1, NP_653296.2,
NP_659449.3, NP_660202.3, NP_663723.1, NP_663782.2,
NP_665875.1, NP_665876.1, NP_683691.1, NP_683725.1,
NP_683877.1, NP_687033.1, NP_689476.2, NP_689681.2,
NP_689937.2, NP_690610.1, NP_690611.1, NP_694546.1,
NP_694881.1, NP_695012.1, NP_697021.1, NP_699160.2,
NP_703150.1, NP_705935.1, NP_733842.2, NP_775853.2,
NP_775871.2, NP_776049.1, NP_777360.1, NP_777637.1,
NP_778224.1, NP_780775.1, NP_787128.2, NP_789782.1,
NP_848537.1, NP_859047.1, NP_859048.1, NP_859049.2,
NP_870986.1, NP_878255.1, NP_898880.1, NP_919415.2,
NP_919424.1, NP_937792.2, NP_937818.1, NP_937837.1,
NP_938148.1, NP_938149.2, NP_940818.1, NP_940991.1,
NP_940992.1, NP_940993.1, NP_942088.1, NP_942127.1,
NP_942599.1, NP_945189.1, NP_954592.1, NP_954655.1,
NP_955472.1, NP_958831.1, NP_958832.1, NP_958833.1,
NP_958842.1, NP_976217.1, NP_976317.1, NP_976318.1,
NP_976319.1, NP_976320.1, NP_976321.1, NP_976322.1,
NP_976323.1, NP_982257.1, NP_996759.1, NP_997401.1,
NP_997636.1, NP_997637.1, NP_998810.1, NP_998811.1,
XP_005245019.1, XP_005245020.1, XP_005245818.1,
XP_005245821.1, XP_005246799.1, XP_005247711.1,
XP_005247712.1, XP_005248837.1, XP_005248935.1,
XP_005248936.1, XP_005248937.1, XP_005248938.1,
XP_005248939.1, XP_005249832.1, XP_005251108.2,
XP_005251118.1, XP_005251120.1, XP_005251150.1,
XP_005252198.1, XP_005253372.1, XP_005253374.1,
XP_005253751.1, XP_005254140.1, XP_005254592.1,
XP_005255286.1, XP_005255345.1, XP_005256782.1,
XP_005256783.1, XP_005256786.1, XP_005256894.1,
XP_005257452.1, XP_005257650.1, XP_005258235.1,
XP_005258236.1, XP_005259352.1, XP_005259353.1,
XP_005259765.1, XP_005260374.1, XP_005261667.1,
XP_005262022.1, XP_005262166.1, XP_005263411.1,
XP_005263412.1, XP_005263481.1, XP_005264594.1,
XP_005264595.1, XP_005266335.1, XP_005266431.1,
XP_005266785.1, XP_005267487.1, XP_005267488.1,
XP_005268080.1, XP_005268101.1, XP_005268928.1,
XP_005269034.1, XP_005269035.1, XP_005269036.1,
XP_005269108.1, XP_005269109.1, XP_005270425.1,
XP_005273122.2, XP_005273489.1, XP_006712157.1,
XP_006713348.1, XP_006714778.1, XP_006714810.1,
XP_006715825.1, XP_006716058.1, XP_006718761.1,
XP_006719132.1, XP_006720312.1, XP_006720664.1,
XP_006721955.1, XP_006721958.1, XP_006722566.1,
XP_006722796.1, XP_006722797.1, XP_006723449.1,
XP_006723657.1, XP_006724698.1, XP_011507516.1,
XP_011507596.1, XP_011508218.1, XP_011509884.1,
XP_011509885.1, XP_011509886.1, XP_011509887.1,
XP_011511207.1, XP_011511333.1, XP_011512635.1,
XP_011512636.1, XP_011512982.1, XP_011513768.1,
XP_011513776.1, XP_011514530.1, XP_011514531.1,
XP_011514829.1, XP_011514830.1, XP_011515410.1,
XP_011515411.1, XP_011515412.1, XP_011515413.1,
XP_011515414.1, XP_011515415.1, XP_011515416.1,
XP_011515417.1, XP_011515423.1, XP_011515424.1,
XP_011515425.1, XP_011515426.1, XP_011515427.1,
XP_011515571.1, XP_011515945.1, XP_011516666.1,
XP_011516911.1, XP_011517660.1, XP_011517662.1,
XP_011517663.1, XP_011517664.1, XP_011517665.1,
XP_011517666.1, XP_011517667.1, XP_011517668.1,
XP_011517669.1, XP_011517670.1, XP_011518397.1,
XP_011518557.1, XP_011518559.1, XP_011518560.1,
XP_011518561.1, XP_011518562.1, XP_011518563.1,
XP_011518564.1, XP_011518565.1, XP_011518671.1,
XP_011518672.1, XP_011518673.1, XP_011518864.1,
XP_011518865.1, XP_011518866.1, XP_011518867.1,
XP_011518955.1, XP_011519431.1, XP_011519651.1,
XP_011519652.1, XP_011519653.1, XP_011520746.1,
XP_011520772.1, XP_011521840.1, XP_011522642.1,
XP_011523051.1, XP_011523285.1, XP_011523286.1,
XP_011523287.1, XP_011523392.1, XP_011523393.1,
XP_011523420.1, XP_011523421.1, XP_011524058.1,
XP_011524137.1, XP_011524373.1, XP_011524374.1,
XP_011524632.1, XP_011525625.1, XP_011525930.1,
XP_011526077.1, XP_011526078.1, XP_011526258.1,
XP_011526432.1, XP_011526901.1, XP_011526961.1,
XP_011526998.1, XP_011527330.1, XP_011527345.1,
XP_011527346.1, XP_011528499.1, XP_011529190.1,
XP_011529191.1, XP_011529430.1, XP_011530722.1,
XP_011530780.1, XP_011530781.1, XP_011530804.1,
XP_011531399.1, XP_011531802.1, XP_011532297.1,
XP_011532356.1, XP_011532967.1, XP_011533256.1,
XP_011533838.1, XP_011534480.1, XP_011535241.1,
XP_011535435.1, XP_011535437.1, XP_011535438.1,
XP_011535839.1, XP_011536709.1, XP_011536790.1,
XP_011538038.1, XP_011538681.1, XP_011538811.1,
XP_011538812.1, XP_011538813.1, XP_011538814.1,
XP_011538815.1, XP_011538816.1, XP_011538817.1,
XP_011540328.1, XP_011540329.1, XP_011541100.1,
XP_011541173.1, XP_011542487.1, XP_011543594.1,
XP_011543596.1, XP_011544016.1, XP_016855107.1,
XP_016855556.1, XP_016855557.1, XP_016855558.1,
XP_016855559.1, XP_016855560.1, XP_016855561.1,
XP_016855863.1, XP_016855908.1, XP_016856078.1,
XP_016856849.1, XP_016856850.1, XP_016857451.1,

XP_016857452.1, XP_016857453.1, XP_016859432.1, XP_016859433.1, XP_016860119.1, XP_016860205.1, XP_016860206.1, XP_016861020.1, XP_016861021.1, XP_016862507.1, XP_016863624.1, XP_016864342.1, XP_016864523.1, XP_016864524.1, XP_016865852.1, XP_016866306.1, XP_016866307.1, XP_016866433.1, XP_016866833.1, XP_016867171.1, XP_016868009.1, XP_016868678.1, XP_016868682.1, XP_016868683.1, XP_016868684.1, XP_016868685.1, XP_016868686.1, XP_016868687.1, XP_016868735.1, XP_016869028.1, XP_016869029.1, XP_016869030.1, XP_016869031.1, XP_016869032.1, XP_016869033.1, XP_016869034.1, XP_016869035.1, XP_016869036.1, XP_016869037.1, XP_016869038.1, XP_016869039.1, XP_016869040.1, XP_016869047.1, XP_016869048.1, XP_016869049.1, XP_016869050.1, XP_016869051.1, XP_016869299.1, XP_016869300.1, XP_016869434.1, XP_016869469.1, XP_016869596.1, XP_016871328.1, XP_016871329.1, XP_016871330.1, XP_016871651.1, XP_016871652.1, XP_016871819.1, XP_016871820.1, XP_016872103.1, XP_016872104.1, XP_016872455.1, XP_016872709.1, XP_016873415.1, XP_016873595.1, XP_016873596.1, XP_016873887.1, XP_016873940.1, XP_016874003.1, XP_016874004.1, XP_016874335.1, XP_016874336.1, XP_016874847.1, XP_016874957.1, XP_016875508.1, XP_016876293.1, XP_016876959.1, XP_016877101.1, XP_016877103.1, XP_016877116.1, XP_016877117.1, XP_016877118.1, XP_016877200.1, XP_016877579.1, XP_016877580.1, XP_016879883.1, XP_016879884.1, XP_016880112.1, XP_016880169.1, XP_016880170.1, XP_016880171.1, XP_016880188.1, XP_016880189.1, XP_016880190.1, XP_016880354.1, XP_016880355.1, XP_016880356.1, XP_016880360.1, XP_016880361.1, XP_016880362.1, XP_016880363.1, XP_016880364.1, XP_016880365.1, XP_016880435.1, XP_016880436.1, XP_016880437.1, XP_016881168.1, XP_016881582.1, XP_016881587.1, XP_016881588.1, XP_016882418.1, XP_016882662.1, XP_016883197.1, XP_016883198.1, XP_016883528.1, XP_016884292.1, XP_016884293.1, XP_016884294.1, XP_016884295.1, XP_016885269.1, XP_016885270.1, or any combination thereof.

In some embodiments, the preparation of isolated EEV described herein may be obtained after inducing the production of EEV from activated erythrocytes in the blood sample of the subject. Erythrocytes may be activated to induce EEV production, for example, using a calcium ionophore (e.g., A23187), cold-storage, or ATP depletion (Prudent et al., 2015).

In some embodiments, the methods described herein may comprise a step of removing or depleting hemoglobin from a preparation of EEV prior to determining the level of expression of EEV proteins. Given the significant amounts of hemoglobin within erythrocytes that could mask the true nature of the protein signature in EEV, this step may improve the detection of non-hemoglobin EEV proteins. In some embodiments, hemoglobin-depleted and hemoglobin-rich fractions may be prepared in parallel and analyzed separated for expression of EEV proteins (e.g., in mass spectrometry-based proteomic detection techniques).

In some aspects, the methods described herein may further comprise comparing the level of an EEV protein biomarker to a suitable reference value indicative of the presence, stage and/or progression of Parkinson's disease, thereby clinically assessing Parkinson's disease in the subject.

As used herein, the expression "reference value" means a control value or range of values corresponding to a known level or range of an EEV protein biomarker associated with the presence, stage and/or progression of Parkinson's disease. In some embodiments, for example where the expression level of an EEV protein biomarker has previously been measured in a blood sample from a subject, the reference value may be a value corresponding to the same subject's previous reading (e.g., a baseline). The term "suitable" in the expression "suitable reference value" reflects the observations reported herein that the number of EEV (and/or the protein expressed therein) in blood samples from PD subjects may vary depending on, for example, factors which may also affect the EV and/or EEV levels. For example, it is reported herein that a subject's EEV levels may be affected by whether or not the subject is being treated for their PD symptoms, whether the subject has or previously had cancer, whether the subject has or previously had diabetes, or whether the subject is taking anti-inflammatory medication.

In some embodiments, the present description relates to a method for treating a subject with PD, the method comprising clinically assessing Parkinson's disease in the subject by a method described herein, and commencing, administering, and/or modifying PD treatment based on the clinical assessment.

The scope of the claims should not be limited by the particular embodiments set forth in the examples, but should be given the broadest interpretation consistent with the description as a whole

EXAMPLES

Example 1—Methods 1.1 Participant Recruitment and Ethic Statement

Human blood was obtained from two cohorts of participants. The first cohort was composed of Parkinson's disease (PD) patients and healthy age- and sex-matched Controls, and the second cohort was composed of Huntington's disease (HD) patients and healthy age- and sex-matched Controls. The demographics for both cohorts are shown in Table 1. For the two cohorts, the Controls were recruited amongst the caregivers, spouses, family and friends of the patients. Institutional review boards approved this study (CHU de Québec-Université Laval, #A13-2-1096; CHUM, #14.228; Cambridge Central Regional Ethics Committee, REC #03/303 & #08/H0306/26; and Cambridge University Hospitals Foundation Trust Research and Development department, R&D #A085170 & A091246) in accordance with the Declaration of Helsinki, and written informed consent was obtained from all participants.

In the case of PD patients, the clinical evaluation included measures on the Unified Parkinson Disease Rating Scale (UPDRS), the Hoehn and Yahr (H&Y) stage, the Mini Mental State Examination (MMSE), the Addenbrooke's Cognitive Examination (ACE), and the Beck Depression Inventory (BDI). In the case of the HD patients, we collected their scores on the Unified Huntington Disease Rating Scale (UPDRS), Total Functional capacity (TFC) and calculated values for burden of disease (BDS). All the clinical evaluations were conducted within 9 months of the blood drive. Participants were further asked to fill out a questionnaire related to health issues and medication and their full blood count performed on the day of blood sampling.

Of note, participants excluded from the present EEV-related analyses included those with diabetes and those suffering or having suffered from cancer, because we observed a significant PD-independent increase in EEV concentration in the platelet-free plasma of these participants. Furthermore, PFP samples with elevated free hemoglobin (>45 000 ng/mL), potentially due to hemolysis at blood sampling, were also excluded from EEV-related analyses, which explains the discrepancies between the total number of participants initially recruited and those contained in each analysis.

For all experiments, diluted annexin-V buffer (BD Pharmingen, Mississauga, ON, Canada) and phosphate buffered saline (PBS) were filtered on 0.22 μm pore size membranes. To quantify the EV according to their cell of origin, the following surface markers were used: CD235a+ (erythrocytes) (5 μL), CD31+/CD41− (endothelial cells) (1 μL), CD41+ (platelets) (5 μL), CD45+ (leukocytes) (3 μL),

TABLE 1

Participant demographics
Table 1: Participant clinical information.

Parkinson's disease (PD) cohort

| | | PD Patients - Stages of disease | | | | |
|---|---|---|---|---|---|---|
| | Ctrl | Unknown | Mild | Moderate | Severe | P value |
| n | 37 | 7 | 12 | 33 | 8 | |
| Age | 66.8 | 69.8 | 66.7 | 71.1 | 75.0* | 0.04 |
| Gender F (M) | 18 (19) | 1 (6) | 6 (6) | 16 (17) | 0 (8) | 0.05 |
| | | | Disease severity | | | |
| Hoehn & Yahr (n) | | | 1 ± 0.3 (12) | 2 ± 0.2 (33) | 3 ± 0.5 (8) | <0.0001 |
| UPDRS (n) | | | 38 ± 11 (6) | 52 ± 19 (17) | 73 ± 20 (6) | 0.02 |
| ACE (n) | | | 96 ± 4 (6) | 92 ± 7 (17) | 84 ± 14 (6) | 0.13 |
| MMSE (n) | | | 29 ± 2 (7) | 29 ± 1 (19) | 26 ± 3 (6) | 0.01 |
| BDI (n) | | | 3 ± 2 (6) | 4 ± 2 (17) | 13 ± 7 (4) | 0.03 |
| | | | Comorbidities | | | |
| Asthma | 3 | 1 | 1 | 5 | 0 | 0.71 |
| Hypertension | 10 | 1 | 2 | 10 | 3 | 0.76 |
| Diabetes | 2 | 0 | 0 | 1 | 2 | 0.10 |
| Cancer | 5 | 0 | 3 | 4 | 1 | 0.64 |
| Allergies | 2 | 0 | 2 | 6 | 2 | 0.28 |
| Depression | 3 | 1 | 2 | 1 | 2 | 0.29 |
| Hypercholesterolemia | 5 | 0 | 1 | 6 | 1 | 0.73 |

Huntington's disease (HD) cohort

| | | HD Patients - Stages of disease | | | | | | |
|---|---|---|---|---|---|---|---|---|
| | Ctrl | Pre-HD | Stage 1 | Stage 2 | Stage 3 | Stage 4 | Stage 5 | P value |
| n | 55 | 11 | 15 | 13 | 12 | 10 | 2 | |
| Age | 55.0 | 37.5 | 53.1 | 54.2 | 58.3 | 58.1 | 55.5 | 0.02 |
| Gender F (M) | 31 (22) | 6 (5) | 5 (10) | 4 (9) | 8 (4) | 7 (3) | 1 (1) | 0.26 |
| | | | | Disease severity | | | | |
| UHDRS (n) | | 2.7 (11) | 15.7 (14) | 34.5 (11) | 42.9 (12) | 55.9 (10) | 67.5 (2) | <0.001 |
| TFC (n) | 13 (16) | 13 (11) | 12.5 (13) | 7.8 (13) | 4.3 (12) | 1.6 (10) | 0 (2) | <0.001 |
| CAG (n) | 28.3 (3) | 41.1 (10) | 42.3 (13) | 42.6 (12) | 43.7 (7) | 44.3 (7) | | <0.001 |
| BDS (n) | | 206 (10) | 337 (13) | 356 (12) | 442 (7) | 465 (7) | | <0.001 |
| | | | | Comorbidities | | | | |
| Asthma | 0 | 0 | 1 | 0 | 0 | 0 | 0 | 0.65 |
| Hypertension | 4 | 1 | 2 | 1 | 1 | 2 | 0 | 0.92 |
| Diabetes | 3 | 1 | 1 | 1 | 1 | 1 | 0 | 0.99 |
| Cancer | 0 | 0 | 0 | 0 | 0 | 0 | 0 | |
| Allergies | 3 | 0 | 2 | 2 | 0 | 0 | 0 | 0.33 |
| Depression | 8 | 1 | 1 | 3 | 6 | 4 | 1 | 0.0497 |
| Hypercholesterolemia | 8 | 1 | 1 | 0 | 0 | 1 | 0 | 0.32 |

(PD cohort) Disease severity levels in relation to the H&Y scale (score): Mild (1-1.5); Moderate (2-2.5); Severe (3-3.5).
*p < 0.05 vs. CTRL. Statistical analyses were performed using a Welch ANOVA followed by Dunnett's multiple comparison test. Disease severity was evaluated within 6 months of blood sampling. Comorbidities were determined from medical information reported by the participant or caregiver. Cancer refers to participant having suffered from cancer in the past. (HD cohort) Disease severity levels in relation to the TFC scale: Stage 1 (11-13); Stage 2 (7-10); Stage 3 (3-6); Stage 4 (1-2); Stage 5 (0). Disease severity was evaluated within 6 months of blood sampling. Comorbidities were determined from medical information reported by the participant or caregiver. Abbreviations: ACE, Addenbrooke's cognitive examination; BDI, Beck depression inventory; BDS, Burden of Disease Score; CAG, Trinucleotide repeat; MMSE, Mini-Mental State Examination; UHDRS, Unified Huntington's Disease Rating Scale; TFC, Total Function Capacity.

1.2 Preparation of Platelet-Free Plasma (PFP) and Extracellular Vesicle (EV) Labeling Citrated blood was centrifuged twice for 15 minutes at 2500 g at room temperature. Platelet-free plasma (PFP) was harvested and stored at −80° C. within 2 hours of collection following guidelines suggested by Lacroix and colleagues (Lacroix et al., 2012).

CD45+CD14+ (monocytes) (10 μL), and CD45+CD15+ (granulocytes) (2 μL), with or without annexin-V staining (5 μL). PFP (5 μL) was incubated with Phenylalanyl-prolyl-arginyl Chloromethyl Ketone (PPACK) (Calbiochem, Etobicoke, ON, Canada) for 5 minutes, followed by a 30-minute incubation with antibodies and annexin-V in a final PBS volume of 100 μL, all at room temperature. Finally, the samples were diluted to a final volume of 2 mL prior to FACS analysis. The following antibodies were purchased at BD Pharmingen and used throughout the experiments: FITC-conjugated mouse anti-human CD235a (clone GA-R2 (HIR2), 1/20), PE-conjugated mouse anti-human CD31 (clone WM59, 1/100), V450-conjugated mouse anti-human CD41a (clone HIPS, 1/20), APC mouse anti-human CD14 (clone M5E2, 1/10), PE-conjugated mouse anti-human CD15 (clone H198, 1/50), V450-conjugated mouse anti-human CD45 (clone H130, 1/33), V450- and PerCP-Cy™5.5-conjugated annexin-V (1/33 and 1/10, respectively).

1.3 Flow Cytometry Quantification

For EV quantification, we used a FACS Canto II Special Order Research Product equipped with a forward scatter (FSC) coupled to a photomultiplier tube (FSC-PMT). Flow cytometer performance tracking was carried out daily using the BD cytometer setup and tracking beads (BD Biosciences, San Jose, CA, USA). The size of the EV was determined using fluorescent silicone beads of 100, 500 and 1000 nm. Controls and optimization of the detection method are presented in FIGS. 1A-1F. The settings for the EV detection were determined as described previously (Rousseau et al., 2015) using a threshold of 200 for SSC. Between PD and HD analyses, the blue laser had to be replaced for maintenance issues and therefore laser settings were reassessed. For FSC-PMT, the assigned voltage was 363 (PD) and 160 (HD) Volts. For SSC, the assigned voltage was 407 (PD) and 300 (HD) Volts. All other parameters were set between 450 and 500 Volts. The acquisition of EV was performed at low speed with an approximate rate of 10 µL/min. To determine background noise level, antibody mixes were incubated in absence of PFP sample and unlabeled PFP was used as a negative control.

1.4 Statistical Analyses

All statistical analyses pertaining to Examples 2.1 and 2.2 were performed using "The Statistics and Machine Learning Toolbox" provided by MathWorks™ under the MATLAB™ platform. The version used was MATLAB® R2015a. The analysis included the scatter plot, the classical least-squares linear regression model, the R-squared and p values, as well as Pearson's goodness-of-fit model. Interval cut-off values were determined using a loop program developed in MATLAB™. Model diagnostics, including residual behaviour and homoscedastivity, were also obtained with the same Toolbox.

1.5 Production and Purification of EEV

Blood was collected in heparin tubes and centrifuged for 10 minutes at 282 g at room temperature. Blood cells were washed first in PBS-2% FBS, then with 0.9% sodium chloride solution and centrifuged for 10 minutes at 750 g. To avoid leukocyte and/or platelet contamination, the buffy coat and the upper fraction of erythrocytes were removed. To preserve erythrocytes, two volumes of glycerolyte 57 solution (57% glycerol, 142 mM sodium lactate, 1 mM KCl, 25 mM sodium phosphate pH 6.8) were added to the pellet and stored at −80° C.

For the production of EEV, red bloods cells were thawed and EV production was induced as previously described (Minetti et al., 2004). Briefly, the erythrocyte pellet was activated with 3 volumes of calcium ionophore solution (150 mM NaCl; 10 mM Tris-HCl; 1 mM $CaCl_2$; 5 µM ionophore A23187 (Sigma, St Louis, MO)) for 30 minutes at 37° C. The activation was stopped by the addition of 5 mM EDTA. Remaining erythrocytes were pelleted at 15 000 g for 20 minutes. The EEV were centrifuged at 20 000 g for 90 minutes and washed once in PBS. The EEV pellet was resuspended in PBS and frozen at −80° C. until further analyses.

1.6 C-Reactive Protein, Free Hemoglobin and α-Synuclein Quantification

The concentrations of C-reactive protein (CRP) and free hemoglobin were determined in the PFP of all donors using the RayBio™ Human CRP ELISA Kit (RayBiotech, Norcross, GA, USA) and the Hemoglobin Human ELISA kit (Abcam, Toronto, ON, Canada). To quantify α-synuclein (α-Syn) in erythrocytes and EEV, we used the human α-Syn ELISA kit (ThermoFisher Scientific, Waltham, MA, USA). Absorbance values were measured at 450 nm using a multi-detection microplate reader (Synergy HT; BioTek; Winooski, VT, USA). All ELISA tests were performed according to the manufacturer's instructions.

1.7 Scanning Electron Microscopy

Preparations of erythrocytes (5 µL) were fixed in 2% paraformaldehyde and 2.5% glutaraldehyde in PBS buffer at least 24 hours before standard dehydration. Samples were washed 3 times for 10 minutes with sodium cacodylate buffer (0.1 M, pH 7.3) and fixed with 1% osmium tetroxide in sodium cacodylate buffer for 90 minutes. Subsequently, samples were washed and processed in 50%, 70%, 90% and 100% ethanol for dehydration (10 minutes/step). Finally, samples were soaked in two subsequent baths of 100% ethanol, for 40 minutes and 10 minutes, air-dried overnight and coated with palladium. Observations were completed using a JEOL 6360LV scanning electron microscope (JEOL, Peabody, MA, USA).

1.8 Transmission Electron Microscopy

Preparations of EEV (30 µL) and activated erythrocytes (5 µL) were fixed in 2% paraformaldehyde at least 24 hours before being dehydrated and sealed in LR white resin. Slices of LR white resin were placed on a Formvar/carbon-coated grid and processed for immunolabeling. The tissues mounted on grids were blocked in 0.5% BSA-c (Aurion, Wageningen, The Netherlands) in HBSS and incubated for 120 minutes with rabbit anti-α-Syn antibody (Abcam, Toronto, ON, Canada) or rabbit anti-α-Syn (phospho S129) antibody (Abcam, Toronto, ON, Canada), both diluted at 1:250 in HBSS and washed several times with distilled water. Finally, the grids were incubated for 60 minutes with an anti-rabbit IgG conjugated to 6 nm gold particles (EMS, Hatfield, PA, USA) diluted at 1:200 and washed several times with distilled water to ultimately be fixed in 2.5% glutaraldehyde (EMS, Hatfield, PA, USA) in HBSS for 15 minutes. For this last step, the grids were treated with 3% uranyl acetate-0.075 M oxalate (pH 7.0) (EMS, Hatfield, PA, USA) for 1 minute, which was followed by several washes in distilled water. Observations were completed with a TECNAI Spirit G2 transmission electron microscope at 80 kV (FEI, Hillsboro, OR, USA).

1.9 Mass Spectrometry Analysis and Label Free Protein Quantification

For proteomic analyses, EEV from 4 individuals per group (Control, mild PD and moderate PD) were prepared as described above. For each individual, 25 µg of protein sample, according to Bradford protein assay, were migrated onto an electrophoresis gel 4-12% Bis-Tris to separate hemoglobin from higher proteins. Following gel staining using Sypro Ruby (Thermo Fischer Scientific), the 12 kDa band corresponding to the hemoglobin size was cut out and the remaining part of the gel further fractioned into 7 slices, exposed to trypsin digestion and peptide extraction on a MassPrep™ liquid handling robot (Waters, Milford, USA) according to the manufacturer's specifications and to the protocol of Shevchenko et al., 1996, with the modifications suggested by Havlis et al., 2003. The extracted peptides from the 7 slices of the same individual were pooled and analyzed by nanoLC-MS/MS. The excised hemoglobin gel slices were also analyzed in the same conditions. One µg of each individual sample was injected on a Dionex Ulti-Mate™ 3000 nanoRSLC system (Thermo Scientific) equipped with a nanoviper Acclaim Pepmap100™, C18, 3 µm, 75 µm×column (Thermo Scientific) connected to the nanoelectrospray source of an Orbitrap Fusion™ mass spectrometer (Thermo Scientific). The peptides were eluted at 300 nL/min using an acetonitrile gradient of 90 minutes and the mass spectrometer was operating in Data Dependent Acquisition mode. Peptide masses were measured in MS spectra detected in the orbitrap at 120K resolution. MSMS fragmentation spectra of peptides were generated by Higher energy Collisional Dissociation (HCD) and detected in the ion trap. Spectra were searched against a human protein database (Uniprot Complete Proteome, taxonomy *Homo sapiens*—83512 sequences) using Andromeda™ search engine included in MaxQuan™ software version 1.5.5.1 (Cox et al., 2008). MaxQuant™ was also used to validate proteins and peptides at 1% False Discovery Rate using a target/decoy database search and to perform Label Free Quantification of the identified proteins using the 'match between runs' option.

1.10 Further Statistical Analyses

Figure 3A:
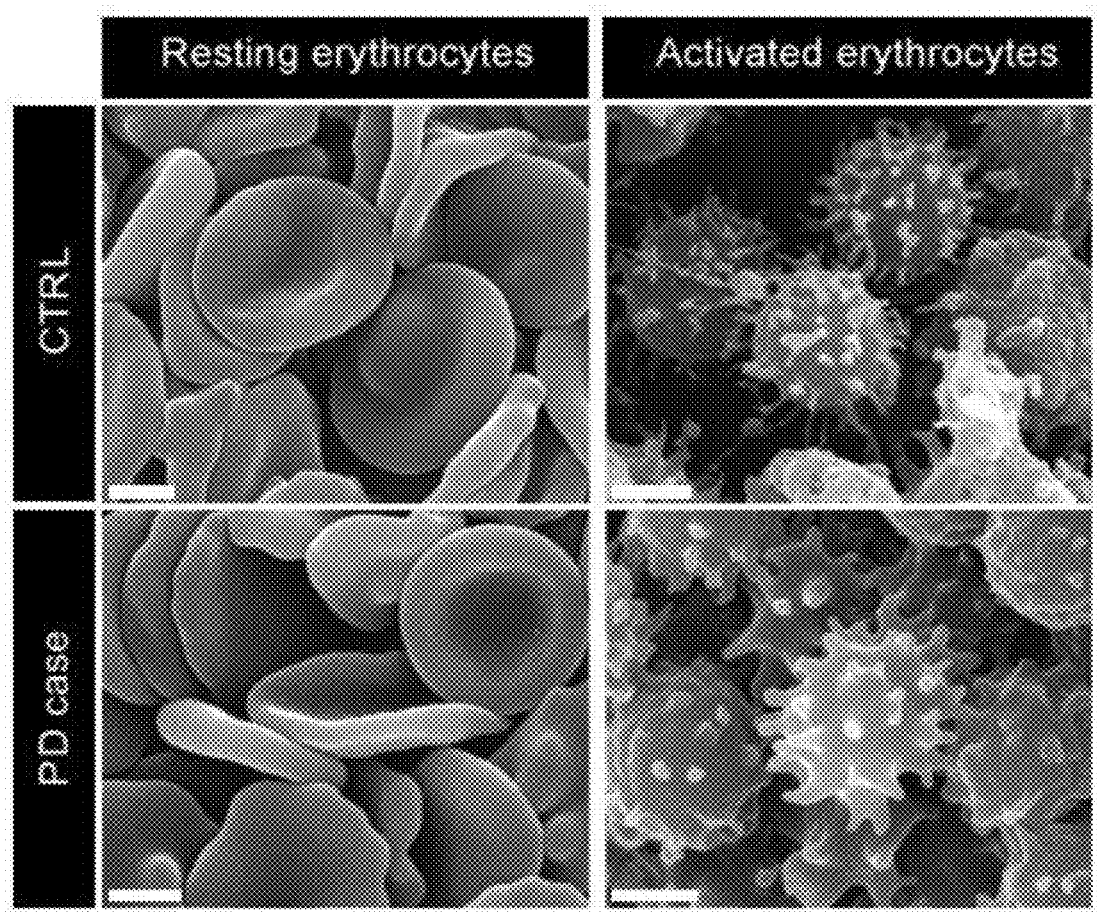
FIGS. 3A and 3B. Detection of normal and phosphorylated α-Syn in EEV.
Figure 3B:
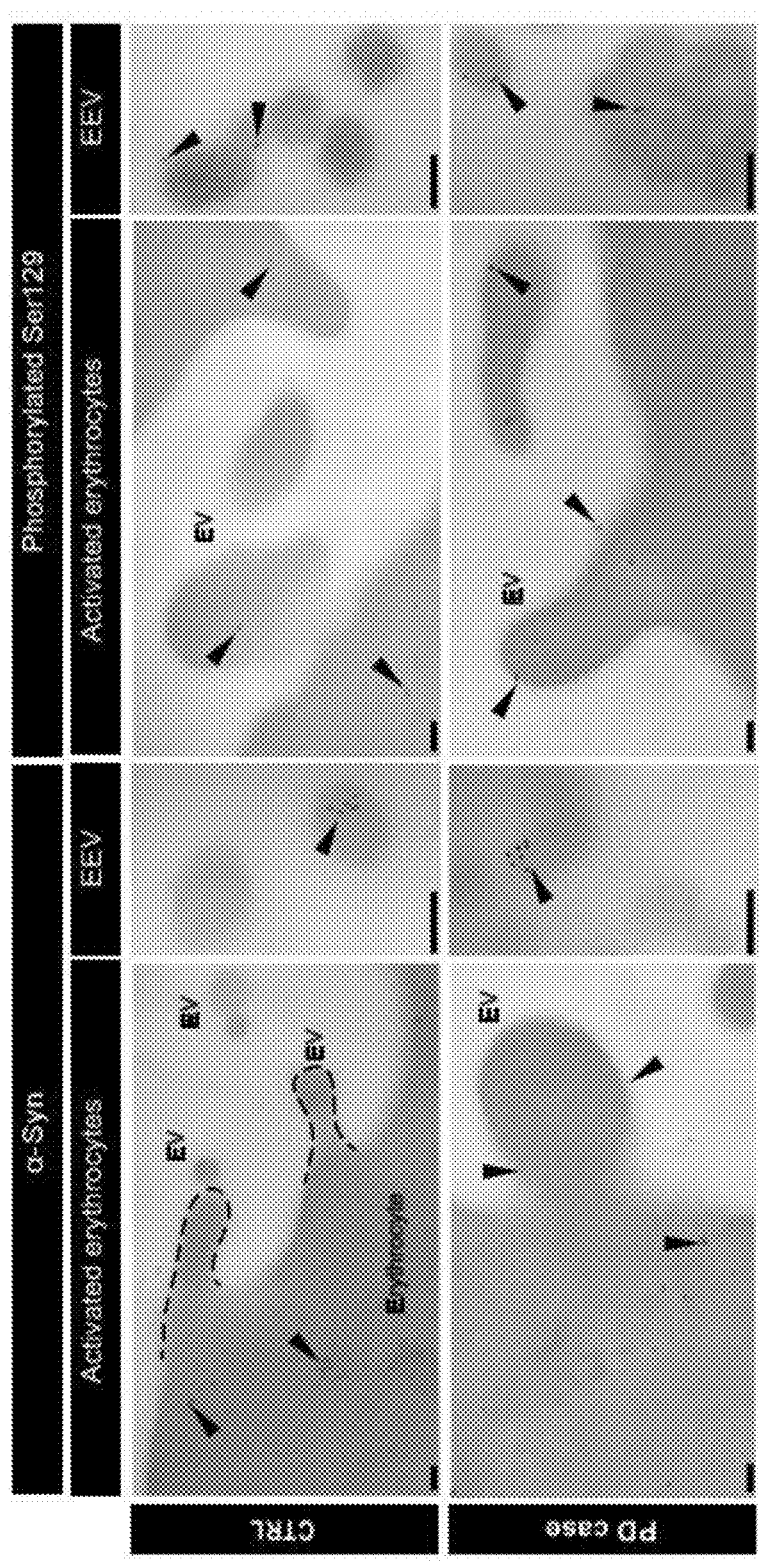
Figure 3C:
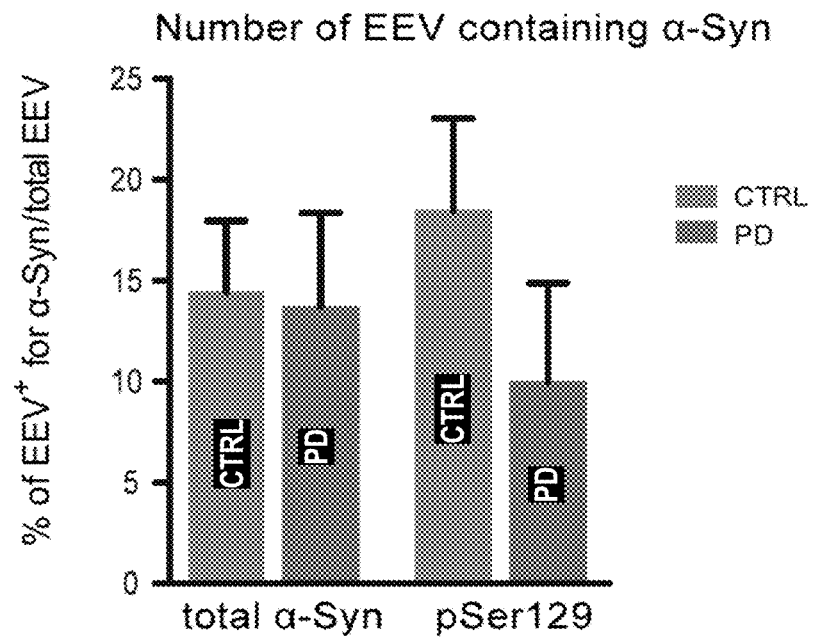
FIG. 3C: Quantification of α-Syn in EEV as detected by transmission electron microscopy and expressed as the percentage of EEVs positive for α-Syn/total number of EEV in healthy sex- and age-matched CTRL and PD patients (n=100 erythrocytes sampled in n=3 CTRL and n=3 PD).
Figure 3D:
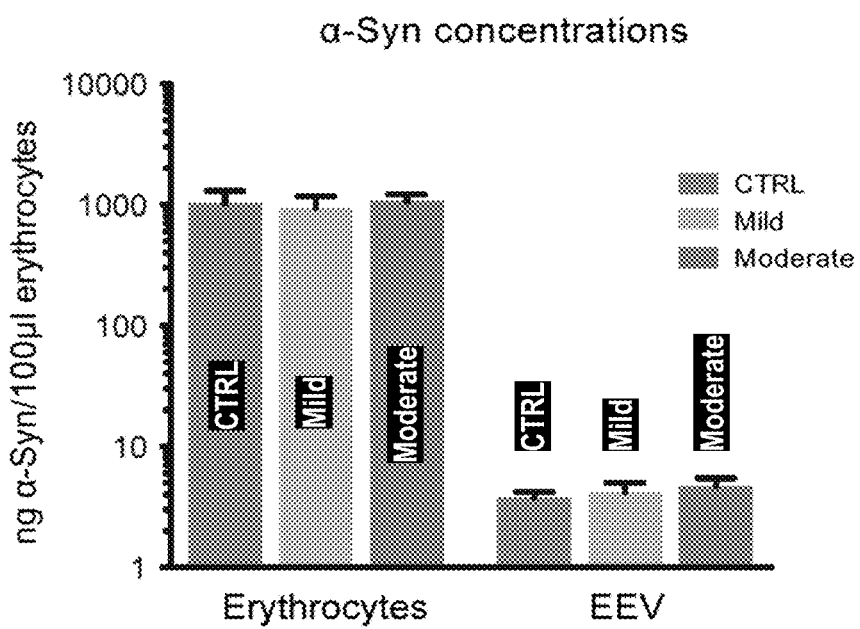
FIG. 3D: Quantification of α-Syn in EEV by ELISA assay in healthy sex- and age-matched CTRL, mild and moderate stage patients selected according to their H&Y stage (n=4 erythrocytes per group; n=13 EEV per group) revealing the absence of measurable changes in α-Syn levels between PD and healthy sex- and age-matched CTRL. Statistical analyses were performed using a Mann-Whitney U test (FIG. 3C) or a Kruskal-Wallis ANOVA (FIG. 3D). Abbreviations: α-Syn, α-synuclein; α-Syn pS129, α-synuclein phosphorylated Serine 129; CTRL, Control; EEV, erythrocyte-derived extracellular vesicle; H&Y, Hoehn and Yahr; PD, Parkinson's disease.

For FIGS. 3C and 3D, data were first tested for normality using the D'Agostino & Pearson normality test. Comparisons between groups were obtained by Mann-Whitney U test or Kruskal-Wallis ANOVA and performed using Prism 6.0 (GraphPad Software, LaJolla, CA). For analyses displayed in FIG. 4C, the 'Intensity values' contained in the output 'proteingroup.txt' file of MaxQuant™ were used to quantify each identified protein in each individual sample. The values were normalized by the median of each column (all intensity values of proteins for one sample). The missing values were imputed with a noise value corresponding to the 1-percentile of each sample column. For each comparison between two groups (Control, mild PD or moderate PD), proteins with too many imputed values where considered not quantifiable (a minimum of three not-imputed values in one of the 2 groups are required). A protein ratio was calculated between the two groups using the average of intensity values in each group. Finally, a statistical Welch's test was performed between the two groups. The protein ratios were transformed into log 2(ratio) then centered by calculation of a z-score ($z\text{-score}=(x-\mu)/\sigma$). A protein was considered as variant if it fulfilled the following criteria: minimum of 2 peptides quantified, Welch's test p value<0.05 and absolute value of z-score>1.96 (corresponding to values outside of the 95% confidence interval). The Gene Ontology enrichment analysis on the identified proteins (FIG. 4D) was performed on the Cytoscape™ platform (v. 3.4.0) using the BinGO™ software version 3.0.3 (Maere et al., 20005) against all human genes with GO annotation (Uniprot-GOA generated 2015-06-22). Enrichment was calculated by hypergeometric test and Bonferroni Family-Wise Error Rate (FWER) was used to correct for multiple testing. The data for the resulting 8 proteins was standardized, hierarchically clustered and visualized as a heatmap by using the statistical framework R (R Core Team, 2016). The robustness of the nodes was evaluated by computing Approximately Unbiased (AU) p values using the R package pvclust (10000 bootstraps, average method and correlation-based dissimilarity matrix) (Suzuki et al., 2006).

Example 2—Results

The cohorts studied here included Parkinson's disease (PD) (n=60) and Huntington's disease (HD) patients (n=63) of all stages (see Example 1.1), as well as their respective age- and sex-matched healthy controls (n=37; n=55, respectively). The demographics for both cohorts are shown in Table 1. Full blood counts (erythrocytes, lymphocytes, platelets, leukocytes, monocytes, neutrophils) and C-reactive protein (indicative of an inflammatory response) quantification were obtained for all participants, but they did not reveal any significant differences between groups (data not shown). Similarly, the hematocrit, the mean corpuscular hemoglobin, as well as the mean corpuscular volume values were similar between PD and control groups (data not shown).

2.1 PD Patients Exhibit a Disease-Specific Increase in Erythrocyte-Derived EV

Platelet-free plasma (PFP) and extracellular vesicles (EV) were labeled and quantified according to their cell of origin for all participants, as described in Examples 1.2 and 1.3. Results are summarized in Table 2A (PD patients and controls) and Table 2B (HD patients and controls).

As shown in Table 2A, no significant differences between PD patient and control samples were observed in the number of EV originating from platelets, endothelial cells, monocytes, granulocytes, and leukocytes. Similarly, as shown in Table 2B, no significant differences between HD patient and control samples were observed in the concentrations of EV originating from these same cell types.

Interestingly, a significant increase in erythrocyte-derived EV in patients with PD was observed, as compared to the control group (see values highlighted in black in Table 2A). This increase in erythrocyte-derived EV in patients with PD was disease-specific, as the same effect was not observed in erythrocyte-derived EV in patients with HD (Table 2B).

TABLE 2A

Quantification of extracellular vesicles (EV) derived from different cell types of PD patients and controls

| Cell type | Markers | Units | CTRL | | | PD | | | P value |
|---|---|---|---|---|---|---|---|---|---|
| | | | n | Mean | SEM | n | Mean | SEM | |
| Platelets | CD41+PS− | $\times 10^3/\mu L$ | 37 | 7.88 | 1.68 | 59 | 10.3 | 1.33 | 0.27 |
| | CD41+PS+ | | 37 | 15.2 | 3.20 | 59 | 17.9 | 2.53 | 0.51 |
| | CD41+CD31+ | | 37 | 1.51 | 0.69 | 59 | 1.99 | 0.54 | 0.59 |
| | CD41+ total | | 37 | 23.1 | 4.62 | 59 | 28.2 | 3.66 | 0.38 |
| | EV CD41+/platelet | | 35 | 0.106 | 0.021 | 57 | 0.125 | 0.016 | 0.49 |
| Endothelial cells | CD31+CD41−PS− | $\times 10^3/\mu L$ | 37 | 15.8 | 8.04 | 59 | 11.7 | 6.37 | 0.75 |
| | CD31+CD41−PS+ | | 37 | 0.91 | 0.13 | 59 | 0.92 | 0.10 | 0.96 |
| | CD31+CD41− total | | 37 | 16.7 | 8.03 | 59 | 12.6 | 6.36 | 0.75 |

TABLE 2A-continued

Quantification of extracellular vesicles (EV) derived
from different cell types of PD patients and controls

| Cell type | Markers | Units | CTRL n | CTRL Mean | CTRL SEM | PD n | PD Mean | PD SEM | P value |
|---|---|---|---|---|---|---|---|---|---|
| Monocytes | CD45−CD14+ PS− | ×10³/μL | 37 | 1.70 | 0.30 | 59 | 1.62 | 0.24 | 0.85 |
| | CD45−CD14+ PS+ | | 37 | 1.20 | 4.00 | 59 | 5.84 | 3.17 | 0.50 |
| | CD45+CD14+ PS− | | 37 | 0.16 | 0.04 | 59 | 0.14 | 0.03 | 0.74 |
| | CD45+CD14+PS+ | | 37 | 0.60 | 0.79 | 59 | 1.47 | 0.63 | 0.59 |
| | CD14+ total | | 37 | 3.66 | 4.88 | 59 | 9.06 | 3.87 | 0.60 |
| | EV CD14+/monocyte | | 35 | 7.08 | 1.99 | 57 | 9.16 | 1.56 | 0.41 |
| Granulocytes | CD45−CD15+ PS− | ×10³/μL | 37 | 12.3 | 7.96 | 59 | 16.7 | 6.30 | 0.92 |
| | CD45−CD15+ PS+ | | 37 | 2.21 | 0.77 | 59 | 1.39 | 0.61 | 0.47 |
| | CD45+CD15+ PS− | | 37 | 0.55 | 0.36 | 59 | 1.15 | 0.29 | 0.20 |
| | CD45+CD15+PS+ | | 37 | 1.01 | 0.30 | 59 | 1.25 | 0.24 | 0.56 |
| | CD15+ total | | 37 | 16.0 | 8.83 | 59 | 20.6 | 6.99 | 0.91 |
| | EV CD15+/granulocyte | | 35 | 3.70 | 0.64 | 57 | 3.16 | 0.50 | 0.53 |
| Leukocytes | CD45+ total | ×10³/μL | 37 | 10.4 | 2.21 | 59 | 13.8 | 1.75 | 0.26 |
| Erythrocytes | CD235a+PS− | ×10³/μL | 36 | 18.2 | 46.5 | 59 | 32.0 | 36.3 | 0.04 |
| | CD235a+PS+ | | 36 | 0.22 | 0.07 | 59 | 0.29 | 0.05 | 0.70 |
| | CD235a+ total | | 36 | 18.4 | 47.0 | 59 | 32.3 | 36.7 | 0.04 |
| | EV CD235a+/erythrocyte | | 34 | 0.0039 | 0.011 | 57 | 0.0069 | 0.008 | 0.04 |

Abbreviations: CD235a, glycophorin A; EV, extracellular vesicle; PD, Parkinson's disease; PS, phosphatidylserine.

TABLE 2B

Quantification of extracellular vesicles (EV) derived from different cell types of HD patients and controls

| Cell type | Markers | Units | CTRL n | CTRL Mean | CTRL SEM | HD pre-manifest n | HD pre-manifest Mean | HD pre-manifest SEM | HD n | HD Mean | HD SEM | P value |
|---|---|---|---|---|---|---|---|---|---|---|---|---|
| Platelets | CD41+PS− | ×10³/μL | 54 | 9.2 | 2.2 | 10 | 4.3 | 1.3 | 50 | 6.1 | 1.0 | 0.78 |
| | CD41+PS+ | | 54 | 19.3 | 4.8 | 10 | 7.1 | 2.0 | 50 | 12.4 | 2.4 | 0.74 |
| | CD41+ total | | 54 | 28.4 | 6.9 | 10 | 11.4 | 3.2 | 50 | 18.6 | 3.4 | 0.70 |
| | EV CD41+/platelet | | 53 | 0.12 | 0.03 | 10 | 0.05 | 0.02 | 48 | 0.08 | 0.01 | 0.34 |
| Endothelial cells | CD31+CD41−PS− | ×10³/μL | 54 | 1.4 | 0.3 | 10 | 0.6 | 0.2 | 50 | 1.2 | 0.2 | 0.31 |
| | CD31+CD41−PS+ | | 54 | 0.68 | 0.16 | 10 | 0.25 | 0.06 | 50 | 0.46 | 0.09 | 0.59 |
| | CD31+CD41− total | | 54 | 2.1 | 0.4 | 10 | 0.8 | 0.2 | 50 | 1.7 | 0.3 | 0.26 |
| Monocytes | CD45−CD14+ PS− | ×10³/μL | 54 | 3.4 | 1.1 | 10 | 1.6 | 0.2 | 51 | 1.6 | 0.1 | 0.91 |
| | CD45−CD14+ PS+ | | 54 | 1.8 | 0.3 | 10 | 0.8 | 0.3 | 51 | 1.5 | 0.2 | 0.14 |
| | CD45+CD14+ PS− | | 54 | 0.18 | 0.07 | 10 | 0.069 | 0.016 | 51 | 0.056 | 0.008 | 0.34 |
| | CD45+CD14+PS+ | | 54 | 0.62 | 0.12 | 10 | 0.24 | 0.06 | 51 | 0.55 | 0.14 | 0.12 |
| | CD14+ total | | 54 | 6.0 | 1.3 | 10 | 2.6 | 0.4 | 51 | 3.7 | 0.4 | 0.08 |
| | EV CD14+/monocyte | | 53 | 12.3 | 2.5 | 10 | 5.7 | 0.6 | 48 | 8.0 | 1.0 | 0.13 |
| Granulocytes | CD45−CD15+ PS− | ×10³/μL | 54 | 1.2 | 0.1 | 10 | 1.2 | 0.3 | 51 | 1.5 | 0.2 | 0.33 |
| | CD45−CD15+ PS+ | | 54 | 0.12 | 0.04 | 10 | 0.18 | 0.08 | 51 | 0.22 | 0.11 | 0.33 |
| | CD45+CD15+ PS− | | 54 | 0.20 | 0.05 | 10 | 0.07 | 0.02 | 51 | 0.15 | 0.04 | 0.64 |
| | CD45+CD15+PS+ | | 54 | 0.25 | 0.05 | 10 | 0.13 | 0.06 | 51 | 0.20 | 0.04 | 0.39 |
| | CD15+ total | | 54 | 1.7 | 0.2 | 10 | 1.6 | 0.4 | 51 | 0.20 | 0.3 | 0.67 |
| | EV CD15+/granulocyte | | 53 | 0.41 | 0.04 | 10 | 0.42 | 0.13 | 48 | 0.50 | 0.08 | 0.75 |
| Leukocytes | CD45+ total | ×10³/μL | 54 | 33.4 | 2.7 | 10 | 31.6 | 5.3 | 51 | 31.7 | 2.4 | 0.88 |
| Erythrocytes | CD235a+PS− | ×10³/μL | 54 | 15.2 | 2.0 | 10 | 10.3 | 3.5 | 51 | 14.1 | 1.4 | 0.16 |
| | CD235a+PS+ | | 54 | 1.1 | 0.2 | 10 | 0.4 | 0.2 | 51 | 1.1 | 0.1 | 0.04 |
| | CD235a+ total | | 54 | 16.4 | 2.0 | 10 | 10.7 | 3.5 | 51 | 15.3 | 1.5 | 0.09 |
| | EV CD235a+/erythrocyte | | 54 | 0.0035 | 0.0005 | 10 | 0.0023 | 0.0008 | 50 | 0.0033 | 0.0003 | 0.11 |

Abbreviations: CD235a, glycophorin A; EV, extracellular vesicle; HD, Huntington's disease; PS, phosphatidylserine.

Figure 1A:
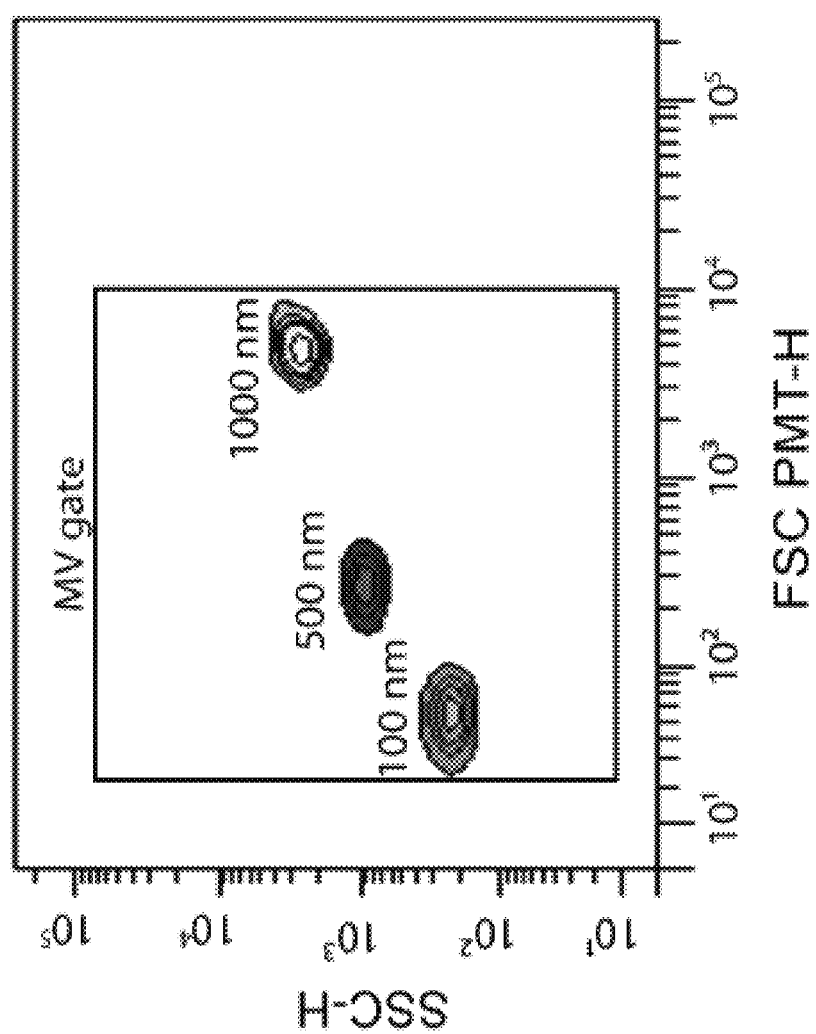
Figure 1B:
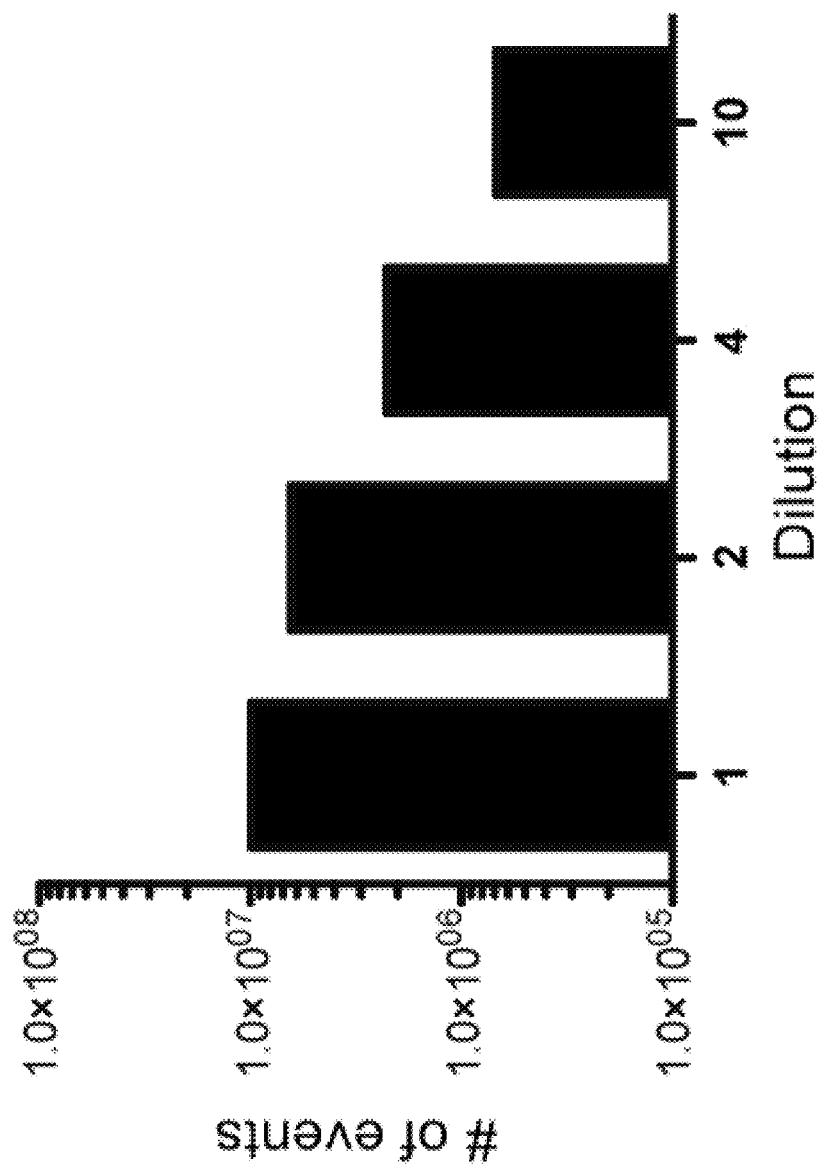
Figure 1C:
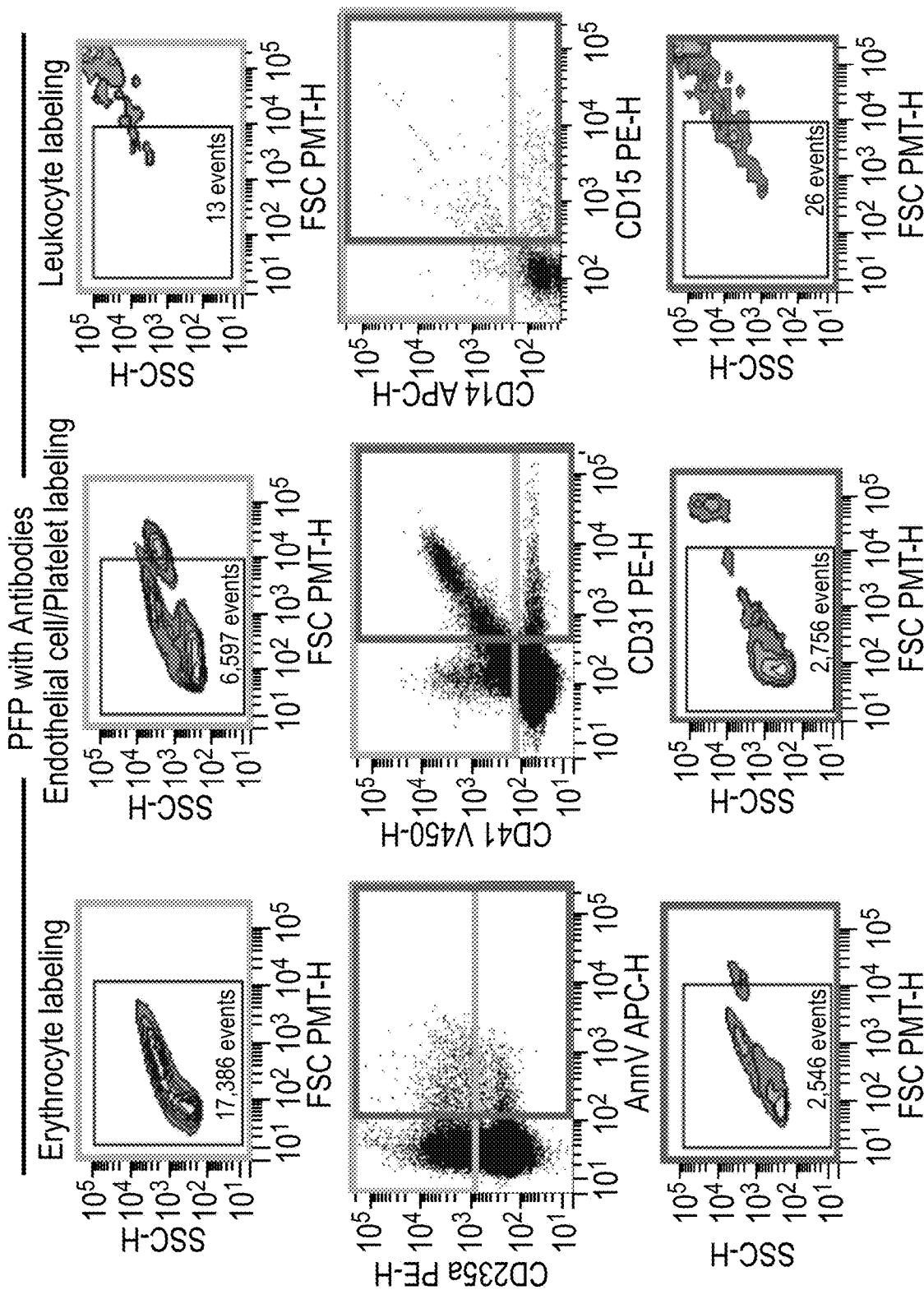
Figure 1D:
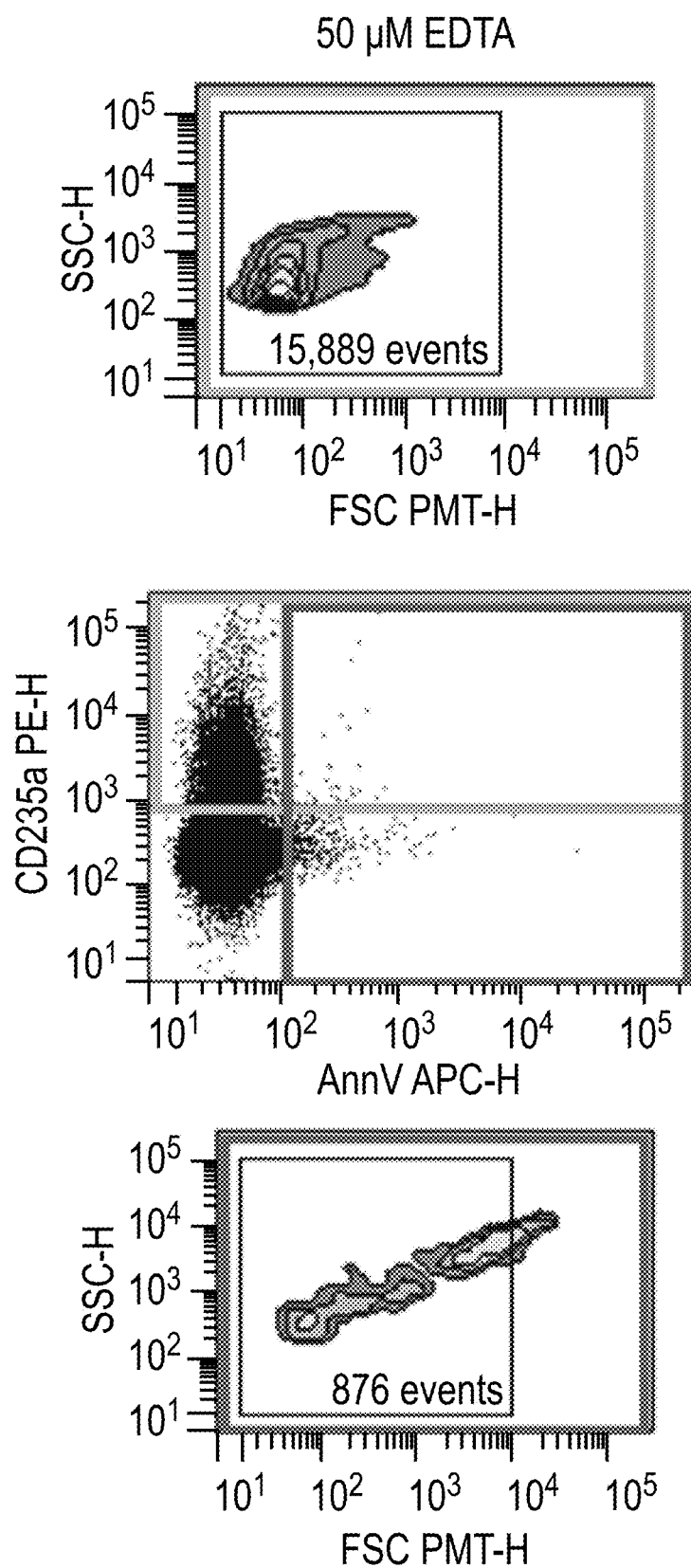
Figure 1E:
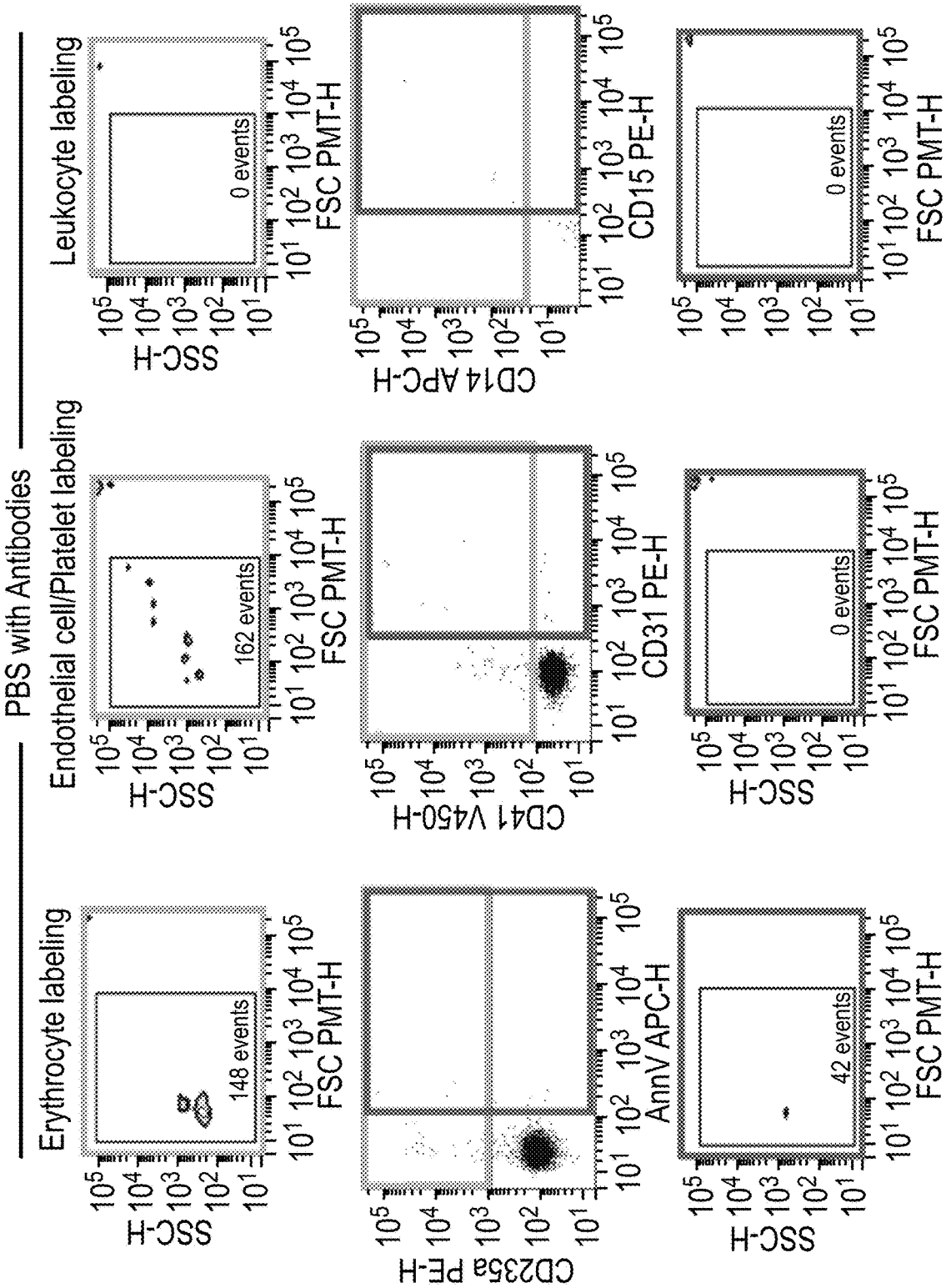
Figure 2A:
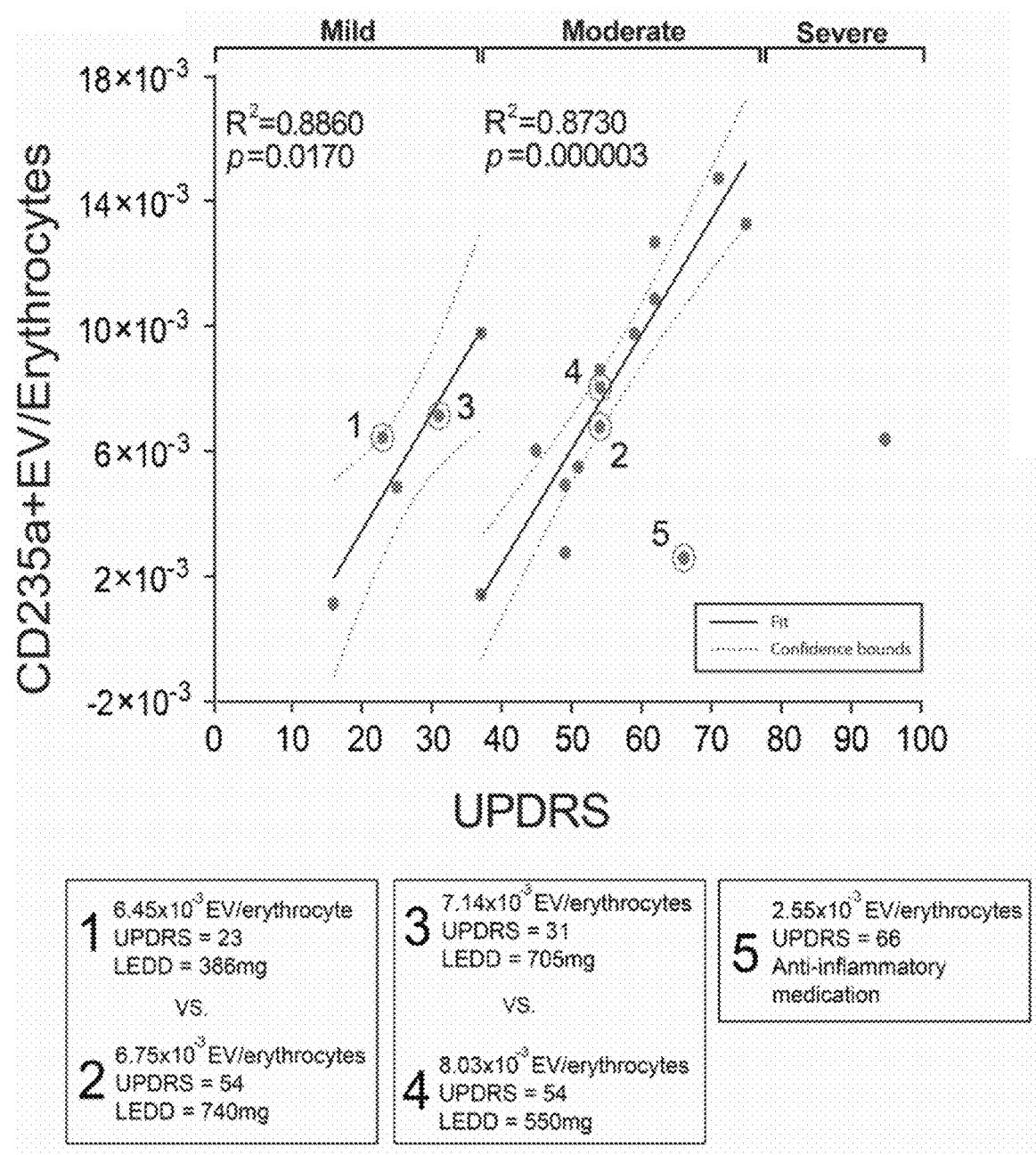
FIGS. 2A and 2B. EEV: A biomarker of PD state.

2.2 Increase in Erythrocyte-Derived EV in PD Patient Samples Correlates with PD Progression and PD Treatment To evaluate its suitability as a potential biomarker for monitoring PD progression, we examined correlations between the number of erythrocyte-derived EV (EEV) and the Unified Parkinson's Disease Rating Scale (UPDRS) PD staging system, because of its greater sensitivity and the recent publications validating this approach (Martinez-Martin et al., 2015). Strikingly, statistical linear regression analysis revealed strong correlations between the number of erythrocyte-derived EV and PD stage/progression. As shown in FIG. 2A, strong correlations (correlations exceeding were observed between the number of erythrocyte-derived EV (expressed as CD135a+ EV/total number of erythrocytes) and patient UPDRS score, and thus PD stages. The $R^2$ values obtained demonstrated that in both "mild" and "moderate" PD patient groups, at least 87% of the variation in the total number of EEV/erythrocytes is due to the variation of the UPDRS. Moreover, the results are significant with respect to the p values obtained for each fit, since they fall below the 5% confidence level. Hence, the statistical tests on EEV counts uncovered a clear cut-off point between mild and moderate PD patients, which could not be accounted for by daily levodopa doses administered to the patient (FIG. 2A, see details of the 5 patients pinpointed).

Figure 2B:
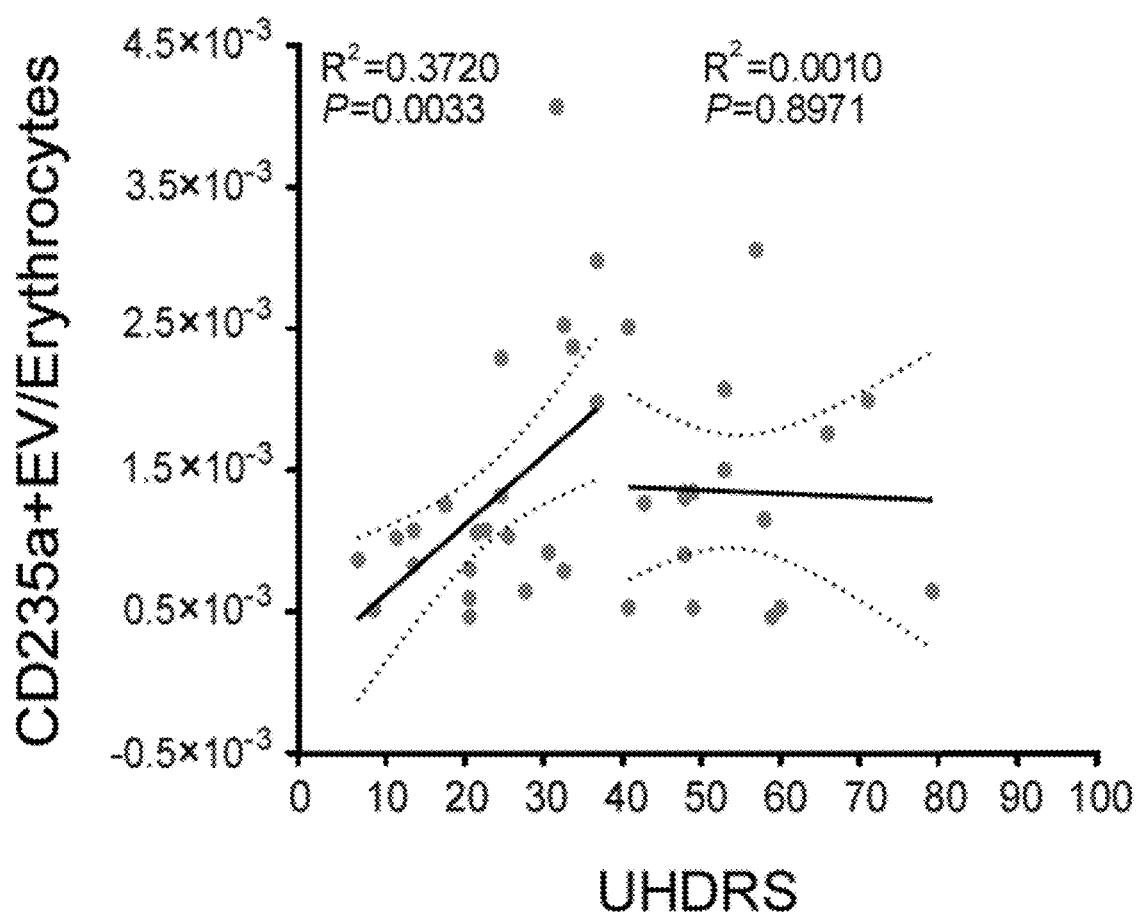

The above correlations observed with respect to the number of EEV in PD patients was found to be disease-specific, since a similar analysis performed in HD patients failed to reveal the same strong correlations (see FIG. 2B). In the HD cohort, the total number of EEV between pre-manifest and manifest HD was similar to their age- and sex-matched healthy Controls. In contrast to PD, correlation analyses failed to reveal an association between the number of EEV and HD stage using the United Huntington's Disease Rating Scale (UHDRS) score (FIG. 2B). Based on this, all our subsequent analyses focused only on the PD cohort. It is should be re-emphasized that total blood counts did not indicate any significant differences in the number of endothelial cell-, platelet-, monocyte- and granulocyte-derived EV in the platelet-free plasma (PFP) in PD (Table 2A) and HD patients (Table 2B), when compared to their respective control cohorts.

We have thus identified at least two distinct groups of PD patients with highly significant correlations to the number of EV derived from erythrocytes, which relates to PD stage and/or PD treatment (FIG. 2A). Strikingly, these correlations appear to be specific to PD, as similar correlations were not observed in the cohort of HD patients (of varying degrees of severity) in which we performed identical analyses (FIG. 2B).

2.3 α-Syn is not Differentially Expressed in Normal Vs. Diseased PD Conditions

Having established that EEV counts correlate with disease state in PD, we aimed to assess whether α-Syn—which is not only the main component of Lewy bodies but is highly expressed in most blood cells—was differentially expressed in normal vs. diseased conditions. For this, we opted to use scanning electron microscopy, but this did not reveal any morphological changes between resting and activated erythrocytes in either condition (FIG. 3A). We further used transmission electron microscopy to quantify the number of EEV containing α-Syn and phosphorylated (serine 129) forms of the protein but again no significant differences between PD patients and age- and sex-matched healthy Controls (FIGS. 3B and 3C) were observed. Quantified α-Syn levels in EEV from PD patients and Controls using commercial ELISA kits corroborated these results (FIG. 3D).

2.4 Analysis of the EEV Proteome Revealed 8 Differentially Expressed Proteins

Since our combined quantifications (ELISA and transmission electron microscopy) suggested that α-Syn levels could not be used as a blood marker of disease, we sought to obtain the specific protein signature of EEV from mild and moderate PD patients (with respect to the UPDRS scores) and their age-matched Controls. Given the significant amounts of hemoglobin within erythrocytes that could mask the true nature of the protein signature in EEV, we performed a label free quantitative proteomic analysis by nanoLC/MSMS (Wither et al., 2016) using two distinct approaches: with and without hemoglobin.

By removing the hemoglobin, we identified a total of 818 proteins in comparison with 356 when we did not perform this methodological step (refer to Table 4 for complete list of proteins), which clearly, provides a much more thorough evaluation of the protein content of EEV. Additionally, a Gene Ontology enrichment analysis on the 'Cellular Component' ontology performed on the two sets of identified proteins in comparison with the whole human proteome, revealed that our samples are enriched with elements associated to 'vesicles' and 'hemoglobin complex' which show the efficiency of our EEV production and purification protocol (data not shown).

Figure 4C:
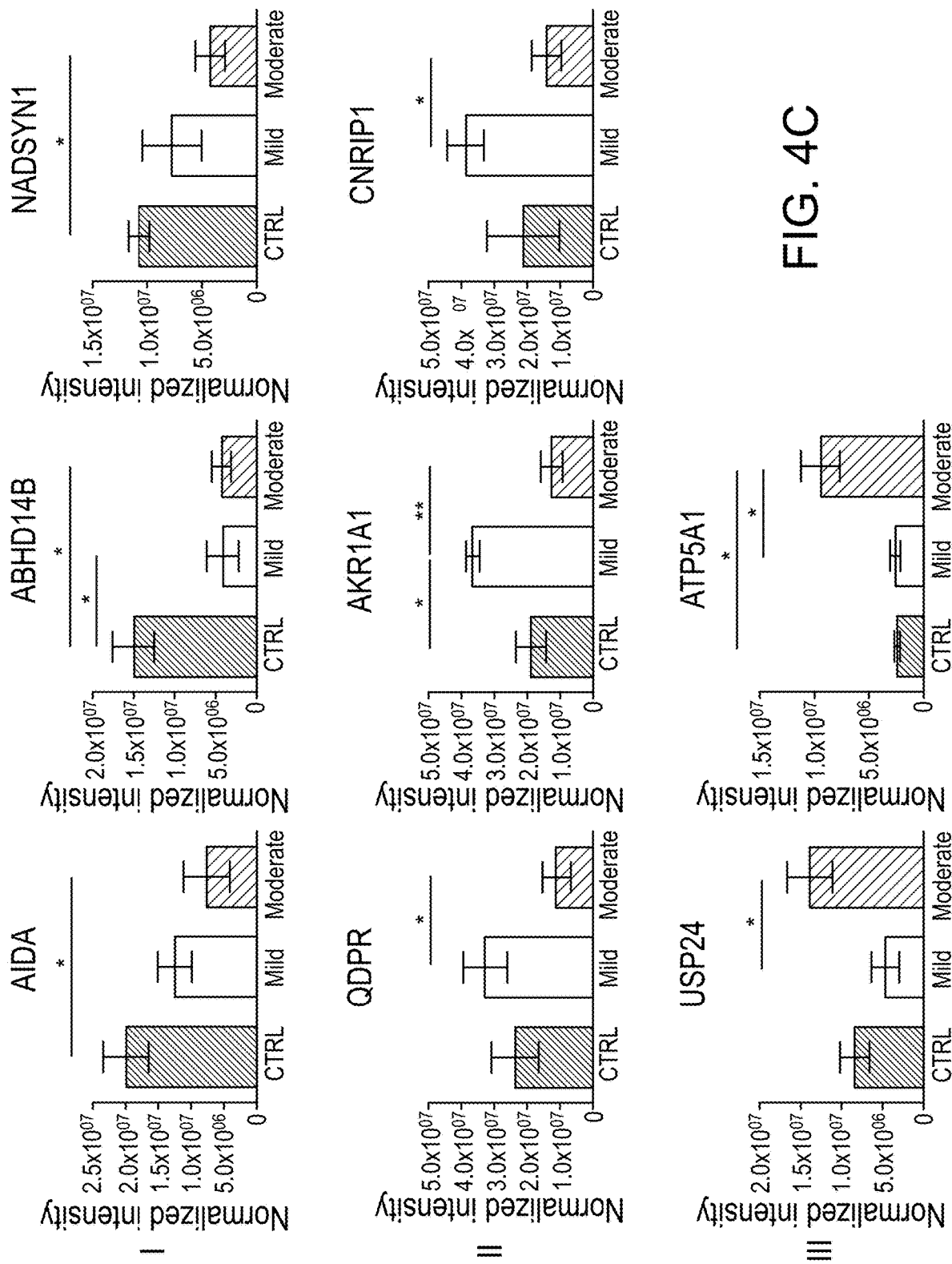
Figure 4D:
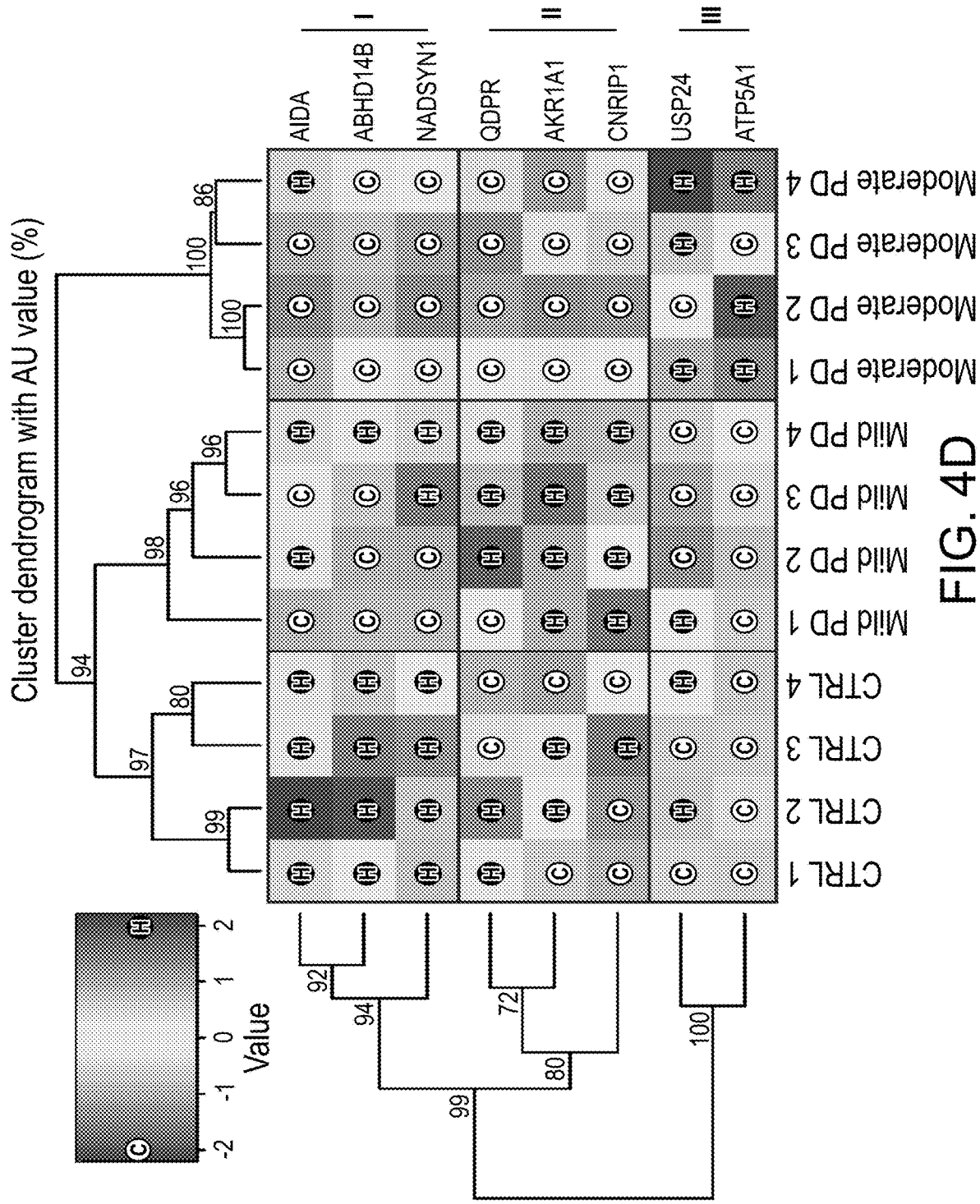

Out of the 818 proteins identified in the proteome of EEV, 8 had their expression significantly modified according to the different stages of PD (FIGS. 4A and 4B). Hierarchical clustering, coupled to a heatmap (FIG. 4D), allowed us to group individuals according to stages of disease (Control, mild PD and moderate PD) and provided compelling evidence that the 8 proteins identified could also be grouped into three categories. Proteins of group I were highly and predominantly expressed in Controls, proteins of group II were highly and predominantly expressed in mild PD patients, and proteins belonging to group III were highly and predominantly expressed in moderate PD patients (FIGS. 4B and 4C; Table 3). This data set was further confirmed by volcano plots (FIG. 5). Of note, two proteins of group I are associated with the regulation system of the cell (ABHD148, NADSYN1) and one protein significantly expressed in moderate PD patients (ATP5A1) is involved in the regulation of mitochondrial ATP.

TABLE 3

EEV proteins differentially expressed according to different stages of PD

| Groups | Protein | Gene |
|---|---|---|
| I (Control) | Axin interactor, dorsalization-associated protein | AIDA |
| | Alpha/beta hydrolase domain-containing protein 14B | ABHD14B |
| | Glutamine-dependent NAD(+) synthetase | NADSYN1 |
| II (mild PD) | Dihydropteridine reductase | QDPR |
| | Alcohol dehydrogenase [NADP(+)] | AKR1A1 |
| | CB1 cannabinoid receptor-interacting protein 1 | CNRIP1 |
| III (moderate PD) | Ubiquitin carboxyl-terminal hydrolase 24 | USP24 |
| | ATP synthase subunit alpha, mitochondrial | ATP5A1 |

Fold changes and the results of statistical analyses of the proteins of Table 3 are shown in Table 3.1, in which the proteins are listed in order of their "fold" difference for each group comparison. For example, a "fold" of 1.931 indicates that the AKR1A1 protein was detected in the isolated EEV preparations almost two times higher in the mild group, as compared to the control group.

TABLE 3.1

Fold changes and statistics of EEV proteins of Table 3

| Protein | Gene | Welch's test | Fold change | Z-score |
|---|---|---|---|---|
| Mild (Group II) v. Controls (Group I) | | | | |
| Alcohol dehydrogenase [NADP(+)] | AKR1A1 | 0.019 | 1.931 | 2.25 |
| Alpha/beta hydrolase domain-containing protein 14B | ABHD14B | 0.016 | 0.274 | −3.57 |
| Moderate (Group III) v. Controls (Group I) | | | | |
| ATP synthase subunit alpha, mitochondrial | ATP5A1 | 0.028 | 3.906 | 3.25 |
| Glutamine-dependent NAD(+) synthetase | NADSYN1 | 0.009 | 0.391 | −2.31 |
| Axin interactor, dorsalization-associated protein | AIDA | 0.046 | 0.379 | −2.38 |
| Alpha/beta hydrolase domain-containing protein 14B | ABHD14B | 0.017 | 0.282 | −3.09 |
| Moderate (Group III) v. Mild (Group II) | | | | |
| ATP synthase subunit alpha, mitochondrial | ATP5A1 | 0.027 | 3.629 | 2.77 |
| Ubiquitin carboxyl-terminal hydrolase 24 | USP24 | 0.036 | 2.971 | 2.29 |
| CB1 cannabinoid receptor-interacting protein 1 | CNRIP1 | 0.014 | 0.352 | −2.80 |
| Alcohol dehydrogenase [NADP(+)] | AKR1A1 | 0.002 | 0.342 | −2.87 |
| Dihydropteridine reductase | QDPR | 0.040 | 0.341 | −2.88 |

Proteins were considered as significantly differentially expressed if they respected two conditions: Z-score >1.96 or <−1.96, and Welch's test p-value < 0.05.

As seen in Table 3.1 and in FIG. 4C, the ABHD14B protein (alpha/beta hydrolase domain-containing protein 14B) was detected over 3.5-fold lower both in the mild v. controls and in the moderate v. controls groups, suggesting that this EEV protein may be a useful biomarker for clinically assessing symptomatic PD subjects. The results in Table 3.1 and in FIG. 4C suggest that the AKR1A1 protein (alcohol dehydrogenase [NADP(+)]) may be a useful biomarker for clinically assessing mild PD subjects, as this EEV protein was detected almost 2-fold higher in mild v. control PD subjects, but was not differentially expressed in moderate v. control PD subjects. Finally, the results in Table 3.1 and in FIG. 4C suggest that the ATP5A1 protein may be a useful biomarker for clinically assessing moderate PD subjects, since this protein was detected over 3.6-fold higher in both moderate v. controls and in moderate v. mild PD subjects.

Example 3—Discussion

We have identified biomarkers correlating to different states of PD based on the quantification of EV shed from erythrocytes and UPDRS scores. In particular, we have shown a strong correlation between the number of EEV and the clinical expression/stages of PD. Finding this level of correlation in a 60-patient sample size in such a heterogeneous disorder highlights the robustness of the biomarkers identified herein.

Although staging of PD is often done using the H & Y clinical scale, we sought to use the UPDRS given its greater sensitivity and the recent publications validating this approach (Martinez-Martin et al., 2015). Using these scores, we found that mild PD patients—with a UPDRS score lower than 37—are characterized by an increased number of EV during the mild disease stage (correlations=0.886); and that the same pattern repeated itself with patients who had UPDRS scores between 37 and 75 (correlations=0.873). When comparing individual patients from both correlation curves, the dose of levodopa taken daily did not seem to account for the differences, as there was no correlation between the levodopa dose and the number of EEV.

Finally, we herein report an improved method to perform proteomic analysis of EEV in blood samples by removing hemoglobin, a large protein that can easily mask other ones within a protein signature. Indeed, the high dynamic range of protein concentrations in erythrocytes and therefore in EEV, due to the high abundance of hemoglobin, decreases the capacity of the mass spectrometer to detect signals corresponding to low abundance proteins. Analyzing the hemoglobin separately from the other proteins of other molecular weights allowed us to go deeper in the EEV proteome by identifying 129% more proteins than in the initial analysis.

TABLE 4

Proteins identified in the EEV proteome. Lists of the proteins identified by LC-MS/MS analysis using Andromeda™/MaxQuant™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| (A). UNIPROT COMPLETE PROTEOME *HOMO SAPIENS* DATABASE FOR THE NON-DEPLETED SAMPLE | | | |
| P02549 | Spectrin alpha chain, erythrocytic 1 | SPTA1 | 136 |
| P11277 | Spectrin beta chain, erythrocytic | SPTB | 123 |
| P16157 | Ankyrin-1 | ANK1 | 70 |
| P02730 | Band 3 anion transport protein | SLC4A1 | 38 |
| P55072 | Transitional endoplasmic reticulum ATPase | VCP | 33 |
| P16452 | Erythrocyte membrane protein band 4.2 | EPB42 | 33 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
| --- | --- | --- | --- |
| P11171 | Protein 4.1 | EPB41 | 33 |
| P04040 | Catalase | CAT | 32 |
| Q13228 | Selenium-binding protein 1 | SELENBP1 | 29 |
| B4DT77 | Annexin; Annexin A7 | ANXA7 | 27 |
| Q8WUM4 | Programmed cell death 6-interacting protein | PDCD6IP | 27 |
| P35612 | Beta-adducin | ADD2 | 26 |
| P68871 | Hemoglobin subunit beta; LW-hemorphin-7; Spinorphin | HBB | 25 |
| Q00610 | Clathrin heavy chain 1 | CLTC | 25 |
| P69905 | Hemoglobin subunit alpha | HBA1 | 22 |
| B4DVE7 | Annexin A11 | ANXA11 | 20 |
| J3QLD9 | Flotillin-2 | FLOT2 | 20 |
| P08758 | Annexin A5; Annexin | ANXA5 | 19 |
| P09525 | Annexin A4; Annexin | ANXA4 | 18 |
| O75955; | Flotillin-1 | FLOT1 | 18 |
| P11142 | Heat shock cognate 71 kDa protein | HSPA8 | 18 |
| P32119 | Peroxiredoxin-2 | PRDX2 | 17 |
| P00491 | Purine nucleoside phosphorylase | PNP | 17 |
| P27105 | Erythrocyte band 7 integral membrane protein | STOM | 17 |
| P00918 | Carbonic anhydrase 2 | CA2 | 17 |
| P23634 | Plasma membrane calcium-transporting ATPase 4 | ATP2B4 | 17 |
| C9JIF9 | Acylamino-acid-releasing enzyme | APEH | 17 |
| P00915 | Carbonic anhydrase 1 | CA1 | 16 |
| P63261 | Actin, cytoplasmic 2 | ACTG1 | 16 |
| Q5VU58 | Tropomyosin alpha-3 chain | TPM3 | 16 |
| P30041 | Peroxiredoxin-6 | PRDX6 | 16 |
| E7EU23 | Rab GDP dissociation inhibitor beta | GDI2 | 16 |
| Q00013 | 55 kDa erythrocyte membrane protein | MPP1 | 16 |
| E7EV01 | Calpain-5 | CAPN5 | 16 |
| J3KPS3 | Fructose-bisphosphate aldolase A | ALDOA | 15 |
| Q08495 | Dematin | DMTN | 15 |
| P23276 | Kell blood group glycoprotein | KEL | 15 |
| P69892 | Hemoglobin subunit gamma-2 | HBG2 | 14 |
| P60174 | Triosephosphate isomerase | TPI1 | 14 |
| P62258 | 14-3-3 protein epsilon | YWHAE | 14 |
| O75326 | Semaphorin-7A | SEMA7A | 14 |
| O75340 | Programmed cell death protein 6 | PDCD6 | 13 |
| E7EV99 | Alpha-adducin | ADD1 | 13 |
| Q5VZU9 | Tripeptidyl-peptidase 2 | TPP2 | 13 |
| P53396 | ATP-citrate synthase | ACLY | 13 |
| C9J0K6 | Sorcin | SRI | 12 |
| P04406 | Glyceraldehyde-3-phosphate dehydrogenase | GAPDH | 12 |
| P07738 | Bisphosphoglycerate mutase | BPGM | 12 |
| B7Z3I9 | Delta-aminolevulinic acid dehydratase | ALAD | 12 |
| Q86X55 | Histone-arginine methyltransferase CARM1 | CARM1 | 12 |
| P07195 | L-lactate dehydrogenase B chain; L-lactate dehydrogenase | LDHB | 12 |
| P23526 | Adenosylhomocysteinase | AHCY | 12 |
| Q32Q12 | Nucleoside diphosphate kinase | NME1-NME2 | 12 |
| B7Z7A9 | Phosphoglycerate kinase 1 | PGK1 | 11 |
| P11166 | Solute carrier family 2, facilitated glucose transporter member 1 | SLC2A1 | 11 |
| P22303 | Acetylcholinesterase | ACHE | 11 |
| Q9NP58 | ATP-binding cassette sub-family B member 6, mitochondrial | ABCB6 | 11 |
| P40925 | Malate dehydrogenase, cytoplasmic; Malate dehydrogenase | MDH1 | 11 |
| P00352 | Retinal dehydrogenase 1 | ALDH1A1 | 11 |
| F2Z2V0 | Copine-1 | CPNE1 | 11 |
| K7EMC9 | WW domain-binding protein 2 | WBP2 | 10 |
| F5H7S3 | Tropomyosin alpha-1 chain | TPM1 | 10 |
| A6NN80 | Annexin A6; Annexin | ANXA6 | 10 |
| P30043 | Flavin reductase (NADPH) | BLVRB | 9 |
| H7BXD5 | Grancalcin | GCA | 9 |
| P04083 | Annexin A1; Annexin | ANXA1 | 9 |
| P62937 | Peptidyl-prolyl cis-trans isomerase | PPIA | 9 |
| P37837 | Transaldolase | TALDO1 | 9 |
| Q06830 | Peroxiredoxin-1 | PRDX1 | 9 |
| O75131 | Copine-3 | CPNE3 | 9 |
| P00390 | Glutathione reductase, mitochondrial | GSR | 9 |
| E7EQB2 | Lactotransferrin | LTF | 9 |
| P07384 | Calpain-1 catalytic subunit | CAPN1 | 9 |
| P02042 | Hemoglobin subunit delta | HBD | 8 |
| P30086 | Phosphatidylethanolamine-binding protein 1; Hippocampal cholinergic neurostimulating peptide | PEBP1 | 8 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P35613 | Basigin | BSG | 8 |
| Q9H0U4 | Ras-related protein Rab-1B; Putative Ras-related protein Rab-1C | RAB1B; RAB1C | 8 |
| P63092 | Guanine nucleotide-binding protein G(s) subunit alpha isoforms | GNAS | 8 |
| P48506 | Glutamate-cysteine ligase catalytic subunit | GCLC | 8 |
| P06702 | Protein S100-A9 | S100A9 | 7 |
| Q9UBV8 | Peflin | PEF1 | 7 |
| P17931 | Galectin-3; Galectin | LGALS3 | 7 |
| P28066 | Proteasome subunit alpha type-5 | PSMA5 | 7 |
| P07451 | Carbonic anhydrase 3 | CA3 | 7 |
| E7EQ12 | Calpastatin | CAST | 7 |
| P50895 | Basal cell adhesion molecule | BCAM | 7 |
| P28074 | Proteasome subunit beta type-5 | PSMB5 | 7 |
| G3V5Z7 | Proteasome subunit alpha type; Proteasome subunit alpha type-6 | PSMA6 | 7 |
| P25786 | Proteasome subunit alpha type-1 | PSMA1 | 7 |
| G3V1D3 | Dipeptidyl peptidase 3 | DPP3 | 7 |
| P49247 | Ribose-5-phosphate isomerase | RPIA | 7 |
| Q5T9B7 | Adenylate kinase isoenzyme 1 | AK1 | 7 |
| P25789 | Proteasome subunit alpha type-4; Proteasome subunit beta type | PSMA4 | 7 |
| B4E022 | Transketolase | TKT | 7 |
| J3QS39 | Ubiquitin-60S ribosomal protein L40; Ubiquitin; 60S ribosomal protein L40; Ubiquitin-40S ribosomal protein S27a; Ubiquitin; 40S ribosomal protein S27a; Polyubiquitin-B; Ubiquitin; Polyubiquitin-C; Ubiquitin | UBB; RPS27A; UBC; UBA52; UBBP4 | 6 |
| H0Y7A7 | Calmodulin | CALM2 | 6 |
| P28070 | Proteasome subunit beta type-4 | PSMB4 | 6 |
| Q9H4G4 | Golgi-associated plant pathogenesis-related protein 1 | GLIPR2 | 6 |
| Q9BY43 | Charged multivesicular body protein 4a | CHMP4A | 6 |
| P48426 | Phosphatidylinositol 5-phosphate 4-kinase type-2 alpha | PIP4K2A | 6 |
| P28289 | Tropomodulin-1 | TMOD1 | 6 |
| P07911 | Uromodulin; Uromodulin, secreted form | UMOD | 6 |
| Q9GZP4 | PITH domain-containing protein 1 | PITHD1 | 6 |
| P78417 | Glutathione S-transferase omega-1 | GSTO1 | 6 |
| P25788 | Proteasome subunit alpha type-3 | PSMA3 | 6 |
| O14818 | Proteasome subunit alpha type-7; Proteasome subunit alpha type-7-like | PSMA7; PSMA8 | 6 |
| P08107 | Heat shock 70 kDa protein 1A/1B | HSPA1A | 6 |
| H0YD13 | CD44 antigen | CD44 | 6 |
| P61225 | Ras-related protein Rap-2b; Ras-related protein Rap-2c; Ras-related protein Rap-2a | RAP2B; RAP2A; RAP2C | 6 |
| P05109 | Protein S100-A8; Protein S100-A8, N-terminally processed | S100A8 | 6 |
| P23528 | Cofilin-1 | CFL1 | 6 |
| Q99808 | Equilibrative nucleoside transporter 1 | SLC29A1 | 6 |
| P84077 | ADP-ribosylation factor 1; ADP-ribosylation factor 3; ADP-ribosylation factor 5; ADP-ribosylation factor 4 | ARF1; ARF3; ARF5; ARF4 | 6 |
| P31946 | 14-3-3 protein beta/alpha; 14-3-3 protein beta/alpha, N-terminally processed | YWHAB | 6 |
| C9JIS1 | Guanine nucleotide-binding protein G(I)/G(S)/G(T) subunit beta-2; Guanine nucleotide-binding protein subunit beta-4 | GNB2; GNB4 | 6 |
| P53990 | IST1 homolog | IST1 | 6 |
| Q99497 | Protein DJ-1 | PARK7 | 6 |
| F5H7U0 | 6-phosphogluconate dehydrogenase, decarboxylating | PGD | 6 |
| B7Z7E9 | Aspartate aminotransferase, cytoplasmic | GOT1 | 6 |
| P62834 | Ras-related protein Rap-1A; Ras-related protein Rap-1b; Ras-related protein Rap-1b-like protein | RAP1A; RAP1B | 6 |
| P04899 | Guanine nucleotide-binding protein G(i) subunit alpha-2 | GNAI2 | 6 |
| P25325 | 3-mercaptopyruvate sulfurtransferase; Sulfurtransferase | MPST | 6 |
| Q9NP79 | Vacuolar protein sorting-associated protein VTA1 homolog | VTA1 | 6 |
| P00492 | Hypoxanthine-guanine phosphoribosyltransferase | HPRT1 | 6 |
| Q16531 | DNA damage-binding protein 1 | DDB1 | 6 |
| P22314 | Ubiquitin-like modifier-activating enzyme 1 | UBA1 | 6 |
| P00441 | Superoxide dismutase [Cu—Zn] | SOD1 | 5 |
| H7BY58 | Protein-L-isoaspartate O-methyltransferase; Protein-L-isoaspartate(D-aspartate) O-methyltransferase | PCMT1 | 5 |
| P10768 | S-formylglutathione hydrolase | ESD | 5 |
| P09543 | 2,3-cyclic-nucleotide 3-phosphodiesterase | CNP | 5 |
| P06733 | Alpha-enolase; Enolase | ENO1 | 5 |
| P26038 | Moesin | MSN | 5 |
| O75368 | SH3 domain-binding glutamic acid-rich-like protein | SH3BGRL | 5 |
| K7EQ48 | Glucose-6-phosphate isomerase | GPI | 5 |
| P25787 | Proteasome subunit alpha type-2 | PSMA2 | 5 |
| P49721 | Proteasome subunit beta type-2 | PSMB2 | 5 |
| F5H8J2 | Protein disulfide-isomerase | P4HB | 5 |
| C9J9P4 | Phospholipid scramblase 1 | PLSCR1 | 5 |
| P09211 | Glutathione S-transferase P | GSTP1 | 5 |

TABLE 4-continued

Proteins identified in the EEV proteome. Lists of the proteins identified by LC-MS/MS analysis using Andromeda™/MaxQuant™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| B5MDF5 | GTP-binding nuclear protein Ran | RAN | 5 |
| P07900 | Heat shock protein HSP 90-alpha | HSP90AA1 | 5 |
| K7EQ02 | DAZ-associated protein 1 | DAZAP1 | 5 |
| Q13630 | GDP-L-fucose synthase | TSTA3 | 5 |
| F5H0T1 | Stress-induced-phosphoprotein 1 | STIP1 | 5 |
| P50502 | Hsc70-interacting protein; Putative protein FAM10A5; Putative protein FAM10A4 | ST13; ST13P5; ST13P4 | 5 |
| P20618 | Proteasome subunit beta type-1 | PSMB1 | 5 |
| P62805 | Histone H4 | HIST1H4A | 5 |
| P51148 | Ras-related protein Rab-5C | RAB5C | 5 |
| H7C2G2 | Ecto-ADP-ribosyltransferase 4 | ART4 | 5 |
| J3KQ18 | D-dopachrome decarboxylase; D-dopachrome decarboxylase-like protein | DDT; DDTL | 5 |
| H3BPK3 | Hydroxyacylglutathione hydrolase, mitochondrial | HAGH | 5 |
| B4DIT7 | Protein-glutamine gamma-glutamyltransferase 2 | TGM2 | 5 |
| O43633 | Charged multivesicular body protein 2a | CHMP2A | 5 |
| B4DQH4 | T-complex protein 1 subunit theta | CCT8 | 5 |
| Q9UN37 | Vacuolar protein sorting-associated protein 4A | VPS4A | 5 |
| I3L397 | Eukaryotic translation initiation factor 5A-1; Eukaryotic translation initiation factor 5A-1-like | EIF5A; EIF5AL1 | 5 |
| Q9Y5Z4 | Heme-binding protein 2 | HEBP2 | 5 |
| Q9UKV8 | Protein argonaute-2 | AGO2 | 5 |
| F5H442 | Tumor susceptibility gene 101 protein | TSG101 | 5 |
| H3BLV0 | Complement decay-accelerating factor | CD55 | 5 |
| P02008 | Hemoglobin subunit zeta | HBZ | 5 |
| E7EPV7 | Alpha-synuclein | SNCA | 4 |
| P63104 | 14-3-3 protein zeta/delta | YWHAZ | 4 |
| P02724 | Glycophorin-A | GYPA; GPErik | 4 |
| U3KQE2 | Calpain small subunit 1 | CAPNS1 | 4 |
| Q9NP59 | Solute carrier family 40 member 1 | SLC40A1 | 4 |
| Q5QPM9 | Proteasome inhibitor PI31 subunit | PSMF1 | 4 |
| C9J8U2 | Nicotinate phosphoribosyltransferase | NAPRT | 4 |
| P61981 | 14-3-3 protein gamma; 14-3-3 protein gamma, N-terminally processed | YWHAG | 4 |
| Q9UQ80 | Proliferation-associated protein 2G4 | PA2G4 | 4 |
| E5RJR5 | S-phase kinase-associated protein 1 | SKP1 | 4 |
| Q9NRV9 | Heme-binding protein 1 | HEBP1 | 4 |
| Q9H444 | Charged multivesicular body protein 4b | CHMP4B | 4 |
| P10599 | Thioredoxin | TXN | 4 |
| Q5VSJ9 | Blood group Rh(CE) polypeptide; Blood group Rh(D) polypeptide | RHCE; RHD | 4 |
| Q9UK41 | Vacuolar protein sorting-associated protein 28 homolog | VPS28 | 4 |
| Q9Y3I1 | F-box only protein 7 | FBXO7 | 4 |
| P61026 | Ras-related protein Rab-10 | RAB10 | 4 |
| Q14974 | Importin subunit beta-1 | KPNB1 | 4 |
| P27797 | Calreticulin | CALR | 4 |
| P18669 | Phosphoglycerate mutase 1; Probable phosphoglycerate mutase 4 | PGAM1; PGAM4 | 4 |
| P54725 | UV excision repair protein RAD23 homolog A | RAD23A | 4 |
| P30613 | Pyruvate kinase PKLR | PKLR | 4 |
| P63000 | Ras-related C3 botulinum toxin substrate 1; Ras-related C3 botulinum toxin substrate 3; Ras-related C3 botulinum toxin substrate 2 | RAC1; RAC3; RAC2 | 4 |
| P05164 | Myeloperoxidase | MPO | 4 |
| F5GWY2 | Bifunctional purine biosynthesis protein PURH; Phosphoribosylaminoimidazolecarboxamide formyltransferase; IMP cyclohydrolase | ATIC | 4 |
| P48637 | Glutathione synthetase | GSS | 4 |
| F5H5V4 | 26S proteasome non-ATPase regulatory subunit 9 | PSMD9 | 4 |
| G5E9R5 | Low molecular weight phosphotyrosine protein phosphatase | ACP1 | 3 |
| P46976 | Glycogenin-1 | GYG1 | 3 |
| P28072 | Proteasome subunit beta type-6 | PSMB6 | 3 |
| P26447 | Protein S100-A4 | S100A4 | 3 |
| F5GXQ0 | BRO1 domain-containing protein BROX | BROX | 3 |
| P08754 | Guanine nucleotide-binding protein G(k) subunit alpha | GNAI3 | 3 |
| Q99436 | Proteasome subunit beta type-7 | PSMB7 | 3 |
| P62942 | Peptidyl-prolyl cis-trans isomerase | FKBP1A | 3 |
| U3KQK0 | Histone H2B | HIST1H2B | 3 |
| J3QKR3 | Proteasome subunit beta type-3 | PSMB3 | 3 |
| P01116 | GTPase KRas; GTPase KRas, N-terminally processed; GTPase HRas; GTPase HRas, N-terminally processed; GTPase NRas | KRAS; HRAS; NRAS | 3 |
| P13489 | Ribonuclease inhibitor | RNH1 | 3 |
| Q08722 | Leukocyte surface antigen CD47 | CD47 | 3 |
| Q5T123 | SH3 domain-binding glutamic acid-rich-like protein 3 | SH3BGRL3 | 3 |
| Q8WYQ7 | Galectin; Galectin-9 | LGALS9 | 3 |
| O75695 | Protein XRP2 | RP2 | 3 |
| P00167 | Cytochrome b5 | CYB5A | 3 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| Q9Y4D1 | Dishevelled-associated activator of morphogenesis 1 | DAAM1 | 3 |
| P11021 | 78 kDa glucose-regulated protein | HSPA5 | 3 |
| H7C1D4 | Translin | TSN | 3 |
| P07737 | Profilin-1 | PFN1 | 3 |
| M0R389 | Platelet-activating factor acetylhydrolase IB subunit gamma | PAFAH1B3 | 3 |
| A6NJA2 | Ubiquitin carboxyl-terminal hydrolase 14 | USP14 | 3 |
| P10644 | cAMP-dependent protein kinase type I-alpha regulatory subunit | PRKAR1A | 3 |
| Q9BS40 | Latexin | LXN | 3 |
| G5EA52 | Protein disulfide-isomerase A3 | PDIA3 | 3 |
| P53004 | Biliverdin reductase A | BLVRA | 3 |
| Q04656 | Copper-transporting ATPase 1 | ATP7A | 3 |
| H9KV70 | Neutrophil gelatinase-associated lipocalin | LCN2 | 3 |
| O00299 | Chloride intracellular channel protein 1 | CLIC1 | 3 |
| F8WF69 | Clathrin light chain A | CLTA | 3 |
| G3V2F7 | Ubiquitin-conjugating enzyme E2 variant 1; Ubiquitin-conjugating enzyme E2 variant 2 | UBE2V1; UBE2V2 | 3 |
| F8WDS9 | LanC-like protein 1 | LANCL1 | 3 |
| P60891 | Ribose-phosphate pyrophosphokinase 1 | PRPS1 | 3 |
| K7ESE8 | Bleomycin hydrolase | BLMH | 3 |
| H0YNE3 | Proteasome activator complex subunit 1 | PSME1 | 3 |
| P16930 | Fumarylacetoacetase | FAH | 3 |
| F8VSD4 | Ubiquitin-conjugating enzyme E2 N | UBE2N | 3 |
| P07203 | Glutathione peroxidase 1 | GPX1 | 3 |
| P62328 | Thymosin beta-4; Hematopoietic system regulatory peptide | TMSB4X; TMSB4XP4 | 3 |
| E5RIW3 | Tubulin-specific chaperone A | TBCA | 3 |
| M0R0Y2 | Alpha-soluble NSF attachment protein | NAPA | 3 |
| P15374 | Ubiquitin carboxyl-terminal hydrolase isozyme L3 | UCHL3 | 3 |
| P04921 | Glycophorin-C | GYPC | 2 |
| H0YDI1 | Lymphocyte function-associated antigen 3 | CD58 | 2 |
| B4E220 | Aquaporin-1 | AQP1 | 2 |
| C9JEN3 | Protein lifeguard 3 | TMBIM1 | 2 |
| F5H2R5 | Rho GDP-dissociation inhibitor 2 | ARHGDIB | 2 |
| Q53TN4 | Cytochrome b reductase 1 | CYBRD1 | 2 |
| Q9NZD4 | Alpha-hemoglobin-stabilizing protein | AHSP | 2 |
| Q8NHG7 | Small VCP/p97-interacting protein | SVIP | 2 |
| Q5JYX0 | Cell division control protein 42 homolog | CDC42 | 2 |
| Q71RC9 | Small integral membrane protein 5 | SMIM5 | 2 |
| E9PNW4 | CD59 glycoprotein | CD59 | 2 |
| P09105 | Hemoglobin subunit theta-1 | HBQ1 | 2 |
| R4GN98 | Protein S100; Protein S100-A6 | S100A6 | 2 |
| O75531 | Barrier-to-autointegration factor; Barrier-to-autointegration factor, N-terminally processed | BANF1 | 2 |
| Q5T6W5 | Heterogeneous nuclear ribonucleoprotein K | HNRNPK | 2 |
| F5H4Q5 | Vacuolar protein sorting-associated protein 37C | VPS37C | 2 |
| J3QK90 | NSFL1 cofactor p47 | NSFL1C | 2 |
| H3BV85 | BolA-like protein 2 | BOLA2B; BOLA2 | 2 |
| Q9NRX4 | 14 kDa phosphohistidine phosphatase | PHPT1 | 2 |
| H3BS66 | Small integral membrane protein 1 | SMIM1 | 2 |
| E7ESC6 | Exportin-7 | XPO7 | 2 |
| P68402 | Platelet-activating factor acetyl hydrolase IB subunit beta | PAFAH1B2 | 2 |
| Q9BRF8 | Serine/threonine-protein phosphatase CPPED1 | CPPED1 | 2 |
| P08246 | Neutrophil elastase | ELANE | 2 |
| E9PN50 | 26S protease regulatory subunit 6A | PSMC3 | 2 |
| E7EUC7 | UTP-glucose-1-phosphate uridylyltransferase | UGP2 | 2 |
| B8ZZB8 | CB1 cannabinoid receptor-interacting protein 1 | CNRIP1 | 2 |
| E9PCS3 | 26S proteasome non-ATPase regulatory subunit 2 | PSMD2 | 2 |
| P59666 | Neutrophil defensin 3; HP 3-56; Neutrophil defensin 2; Neutrophil defensin 1; HP 1-56; Neutrophil defensin 2 | DEFA3; DEFA1 | 2 |
| O15400 | Syntaxin-7 | STX7 | 2 |
| P00338 | L-lactate dehydrogenase A chain | LDHA | 2 |
| P61970 | Nuclear transport factor 2 | NUTF2 | 2 |
| E7EMV0 | Protein diaphanous homolog 1 | DIAPH1 | 2 |
| F5GY90 | Porphobilinogen deaminase | HMBS | 2 |
| P61020 | Ras-related protein Rab-5B | RAB5B | 2 |
| Q99828 | Calcium and integrin-binding protein 1 | CIB1 | 2 |
| B4DUA0 | Plastin-2 | LCP1 | 2 |
| C9JTY3 | Protein TFG | TFG | 2 |
| P27348 | 14-3-3 protein theta | YWHAG | 2 |
| H0YKZ7 | Annexin; Annexin A2; Putative annexin A2-like protein | ANXA2; ANXA2P2 | 2 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P08238 | Heat shock protein HSP 90-beta | HSP90AB1 | 2 |
| J3KQP6 | Ras-related protein Rab-11B; Ras-related protein Rab-11A | RAB11A; RAB11B | 2 |
| A6NMU3 | Signal transducing adapter molecule 1 | STAM | 2 |
| P53985 | Monocarboxylate transporter 1 | SLC16A1 | 2 |
| F6USW4 | F-actin-capping protein subunit beta | CAPZB | 2 |
| O14964 | Hepatocyte growth factor-regulated tyrosine kinase substrate | HGS | 2 |
| P20020 | Plasma membrane calcium-transporting ATPase 1; Calcium-transporting ATPase | ATP2B1 | 2 |
| P36959 | GMP reductase 1 | GMPR | 2 |
| Q9Y376 | Calcium-binding protein 39 | CAB39 | 2 |
| Q9Y6M5 | Zinc transporter 1 | SLC30A1 | 2 |
| Q8IZ83 | Aldehyde dehydrogenase family 16 member A1 | ALDH16A1 | 2 |
| Q99459 | Cell division cycle 5-like protein | CDC5L | 2 |
| P06132 | Uroporphyrinogen decarboxylase | UROD | 2 |
| J3KNT0 | Fascin | FSCN1 | 2 |
| P49189 | 4-trimethylaminobutyraldehyde dehydrogenase | ALDH9A1 | 2 |
| H3BNT7 | 26S proteasome non-ATPase regulatory subunit 7 | PSMD7 | 2 |
| P05023 | Sodium/potassium-transporting ATPase subunit alpha-1; Sodium/potassium-transporting ATPase subunit alpha-3; Sodium/potassium-transporting ATPase subunit alpha-2; Sodium/potassium-transporting ATPase subunit alpha-4; Potassium-transporting ATPase alpha chain 1; Potassium-transporting ATPase alpha chain 2 | ATP1A1; ATP1A2; ATP1A3; ATP1A4; ATP4A; ATP12A | 2 |
| P34932 | Heat shock 70 kDa protein 4 | HSPA4 | 2 |
| K7EMV3 | Histone H3 | H3F3B | 2 |
| Q8IU68 | Transmembrane channel-like protein 8 | TMC8 | 2 |
| E7ENZ3 | T-complex protein 1 subunit epsilon | CCT5 | 2 |
| Q5TZA2 | Rootletin | CROCC | 2 |
| Q9P203 | BTB/POZ domain-containing protein 7 | BTBD7 | 2 |
| Q7LBR1 | Charged multivesicular body protein 1b | CHMP1B | 2 |
| U3KQ56 | Glyoxylate reductase/hydroxypyruvate reductase | GRHPR | 2 |
| H0YJ11 | Alpha-actinin-1; Alpha-actinin-2; Alpha-actinin-4 | ACTN1; ACTN4; ACTN2 | 2 |
| Q9UDT6 | CAP-Gly domain-containing linker protein 2 | CLIP2 | 2 |
| P09960 | Leukotriene A-4 hydrolase | LTA4H | 2 |
| Q5HY54 | Filamin-A | FLNA | 2 |
| E9PJL5 | Uncharacterized protein C12orf55; Putative uncharacterized protein C12orf63 | C12orf55; C12orf63 | 2 |
| G3V2U7 | Acylphosphatase; Acylphosphatase-1 | FBN3; ACYP1 | 2 |
| E9PQN4 | Complement receptor type 1 | CR1 | 2 |
| Q9BSL1 | Ubiquitin-associated domain-containing protein 1 | UBAC1 | 2 |
| Q04917 | 14-3-3 protein eta | YWHAH | 2 |
| B7ZBP9 | Serine/threonine-protein phosphatase 2A activator | PPP2R4; DKFZp781M17165 | 2 |
| Q8NDC0 | MAPK-interacting and spindle-stabilizing protein-like | MAPK1IP1L | 1 |
| P68133 | Actin, alpha skeletal muscle; Actin, alpha cardiac muscle 1; Actin, gamma-enteric smooth muscle; Actin, aortic smooth muscle | ACTA1; ACTC1; ACTG2; ACTA2 | 1 |
| P69891 | Hemoglobin subunit gamma-1 | HBG1 | 1 |
| S4R3Y4 | Protein AM BP; Alpha-1-microglobulin; Inter-alpha-trypsin inhibitor light chain; Trypstatin | AMBP | 1 |
| I3L3E4 | Charged multivesicular body protein 6 | CHMP6 | 1 |
| Q16570 | Atypical chemokine receptor 1 | ACKR1 | 1 |
| Q5VY30 | Retinol-binding protein 4; Plasma retinol-binding protein(1-182); Plasma retinol-binding protein(1-181); Plasma retinol-binding protein(1-179); Plasma retinol-binding protein(1-176) | RBP4 | 1 |
| E7END7 | Ras-related protein Rab-1A | RAB1A | 1 |
| Q5VU59 | | TPM3 | 1 |
| P17066 | Heat shock 70 kDa protein 6; Putative heat shock 70 kDa protein 7 | HSPA6; HSPA7 | 1 |
| Q04760 | Lactoylglutathione lyase | GLO1 | 1 |
| D6RD66 | WD repeat-containing protein 1 | WDR1 | 1 |
| K7EM02 | Katanin p60 ATPase-containing subunit A-like 2 | KATNAL2 | 1 |
| P14209 | CD99 antigen | CD99 | 1 |
| E9PIR7 | Thioredoxin reductase 1, cytoplasmic | GML; TXNRD1 | 1 |
| K7EMQ9 | | EIF3K | 1 |
| P15531 | Nucleoside diphosphate kinase A | NME1 | 1 |
| H7BZT4 | Small ubiquitin-related modifier 4; Small ubiquitin-related modifier 2; Small ubiquitin-related modifier 3 | SUMO2; SUMO3; SUMO4 | 1 |
| O00560 | Syntenin-1 | SDCBP | 1 |
| Q9BVM4 | Gamma-glutamylaminecyclotransferase | GGACT | 1 |
| K7EKH5 | Fructose-bisphosphate aldolase C | ALDOC | 1 |
| P49773 | Histidine triad nucleotide-binding protein 1 | HINT1 | 1 |
| H0YBY6 | Disks large-associated protein 2 | DLGAP2 | 1 |

TABLE 4-continued

Proteins identified in the EEV proteome. Lists of the proteins identified by LC-MS/MS analysis using Andromeda™/MaxQuant™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| Q9Y624 | Junctional adhesion molecule A | F11R | 1 |
| B1AKQ8 | Guanine nucleotide-binding protein G(I)/G(S)/G(T) subunit beta-1; Guanine nucleotide-binding protein G(I)/G(S)/G(T) subunit beta-3 | GNB1; GNB3 | 1 |
| K7EKN6 | Urea transporter 1 | SLC14A1 | 1 |
| I3L0K2 | Thioredoxin domain-containing protein 17 | TXNDC17 | 1 |
| A8MXY0 | Syntaxin-4 | STX4 | 1 |
| O14773 | Tripeptidyl-peptidase 1 | TPP1 | 1 |
| E9PNW0 | Nucleosome assembly protein 1-like 1; Nucleosome assembly protein 1-like 4 | NAP1L4; NAP1L1 | 1 |
| Q5TDH0 | Protein DDI1 homolog 2 | DDI2 | 1 |
| Q96JM4 | Leucine-rich repeat and IQ domain-containing protein 1 | LRRIQ1 | 1 |
| F5GWT9 | Phosphoribosylformylglycinamidine synthase | PFAS | 1 |
| F2Z3J2 | 26S proteasome non-ATPase regulatory subunit 5 | PSMD5 | 1 |
| J3QL74 | Zinc finger and BTB domain-containing protein 14 | ZBTB14 | 1 |
| E9PJC7 | CD82 antigen | CD82 | 1 |
| Q9H936 | Mitochondrial glutamate carrier 1 | SLC25A22 | 1 |
| D6RD63 | COP9 signalosome complex subunit 4 | COPS4 | 1 |
| Q6B0K9 | Hemoglobin subunit mu | HBM | 1 |
| Q31611 | HLA class I histocompatibility antigen, alpha chain G | HLA-G | 1 |
| H7BY04 | Laminin subunit gamma-3 | LAMC3 | 1 |
| Q9UL25 | Ras-related protein Rab-21 | RAB21 | 1 |
| H7C3P7 | Ras-related protein Ral-A | RALA | 1 |
| P08311 | Cathepsin G | CTSG | 1 |
| E9PE37 | Ras-related protein Rab-2A; Ras-related protein Rab-2B | RAB2B; RAB2A | 1 |
| G3V1N2 | | HBA2 | 1 |
| P00387 | NADH-cytochrome b5 reductase 3; NADH-cytochrome b5 reductase 3 membrane-bound form; NADH-cytochrome b5 reductase 3 soluble form | CYB5R3 | 1 |
| O75339 | Cartilage intermediate layer protein 1; Cartilage intermediate layer protein 1 C1; Cartilage intermediate layer protein 1 C2 | CILP | 1 |
| P14324 | Farnesyl pyrophosphate synthase | FDPS | 1 |
| K7EKG2 | Thioredoxin-like protein 1 | TXNL1 | 1 |
| (B). UNIPROT COMPLETE PROTEOME *HOMO SAPIENS* DATABASE WHEN THE HEMOGLOBIN WAS ANALYZED SEPARATELY | | | |
| P02549 | Spectrin alpha chain, erythrocytic 1 | SPTA1 | 197 |
| P11277 | Spectrin beta chain, erythrocytic | SPTB | 177 |
| P16157 | Ankyrin-1 | ANK1 | 94 |
| P55072 | Transitional endoplasmic reticulum ATPase | VCP | 53 |
| P11714 | Protein 4.1 | EPB41 | 52 |
| P35579 | Myosin-9 | MYH9 | 44 |
| Q8WUM4 | Programmed cell death 6-interacting protein | PDCD6IP | 43 |
| P02730 | Band 3 anion transport protein | SLC4A1 | 43 |
| P16452 | Erythrocyte membrane protein band 4.2 | EPB42 | 42 |
| P04040 | Catalase | CAT | 40 |
| A0A087WVQ6 | Clathrin heavy chain; Clathrin heavy chain 1 | CLTC | 38 |
| P35612 | Beta-adducin | ADD2 | 37 |
| P16157 | Ankyrin-1 | ANK1 | 36 |
| Q14254 | Flotillin-2 | FLOT2 | 33 |
| P20073 | Annexin A7 | ANXA7 | 31 |
| O75955 | Flotillin-1 | FLOT1 | 30 |
| P53396 | ATP-citrate synthase | ACLY | 30 |
| P06753 | | TPM3 | 29 |
| P49368 | T-complex protein 1 subunit gamma | CCT3 | 29 |
| P236344 | Plasma membrane calcium-transporting ATPase 4 | ATP2B4 | 28 |
| P11142 | Heat shock cognate 71 kDa protein | HSPA8 | 28 |
| P60709 | Actin, cytoplasmic 1; Actin, cytoplasmic 1, N-terminally processed | ACTB | 28 |
| Q5T4S7 | E3 ubiquitin-protein ligase UBR4 | UBR4 | 27 |
| P78371 | T-complex protein 1 subunit beta | CCT2 | 26 |
| P28289 | Tropomodulin-1 | TMOD1 | 26 |
| P50395 | Rab GDP dissociation inhibitor beta | GDI2 | 25 |
| P27105 | Erythrocyte band 7 integral membrane protein | STOM | 25 |
| P68871 | Hemoglobin subunit beta; LW-hemorphin-7; Spinorphin | HBB | 25 |
| P02730 | Band 3 anion transport protein | SLC4A1 | 25 |
| Q00013 | 55 kDa erythrocyte membrane protein | MPP1 | 24 |
| J3KPS3 | Fructose-bisphosphate aldolase; Fructose-bisphosphate aldolase A | ALDOA | 24 |
| P00352 | Retinal dehydrogenase 1 | ALDH1A1 | 24 |
| Q86VP6 | Cullin-associated NEDD8-dissociated protein 1 | CAND1 | 24 |
| P49327 | Fatty acid synthase | FASN | 24 |
| Q13228 | Selenium-binding protein 1 | SELENBP1 | 22 |
| P00915 | Carbonic anhydrase 1 | CA1 | 22 |
| P50991 | T-complex protein 1 subunit delta | CCT4 | 22 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P50990 | T-complex protein 1 subunit theta | CCT8 | 22 |
| P32119 | Peroxiredoxin-2 | PRDX2 | 21 |
| P50995 | Annexin A11 | ANXA11 | 21 |
| P69905 | Hemoglobin subunit alpha | HBA1 | 21 |
| P00558 | Phosphoglycerate kinase 1 | PGK1 | 20 |
| H7BXK9 | ATP-binding cassette sub-family B member 6, mitochondrial | ABCB6 | 20 |
| P08758 | Annexin A5; Annexin | ANXA5 | 20 |
| P09525 | Annexin A4; Annexin | ANXA4 | 20 |
| P07900 | Heat shock protein HSP 90-alpha | HSP90AA1 | 20 |
| P48643 | T-complex protein 1 subunit epsilon | CCT5 | 20 |
| P07384 | Calpain-1 catalytic subunit | CAPN1 | 20 |
| P22314 | Ubiquitin-like modifier-activating enzyme 1 | UBA1 | 19 |
| P04406 | Glyceraldehyde-3-phosphate dehydrogenase | GAPDH | 19 |
| Q08495 | Dematin | DMTN | 19 |
| Q99832 | T-complex protein 1 subunit eta | CCT7 | 19 |
| P29144 | Tripeptidyl-peptidase 2 | TPP2 | 19 |
| P30041 | Peroxiredoxin-6 | PRDX6 | 18 |
| E9PM69 | 26S protease regulatory subunit 6A | PSMC3 | 18 |
| P40227 | T-complex protein 1 subunit zeta | CCT6A | 18 |
| P50570 | Dynamin-2 | DNM2 | 18 |
| E7EQB2 | Lactotransferrin; Lactoferricin-H; Kaliocin-1; Lactoferroxin-A; Lactoferroxin-B; Lactoferroxin-C | LTF | 18 |
| P31948 | Stress-induced-phosphoprotein 1 | STIP1 | 18 |
| E7ESC6 | Exportin-7 | XPO7 | 18 |
| E7EV99 | Alpha-adducin | ADD1 | 17 |
| P62258 | 14-3-3 protein epsilon | YWHAE | 17 |
| P30613 | Pyruvate kinase PKLR | PKLR | 17 |
| A0A0G2JIW1 | Heat shock 70 kDa protein 1B; Heat shock 70 kDa protein 1A | HSPA1B; HSPA1A | 17 |
| Q16531 | DNA damage-binding protein 1 | DDB1 | 17 |
| P11021 | 78 kDa glucose-regulated protein | HSPA5 | 17 |
| F5H2F4 | C-1-tetrahydrofolate synthase, cytoplasmic; Methylenetetrahydrofolate dehydrogenase | MTHFD1 | 17 |
| P07195 | L-lactate dehydrogenase B chain; L-lactate dehydrogenase | LDHB | 16 |
| P45974 | Ubiquitin carboxyl-terminal hydrolase 5 | USP5 | 16 |
| O43242 | 26S proteasome non-ATPase regulatory subunit 3 | PSMD3 | 16 |
| C9J0K6 | Sorcin | SRI | 16 |
| P08133 | Annexin A6; Annexin | ANXA6 | 16 |
| Q13200 | 26S proteasome non-ATPase regulatory subunit 2 | PSMD2 | 16 |
| P23276 | Kell blood group glycoprotein | KEL | 16 |
| P34932 | Heat shock 70 kDa protein 4 | HSPA4 | 16 |
| A0A0A0MSI0 | Peroxiredoxin-1 | PRDX1 | 16 |
| Q9Y230 | RuvB-like 2 | RUVBL2 | 16 |
| Q5XPI4 | E3 ubiquitin-protein ligase RNF123 | RNF123 | 16 |
| P68871 | Hemoglobin subunit beta; LW-hemorphin-7; Spinorphin | HBB | 15 |
| P60174 | Triosephosphate isomerase | TPI1 | 15 |
| P00491 | Purine nucleoside phosphorylase | PNP | 15 |
| C9JIF9 | Acylamino-acid-releasing enzyme | APEH | 15 |
| H7BYY1 | Tropomyosin alpha-1 chain | TPM1 | 15 |
| P35998 | 26S protease regulatory subunit 7 | PSMC2 | 15 |
| P17987 | T-complex protein 1 subunit alpha | TCP1 | 15 |
| P09543 | 2,3-cyclic-nucleotide 3-phosphodiesterase | CNP | 15 |
| Q99460 | 26S proteasome non-ATPase regulatory subunit 1 | PSMD1 | 15 |
| Q9Y4E8 | Ubiquitin carboxyl-terminal hydrolase 15 | USP15 | 15 |
| Q9C0C9 | E2/E3 hybrid ubiquitin-protein ligase UBE2O | UBE2O | 15 |
| P26038 | Moesin | MSN | 15 |
| P04083 | Annexin A1; Annexin | ANXA1 | 14 |
| P30043 | Flavin reductase (NADPH) | BLVRB | 14 |
| P11166 | Solute carrier family 2, facilitated glucose transporter member 1 | SLC2A1 | 14 |
| P00918 | Carbonic anhydrase 2 | CA2 | 14 |
| P06733 | Alpha-enolase | ENO1 | 14 |
| Q5TDH0 | Protein DDI1 homolog 2 | DDI2 | 14 |
| B0QZ18 | Copine-1 | CPNE1 | 14 |
| O75326 | Semaphorin-7A | SEMA7A | 14 |
| P05164 | Myeloperoxidase | MPO | 14 |
| Q9Y265 | RuvB-like 1 | RUVBL1 | 14 |
| P29401 | Transketolase | TKT | 14 |
| I3L0N3 | Vesicle-fusing ATPase | NSF | 14 |
| Q4VB86 | Protein 4.1 | EPB41 | 14 |
| P11277 | Spectrin beta chain, erythrocytic | SPTB | 14 |
| P13716 | Delta-aminolevulinic acid dehydratase | ALAD | 13 |
| P07738 | Bisphosphoglycerate mutase | BPGM | 13 |
| P48506 | Glutamate-cysteine ligase catalytic subunit | GCLC | 13 |

TABLE 4-continued

Proteins identified in the EEV proteome. Lists of the proteins identified by LC-MS/MS analysis using Andromeda™/MaxQuant™ search engine in the Uniprot Complete Proteome Homo sapiens database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| Q99816 | Tumor susceptibility gene 101 protein | TSG101 | 13 |
| O14818 | Proteasome subunit alpha type-7 | PSMA7 | 13 |
| P23526 | Adenosylhomocysteinase | AHCY | 13 |
| P61225 | Ras-related protein Rap-2b | RAP2B | 13 |
| O00231 | 26S proteasome non-ATPase regulatory subunit 11 | PSMD11 | 13 |
| P11413 | Glucose-6-phosphate 1-dehydrogenase | G6PD | 13 |
| P00338 | L-lactate dehydrogenase A chain | LDHA | 12 |
| Q99808 | Equilibrative nucleoside transporter 1 | SLC29A1 | 12 |
| A6NJA2 | Ubiquitin carboxyl-terminal hydrolase; Ubiquitin carboxyl-terminal hydrolase 14 | USP14 | 12 |
| Q06323 | Proteasome activator complex subunit 1 | PSME1 | 12 |
| P28074 | Proteasome subunit beta type-5 | PSMB5 | 12 |
| B3KQV6 | Serine/threonine-protein phosphatase 2A 65 kDa regulatory subunit A alpha isoform | PPP2R1A | 12 |
| Q14974 | Importin subunit beta-1 | KPNB1 | 12 |
| P25786 | Proteasome subunit alpha type-1; Proteasome subunit alpha type | PSMA1 | 12 |
| Q86X55 | Histone-arginine methyltransferase CARM1 | CARM1 | 12 |
| A6NG10 | WW domain-binding protein 2 | WBP2 | 12 |
| P63092 | Guanine nucleotide-binding protein G(s) subunit alpha | GNAS | 12 |
| P31939 | Bifunctional purine biosynthesis protein PURH; Phosphoribosylaminoimidazolecarboxamide formyltransferase; IMP cyclohydrolase | ATIC | 12 |
| P52209 | 6-phosphogluconate dehydrogenase, decarboxylating | PGD | 12 |
| A0A087X0C8 | Calpain-5 | CAPN5 | 12 |
| F8W9S7 | GTPase-activating protein and VPS9 domain-containing protein 1 | GAPVD1 | 12 |
| P60842 | Eukaryotic initiation factor 4A-I | EIF4A1 | 12 |
| P69905 | Hemoglobin subunit alpha | HBA1 | 11 |
| Q6XQN6 | Nicotinate phosphoribosyltransferase | NAPRT | 11 |
| P48637 | Glutathione synthetase | GSS | 11 |
| H7BZ94 | Protein disulfide-isomerase | P4HB | 11 |
| P21980 | Protein-glutamine gamma-glutamyltransferase 2 | TGM2 | 11 |
| P50895 | Basal cell adhesion molecule | BCAM | 11 |
| A0A087X2I1 | 26S protease regulatory subunit 10B | PSMC6 | 11 |
| G3V1D3 | Dipeptidyl peptidase 3 | DPP3 | 11 |
| P05023 | Sodium/potassium-transporting ATPase subunit alpha-1; Sodium/potassium-transporting ATPase subunit alpha-3 | ATP1A1; ATP1A3 | 11 |
| P40925 | Malate dehydrogenase, cytoplasmic; Malate dehydrogenase | MDH1 | 11 |
| Q9UKV8 | Protein argonaute-2 | AGO2 | 11 |
| P30566 | Adenylosuccinate lyase | ADSL | 11 |
| P20618 | Proteasome subunit beta type-1 | PSMB1 | 11 |
| P17858 | ATP-dependent 6-phosphofructokinase, liver type | PFKL | 11 |
| A0A087X253 | AP-2 complex subunit beta | AP2B1 | 11 |
| O95782 | AP-2 complex subunit alpha-1 | AP2A1 | 11 |
| O00232 | 26S proteasome non-ATPase regulatory subunit 12 | PSMD12 | 11 |
| Q9BSL1 | Ubiquitin-associated domain-containing protein 1 | UBAC1 | 11 |
| A0A087WUL0 | Bifunctional ATP-dependent dihydroxyacetone kinase/FAD-AMP lyase (cyclizing); ATP-dependent dihydroxyacetone kinase; FAD-AMP lyase (cyclizing) | TKFC; DAK | 11 |
| P69891 | Hemoglobin subunit gamma-1 | HBG1 | 11 |
| A0A087WZE4 | Spectrin alpha chain, erythrocytic 1 | SPTA1 | 11 |
| P48426 | Phosphatidylinositol 5-phosphate 4-kinase type-2 alpha | PIP4K2A | 10 |
| P10644 | cAMP-dependent protein kinase type I-alpha regulatory subunit | PRKAR1A | 10 |
| Q9BWD1 | Acetyl-CoA acetyltransferase, cytosolic | ACAT2 | 10 |
| P62191 | 26S protease regulatory subunit 4 | PSMC1 | 10 |
| E9PBS1 | Multifunctional protein ADE2; Phosphoribosylaminoimidazole-succinocarboxamide synthase; Phosphoribosylaminoimidazole carboxylase | PAICS | 10 |
| M0R0Y2 | Alpha-soluble NSF attachment protein | NAPA | 10 |
| P78417 | Glutathione S-transferase omega-1 | GSTO1 | 10 |
| P25789 | Proteasome subunit alpha type-4; Proteasome subunit alpha type; Proteasome subunit beta type | PSMA4 | 10 |
| Q9H0U4 | Ras-related protein Rab-1B; Putative Ras-related protein Rab-1C | RAB1B; RAB1C | 10 |
| Q16401 | 26S proteasome non-ATPase regulatory subunit 5 | PSMD5 | 10 |
| P30101 | Protein disulfide-isomerase A3 | PDIA3 | 10 |
| D6RAX7 | COP9 signalosome complex subunit 4 | COPS4 | 10 |
| O75340 | Programmed cell death protein 6 | PDCD6 | 10 |
| Q96P70 | Importin-9 | IPO9 | 10 |
| P38606 | V-type proton ATPase catalytic subunit A | ATP6V1A | 10 |
| A0A0G2JH68 | Protein diaphanous homolog 1 | DIAPH1 | 10 |
| Q5T9B7 | Adenylate kinase isoenzyme 1 | AK1 | 10 |
| O14980 | Exportin-1 | XPO1 | 10 |
| P43686 | 26S protease regulatory subunit 6B | PSMC4 | 10 |
| H0YH81 | ATP synthase subunit beta; ATP synthase subunit beta, mitochondrial | ATP5B | 10 |
| Q04656 | Copper-transporting ATPase 1 | ATP7A | 10 |
| P16452 | Erythrocyte membrane protein band 4.2 | EPB42 | 10 |
| Q9BY43 | Charged multivesicular body protein 4a | CHMP4A | 9 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P51148 | Ras-related protein Rab-5C | RAB5C | 9 |
| Q9NRV9 | Heme-binding protein 1 | HEBP1 | 9 |
| Q9UNZ2 | NSFL1 cofactor p47 | NSFL1C | 9 |
| Q16851 | UTP--glucose-1-phosphate uridylyltransferase | UGP2 | 9 |
| P28066 | Proteasome subunit alpha type-5 | PSMA5 | 9 |
| A0A0C4DGQ5 | Calpain small subunit 1 | CAPNS1 | 9 |
| A0A087X1Z3 | Proteasome activator complex subunit 2 | PSME2 | 9 |
| Q01518 | Adenylyl cyclase-associated protein 1 | CAP1 | 9 |
| B1AKQ8 | Guanine nucleotide-binding protein G(I)/G(S)/G(T) subunit beta-1 | GNB1 | 9 |
| O75131 | Copine-3 | CPNE3 | 9 |
| P54725 | UV excision repair protein RAD23 homolog A | RAD23A | 9 |
| P11215 | Integrin alpha-M | ITGAM | 9 |
| Q93008 | Probable ubiquitin carboxyl-terminal hydrolase FAF-X | USP9X | 9 |
| Q96G03 | Phosphoglucomutase-2 | PGM2 | 9 |
| P49721 | Proteasome subunit beta type-2 | PSMB2 | 9 |
| Q15008 | 26S proteasome non-ATPase regulatory subunit 6 | PSMD6 | 9 |
| Q9UNQ0 | ATP-binding cassette sub-family G member 2 | ABCG2 | 9 |
| P22303 | Acetylcholinesterase; Carboxylic ester hydrolase | ACHE | 9 |
| G3V5Z7 | Proteasome subunit alpha type; Proteasome subunit alpha type-6 | PSMA6 | 9 |
| O15439 | Multidrug resistance-associated protein 4 | ABCC4 | 9 |
| P37837 | Transaldolase | TALDO1 | 9 |
| O14744 | Protein arginine N-methyltransferase 5 | PRMT5 | 9 |
| P02042 | Hemoglobin subunit delta | HBD | 9 |
| P25788 | Proteasome subunit alpha type-3 | PSMA3 | 8 |
| J3QS39 | Ubiquitin-60S ribosomal protein L40; Ubiquitin; 60S ribosomal protein L40; Ubiquitin-40S ribosomal protein S27a; Ubiquitin; 40S ribosomal protein S27a; Polyubiquitin-B; Ubiquitin; Polyubiquitin-C; Ubiquitin | UBB; RPS27A; UBC; UBA52; UBBP4 | 8 |
| O94919 | Endonuclease domain-containing 1 protein | ENDOD1 | 8 |
| P31946 | 14-3-3 protein beta/alpha | YWHAB | 8 |
| P60891 | Ribose-phosphate pyrophosphokinase 1; Ribose-phosphate pyrophosphokinase 2; Ribose-phosphate pyrophosphokinase 3 | PRPS1; PRPS2; PRPS1L1 | 8 |
| P62195 | 26S protease regulatory subunit 8 | PSMC5 | 8 |
| A0A024RA52 | Proteasome subunit alpha type; Proteasome subunit alpha type-2 | PSMA2 | 8 |
| P04899 | Guanine nucleotide-binding protein G(i) subunit alpha-2 | GNAI2 | 8 |
| Q13561 | Dynactin subunit 2 | DCTN2 | 8 |
| P53004 | Biliverdin reductase A | BLVRA | 8 |
| P00387 | NADH-cytochrome b5 reductase 3 | CYB5R3 | 8 |
| P16152 | Carbonyl reductase [NADPH] 1 | CBR1 | 8 |
| P06744 | Glucose-6-phosphate isomerase | GPI | 8 |
| Q99733 | Nucleosome assembly protein 1-like 4 | NAP1L4 | 8 |
| P04792 | Heat shock protein beta-1 | HSPB1 | 8 |
| P17612 | cAMP-dependent protein kinase catalytic subunit alpha; cAMP-dependent protein kinase catalytic subunit beta | PRKACA; KIN27; PRKACB | 8 |
| P20340 | Ras-related protein Rab-6A | RAB6A | 8 |
| P13796 | Plastin-2 | LCP1 | 8 |
| P52907 | F-actin-capping protein subunit alpha-1 | CAPZA1 | 8 |
| Q14697 | Neutral alpha-glucosidase AB | GANAB | 8 |
| P08514 | Integrin alpha-IIb; Integrin alpha-IIb heavy chain; Integrin alpha-IIb light chain, form 1; Integrin alpha-IIb light chain, form 2 | ITGA2B | 8 |
| P26641 | Elongation factor 1-gamma | EEF1G | 8 |
| Q9UQ80 | Proliferation-associated protein 2G4 | PA2G4 | 8 |
| Q9Y4D1 | Disheveled-associated activator of morphogenesis 1 | DAAM1 | 8 |
| P11166 | Solute carrier family 2, facilitated glucose transporter member 1 | SLC2A1 | 8 |
| P63261 | Actin, cytoplasmic 2; Actin, cytoplasmic 2, N-terminally processed; Actin, cytoplasmic 1; Actin, cytoplasmic 1, N-terminally processed; Actin, gamma-enteric smooth muscle; Actin, alpha skeletal muscle; Actin, alpha cardiac muscle 1; Actin, aortic smooth muscle | ACTG1; ACTB; ACTG2; ACTA1; ACTC1; ACTA2 | 8 |
| P02008 | Hemoglobin subunit zeta | HBZ | 8 |
| P20073 | Annexin A7 | ANXA7 | 8 |
| P35613 | Basigin | BSG | 8 |
| P49720 | Proteasome subunit beta type-3 | PSMB3 | 7 |
| P17931 | Galectin-3; Galectin | LGALS3 | 7 |
| P63104 | 14-3-3 protein zeta/delta | YWHAZ | 7 |
| Q9H444 | Charged multivesicular body protein 4b | CHMP4B | 7 |
| O43396 | Thioredoxin-like protein 1 | TXNL1 | 7 |
| P50502 | Hsc70-interacting protein; Putative protein FAM10A4; Putative protein FAM10A5 | ST13; ST13P4; ST13P5 | 7 |
| E7EQ12 | Calpastatin | CAST | 7 |
| P49189 | 4-trimethylaminobutyraldehyde dehydrogenase | ALDH9A1 | 7 |
| Q9Y3I1 | F-box only protein 7 | FBXO7 | 7 |
| P07954 | Fumarate hydratase, mitochondrial | FH | 7 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| F6S8N6 | Protein-L-isoaspartate O-methyltransferase; Protein-L-isoaspartate(D-aspartate) O-methyltransferase | PCMT1 | 7 |
| P49247 | Ribose-5-phosphate isomerase | RPIA | 7 |
| P62834 | Ras-related protein Rap-1A | RAP1A | 7 |
| A0A087WUQ6 | Glutathione peroxidase; Glutathione peroxidase 1 | GPX1 | 7 |
| O60256 | Phosphoribosyl pyrophosphate synthase-associated protein 2 | PRPSAP2 | 7 |
| Q00796 | Sorbitol dehydrogenase | SORD | 7 |
| O00299 | Chloride intracellular channel protein 1 | CLIC1 | 7 |
| Q99497 | Protein deglycase DJ-1 | PARK7 | 7 |
| P17174 | Aspartate aminotransferase, cytoplasmic | GOT1 | 7 |
| H7BXD5 | Grancalcin | GCA | 7 |
| E9PGT1 | Translin | TSN | 7 |
| C9J7K9 | Phospholipid scramblase 1 | PLSCR1 | 7 |
| Q13618 | Cullin-3 | CUL3 | 7 |
| O75695 | Protein XRP2 | RP2 | 7 |
| P09960 | Leukotriene A-4 hydrolase | LTA4H | 7 |
| E9PLK3 | Puromycin-sensitive aminopeptidase | NPEPPS | 7 |
| P00492 | Hypoxanthine-guanine phosphoribosyltransferase | HPRT1 | 7 |
| F5H4B6 | Aldehyde dehydrogenase family 16 member A1 | ALDH16A1 | 7 |
| D6RA82 | Annexin; Annexin A3 | ANXA3 | 7 |
| P61106 | Ras-related protein Rab-14 | RAB14 | 7 |
| Q16775 | Hydroxyacylglutathione hydrolase, mitochondrial | HAGH | 7 |
| P07355 | Annexin A2; Annexin; Putative annexin A2-like protein | ANXA2; ANXA2P2 | 7 |
| A0A087WX08 | Gamma-adducin | ADD3 | 7 |
| P08238 | Heat shock protein HSP 90-beta | HSP90AB1 | 7 |
| Q8IZY2 | ATP-binding cassette sub-family A member 7 | ABCA7 | 7 |
| P14780 | Matrix metalloproteinase-9 | MMP9 | 7 |
| P12955 | Xaa-Pro dipeptidase | PEPD | 7 |
| P68371 | Tubulin beta-4B chain; Tubulin beta-4A chain; Tubulin beta chain | TUBB4B; TUBB4A; TUBB | 7 |
| O15067 | Phosphoribosylformylglycinamidine synthase | PFAS | 7 |
| P35241 | Radixin | RDX | 7 |
| O60488 | Long-chain-fatty-acid--CoA ligase 4 | ACSL4 | 7 |
| A0A0C4DGX4 | Cullin-1 | CUL1 | 7 |
| P50148 | Guanine nucleotide-binding protein G(q) subunit alpha | GNAQ | 7 |
| Q15907 | Ras-related protein Rab-11B; Ras-related protein Rab-11A | RAB11B; RAB11A | 7 |
| P30086 | Phosphatidylethanolamine-binding protein 1; Hippocampal cholinergic neurostimulating peptide | PEBP1 | 6 |
| P55036 | 26S proteasome non-ATPase regulatory subunit 4 | PSMD4 | 6 |
| P28070 | Proteasome subunit beta type-4 | PSMB4 | 6 |
| Q9UNS2 | COP9 signalosome complex subunit 3 | COPS3 | 6 |
| P08754 | Guanine nucleotide-binding protein G(k) subunit alpha | GNAI3 | 6 |
| P61006 | Ras-related protein Rab-8A | RAB8A | 6 |
| P61019 | Ras-related protein Rab-2A | RAB2A | 6 |
| H0Y8C6 | Importin-5 | IPO5 | 6 |
| Q00577 | Transcriptional activator protein Pur-alpha | PURA | 6 |
| P52565 | Rho GDP-dissociation inhibitor 1 | ARHGDIA | 6 |
| Q9Y5Z4 | Heme-binding protein 2 | HEBP2 | 6 |
| J3KNF4 | Copper chaperone for superoxide dismutase; Superoxide dismutase [Cu—Zn] | CCS | 6 |
| A0A087WXS7 | ATPase ASNA1 | ASNA1 | 6 |
| P05089 | Arginase-1 | ARG1 | 6 |
| O95336 | 6-phosphogluconolactonase | PGLS | 6 |
| Q92508 | Piezo-type mechanosensitive ion channel component 1 | PIEZO1 | 6 |
| P84077 | ADP-ribosylation factor 1; ADP-ribosylation factor 3 | ARF1; ARF3 | 6 |
| P21281 | V-type proton ATPase subunit B, brain isoform; V-type proton ATPase subunit B, kidney isoform | ATP6V1B2; ATP6V1B1 | 6 |
| P04259 | Keratin, type II cytoskeletal 6B | KRT6B | 6 |
| Q92905 | COP9 signalosome complex subunit 5 | COPS5 | 6 |
| P61163 | Alpha-centractin | ACTR1A | 6 |
| O95373 | Importin-7 | IPO7 | 6 |
| C9JD73 | Protein phosphatase 1 regulatory subunit 7 | PPP1R7 | 6 |
| Q99536 | Synaptic vesicle membrane protein VAT-1 homolog | VAT1 | 6 |
| Q86UX7 | Fermitin family homolog 3 | FERMT3 | 6 |
| C9JFE4 | COP9 signalosome complex subunit 1 | GPS1 | 6 |
| P36959 | GMP reductase 1 | GMPR | 6 |
| B5MDF5 | GTP-binding nuclear protein Ran | RAN | 6 |
| F5GY90 | Porphobilinogen deaminase | HMBS | 6 |
| E7EX90 | Dynactin subunit 1 | DCTN1 | 6 |

TABLE 4-continued

Proteins identified in the EEV proteome. Lists of the proteins identified by LC-MS/MS analysis using Andromeda™/MaxQuant™ search engine in the Uniprot Complete Proteome Homo sapiens database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| H0Y512 | Adipocyte plasma membrane-associated protein | APMAP | 6 |
| Q32Q12 | Nucleoside diphosphate kinase; Nucleoside diphosphate kinase B; Putative nucleoside diphosphate kinase | NME1-NME2; NME2; NME1; NME2P1 | 6 |
| P13807 | Glycogen [starch] synthase, muscle | GYS1 | 6 |
| K7ES02 | Bleomycin hydrolase | BLMH | 6 |
| P17213 | Bactericidal permeability-increasing protein | BPI | 6 |
| Q9UNM6 | 26S proteasome non-ATPase regulatory subunit 13 | PSMD13 | 6 |
| J3KQ32 | Obg-like ATPase 1 | OLA1 | 6 |
| Q9Y490 | Talin-1 | TLN1 | 6 |
| H0YD13 | CD44 antigen | CD44 | 6 |
| P18669 | Phosphoglycerate mutase 1; Phosphoglycerate mutase 2; Probable phosphoglycerate mutase 4 | PGAM1; PGAM2; PGAM4 | 6 |
| P23528 | Cofilin-1 | CFL1 | 6 |
| Q5SR44 | Complement receptor type 1 | CR1 | 6 |
| Q99436 | Proteasome subunit beta type-7 | PSMB7 | 6 |
| P47756 | F-actin-capping protein subunit beta | CAPZB | 6 |
| P30740 | Leukocyte elastase inhibitor | SERPINB1 | 6 |
| A0A024R571 | EH domain-containing protein 1 | EHD1 | 6 |
| P30043 | Flavin reductase (NADPH) | BLVRB | 6 |
| P32119 | Peroxiredoxin-2 | PRDX2 | 6 |
| C9J0K6 | Sorcin | SRI | 6 |
| P27105 | Erythrocyte band 7 integral membrane protein | STOM | 6 |
| P84077 | ADP-ribosylation factor 1; ADP-ribosylation factor 3; ADP-ribosylation factor 5; ADP-ribosylation factor 4 | ARF1; ARF3; ARF5; ARF4 | 6 |
| P61981 | 14-3-3 protein gamma; 14-3-3 protein gamma, N-terminally processed | YWHAG | 5 |
| P09211 | Glutathione S-transferase P | GSTP1 | 5 |
| P13489 | Ribonuclease inhibitor | RNH1 | 5 |
| Q96PU5 | E3 ubiquitin-protein ligase NEDD4-like | NEDD4L | 5 |
| Q5SRN7 | HLA class I histocompatibility antigen, A; HLA class I histocompatibility antigen, B; HLA class I histocompatibility antigen, Cw | HLA-A; HLA-C; HLA-B | 5 |
| P02042 | Hemoglobin subunit delta | HBD | 5 |
| A0A087WU29 | Glycophorin-A | GYPA | 5 |
| P00390 | Glutathione reductase, mitochondrial | GSR | 5 |
| Q9UBV8 | Peflin | PEF1 | 5 |
| Q8WVM8 | Sec1 family domain-containing protein 1 | SCFD1 | 5 |
| F6TLX2 | Glyoxalase domain-containing protein 4 | GLOD4 | 5 |
| H3BQF1 | Adenine phosphoribosyltransferase | APRT | 5 |
| Q07960 | Rho GTPase-activating protein 1 | ARHGAP1 | 5 |
| F6XSS0 | Blood group Rh(CE) polypeptide; Blood group Rh(D) polypeptide | RHCE; RHD | 5 |
| A0A087WY55 | Vacuolar protein sorting-associated protein VTA1 homolog | VTA1 | 5 |
| G5E9W8 | Glycogenin-1 | GYG1 | 5 |
| P07451 | Carbonic anhydrase 3 | CA3 | 5 |
| Q08722 | Leukocyte surface antigen CD47 | CD47 | 5 |
| X6RA14 | S-formylglutathione hydrolase | ESD | 5 |
| Q8IUI8 | Cytokine receptor-like factor 3 | CRLF3 | 5 |
| Q5VW32 | BRO1 domain-containing protein BROX | BROX | 5 |
| P61026 | Ras-related protein Rab-10 | RAB10 | 5 |
| A0A087WWY3 | Filamin-A | FLNA | 5 |
| H0YGX7 | Rho GDP-dissociation inhibitor 2 | ARHGDIB | 5 |
| Q92783 | Signal transducing adapter molecule 1 | STAM | 5 |
| Q7Z6Z7 | E3 ubiquitin-protein ligase HUWE1 | HUWE1 | 5 |
| H0YHC3 | Nucleosome assembly protein 1-like 1 | NAP1L1 | 5 |
| Q5QPM7 | Proteasome inhibitor PI31 subunit | PSMF1 | 5 |
| P09104 | Gamma-enolase; Enolase | ENO2 | 5 |
| Q5T2B5 | Cullin-2 | CUL2 | 5 |
| Q8WW22 | DnaJ homolog subfamily A member 4 | DNAJA4 | 5 |
| P61201 | COP9 signalosome complex subunit 2 | COPS2 | 5 |
| X6R433 | Protein-tyrosine-phosphatase; Receptor-type tyrosine-protein phosphatase C | PTPRC | 5 |
| P63000 | Ras-related C3 botulinum toxin substrate 1 | RAC1 | 5 |
| F5GXM3 | IST1 homolog | IST1 | 5 |
| H3BLU7 | Aflatoxin B1 aldehyde reductase member 2 | AKR7A2 | 5 |
| P25325 | 3-mercaptopyruvate sulfurtransferase; Sulfurtransferase | MPST | 5 |
| A0A087X0K1 | Calcium-binding protein 39 | CAB39 | 5 |
| P23381 | Tryptophan--tRNA ligase, cytoplasmic; T1-TrpRS; T2-TrpRS | WARS | 5 |
| P01116 | GTPase KRas; GTPase KRas, N-terminally processed | KRAS | 5 |
| P30040 | Endoplasmic reticulum resident protein 29 | ERP29 | 5 |
| P05198 | Eukaryotic translation initiation factor 2 subunit 1 | EIF2S1 | 5 |
| Q6UX06 | Olfactomedin-4 | OLFM4 | 5 |
| Q96KP4 | Cytosolic non-specific dipeptidase | CNDP2 | 5 |
| Q04760 | Lactoylglutathione lyase | GLO1 | 5 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| J3QS39 | Ubiquitin-60S ribosomal protein L40; Ubiquitin; 60S ribosomal protein L40; Ubiquitin-40S ribosomal protein S27a; Ubiquitin; 40S ribosomal protein S27a; Polyubiquitin-B; Ubiquitin; Polyubiquitin-C; Ubiquitin | UBB; RPS27A; UBC; UBA52; UBBP4 | 5 |
| P06702 | Protein S100-A9 | S100A9 | 5 |
| P15531 | Nucleoside diphosphate kinase A; Nucleoside diphosphate kinase; Nucleoside diphosphate kinase B | NME1; NME2; NME1-NME2 | 5 |
| E7EV99 | Alpha-adducin | ADD1 | 5 |
| P51149 | Ras-related protein Rab-7a | RAB7A | 4 |
| K7N7A8 | Aquaporin-1 | AQP1 | 4 |
| P61020 | Ras-related protein Rab-5B | RAB5B | 4 |
| X6R4N5 | Erythroid membrane-associated protein | ERMAP | 4 |
| E5RJR5 | S-phase kinase-associated protein 1 | SKP1 | 4 |
| Q9Y315 | Deoxyribose-phosphate aldolase | DERA | 4 |
| X6R8F3 | Neutrophil gelatinase-associated lipocalin | LCN2 | 4 |
| O75396 | Vesicle-trafficking protein SEC22b | SEC22B | 4 |
| Q15102 | Platelet-activating factor acetylhydrolase IB subunit gamma | PAFAH1B3 | 4 |
| P51665 | 26S proteasome non-ATPase regulatory subunit 7 | PSMD7 | 4 |
| Q96FZ7 | Charged multivesicular body protein 6 | CHMP6 | 4 |
| Q9NRQ2 | Phospholipid scramblase 4 | PLSCR4 | 4 |
| F8VWS0 | 60S acidic ribosomal protein P0; 60S acidic ribosomal protein P0-like | RPLP0; RPLP0P6 | 4 |
| O14964 | Hepatocyte growth factor-regulated tyrosine kinase substrate | HGS | 4 |
| A0A0A0MTJ9 | Neutral cholesterol ester hydrolase 1 | NCEH1 | 4 |
| A0A087WY82 | Junctional adhesion molecule A | F11R | 4 |
| J3QSB7 | Purine nucleoside phosphorylase; S-methyl-5-thioadenosine phosphorylase | MTAP | 4 |
| Q5WQ6 | Ubiquitin thioesterase OTU1 | YOD1 | 4 |
| P36543 | V-type proton ATPase subunit E 1 | ATP6V1E1 | 4 |
| Q9BS40 | Latexin | LXN | 4 |
| P47755 | F-actin-capping protein subunit alpha-2 | CAPZA2 | 4 |
| Q9GZT8 | NIF3-like protein 1 | NIF3L1 | 4 |
| H6UYS7 | Alpha-synuclein | SNCA | 4 |
| P60953 | Cell division control protein 42 homolog | CDC42 | 4 |
| Q14773 | Intercellular adhesion molecule 4 | ICAM4 | 4 |
| H0Y6T7 | Nicastrin | NCSTN | 4 |
| P69891 | Hemoglobin subunit gamma-1 | HBG1 | 4 |
| P14625 | Endoplasmin | HSP90B1 | 4 |
| Q96GD0 | Pyridoxal phosphate phosphatase | PDXP | 4 |
| P08311 | Cathepsin G | CTSG | 4 |
| Q9H9Q2 | COP9 signalosome complex subunit 7b | COPS7B | 4 |
| P09417 | Dihydropteridine reductase | QDPR | 4 |
| F8WE6 | Peptidyl-prolyl cis-trans isomerase; Peptidyl-prolyl cis-trans isomerase A | PPIA | 4 |
| O15173 | Membrane-associated progesterone receptor component 2 | PGRMC2 | 4 |
| P28072 | Proteasome subunit beta type-6; Proteasome subunit beta type | PSMB6 | 4 |
| H3BSW0 | Leucine-rich repeat-containing protein 57 | LRRC57 | 4 |
| Q9UBW8 | COP9 signalosome complex subunit 7a | COPS7A | 4 |
| O00560 | Syntenin-1 | SDCBP | 4 |
| F5H157 | Ras-related protein Rab-35 | RAB35 | 4 |
| Q9H479 | Fructosamine-3-kinase | FN3K | 4 |
| Q04917 | 14-3-3 protein eta | YWHAH | 4 |
| C9JJ47 | AP-2 complex subunit mu | AP2M1 | 4 |
| C9JIG9 | Serine/threonine-protein kinase OSR1 | OXSR1 | 4 |
| Q13336 | Urea transporter 1 | SLC14A1 | 4 |
| P46926 | Glucosamine-6-phosphate isomerase 1; Glucosamine-6-phosphate isomerase; Glucosamine-6-phosphate isomerase 2 | GNPDA1; GNPDA2 | 4 |
| O43633 | Charged multivesicular body protein 2a | CHMP2A | 4 |
| F8VVB9 | Tubulin alpha-1A chain; Tubulin alpha-1C chain; Tubulin alpha-1B chain; Tubulin alpha-3C/D chain; Tubulin alpha-3E chain | TUBA1B; TUBA1C; TUBA1A; TUBA3C; TUBA3E | 4 |
| A6PVN5 | Serine/threonine-protein phosphatase 2A activator | PPP2R4 | 4 |
| B8ZZB8 | CB1 cannabinoid receptor-interacting protein 1 | CNRIP1 | 4 |
| Q9P2R3 | Rabankyrin-5 | ANKFY1 | 4 |
| Q86YS7 | C2 domain-containing protein 5 | C2CD5 | 4 |
| R4GMR5 | 26S proteasome non-ATPase regulatory subunit 8 | PSMD8 | 4 |
| E7EM64 | COP9 signalosome complex subunit 6 | COPS6 | 4 |
| J3KNI6 | Integrin beta; Integrin beta-2 | ITGB2 | 4 |
| H0Y5R6 | Uroporphyrinogen decarboxylase | UROD | 4 |
| M0R165 | Epidermal growth factor receptor substrate 15-like 1 | EPS15L1 | 4 |
| O00487 | 26S proteasome non-ATPase regulatory subunit 14 | PSMD14 | 4 |
| Q13630 | GDP-L-fucose synthase | TSTA3 | 4 |
| P55060 | Exportin-2 | CSE1L | 4 |
| P20020 | Plasma membrane calcium-transporting ATPase 1; Calcium-transporting ATPase | ATP2B1 | 4 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
| --- | --- | --- | --- |
| Q9NYU2 | UDP-glucose: glycoprotein glucosyltransferase 1 | UGGT1 | 4 |
| H3BND8 | Ubiquitin carboxyl-terminal hydrolase; Ubiquitin carboxyl-terminal hydrolase 7 | USP7 | 4 |
| Q9GZP4 | PITH domain-containing protein 1 | PITHD1 | 4 |
| D6RD66 | WD repeat-containing protein 1 | WDR1 | 4 |
| P48729 | Casein kinase I isoform alpha | CSNK1A1 | 4 |
| P25685 | DnaJ homolog subfamily B member 1 | DNAJB1 | 4 |
| P14550 | Alcohol dehydrogenase [NADP(+)] | AKR1A1 | 4 |
| Q6PCE3 | Glucose 1,6-bisphosphate synthase | PGM2L1 | 4 |
| Q9UPN7 | Serine/threonine-protein phosphatase 6 regulatory subunit 1 | PPP6R1 | 4 |
| P62805 | Histone H4 | HIST1H4A | 4 |
| P62937 | Peptidyl-prolyl cis-trans isomerase A | PPIA | 4 |
| P30046 | D-dopachrome decarboxylase; D-dopachrome decarboxylase-like protein | DDT; DDTL | 4 |
| Q08495 | Dematin | DMTN | 4 |
| K7EIJ0 | WW domain-binding protein 2 | WBP2 | 4 |
| E5RHP7 | Carbonic anhydrase 1 | CA1 | 4 |
| P09105 | Hemoglobin subunit theta-1 | HBQ1 | 4 |
| E7ESC6 | Exportin-7 | XPO7 | 4 |
| P61225 | Ras-related protein Rap-2b; Ras-related protein Rap-2c; Ras-related protein Rap-2a | RAP2B; RAP2A; RAP2C | 4 |
| O15400 | Syntaxin-7 | STX7 | 3 |
| Q5VZR0 | Golgi-associated plant pathogenesis-related protein 1 | GLIPR2 | 3 |
| P40199 | Carcinoembryonic antigen-related cell adhesion molecule 6 | CEACAM6 | 3 |
| P27348 | 14-3-3 protein theta | YWHAG | 3 |
| P62820 | Ras-related protein Rab-1A | RAB1A | 3 |
| C9JEN3 | Protein lifeguard 3 | TMBIM1 | 3 |
| Q9UDX3 | SEC14-like protein 4 | SEC14L4 | 3 |
| Q9Y570 | Protein phosphatase methylesterase 1 | PPME1 | 3 |
| Q96GG9 | DCN1-like protein 1; DCN1-like protein | DCUN1D1 | 3 |
| B0YJC4 | Vimentin | VIM | 3 |
| Q86VN1 | Vacuolar protein-sorting-associated protein 36 | VPS36 | 3 |
| F8WFB9 | Endophilin-B2 | SH3GLB2 | 3 |
| A0A087WVQ9 | Elongation factor 1-alpha 1; Putative elongation factor 1-alpha-like 3 | EEF1A1; EEF1A1P5 | 3 |
| Q53TN4 | Cytochrome b reductase 1 | CYBRD1 | 3 |
| P10809 | 60 kDa heat shock protein, mitochondrial | HSPD1 | 3 |
| F5H7X1 | 26S proteasome non-ATPase regulatory subunit 9 | PSMD9 | 3 |
| E9PNW4 | CD59 glycoprotein | CD59 | 3 |
| E9PS74 | Solute carrier family 43 member 3 | SLC43A3 | 3 |
| P53985 | Monocarboxylate transporter 1 | SLC16A1 | 3 |
| Q8WWI5 | Choline transporter-like protein 1 | SLC44A1 | 3 |
| E9PIR7 | Thioredoxin reductase 1, cytoplasmic | TXNRD1 | 3 |
| Q5TD07 | Ribosyldihydronicotinamide dehydrogenase [quinone] | NQO2 | 3 |
| Q9UL25 | Ras-related protein Rab-21 | RAB21 | 3 |
| P27824 | Calnexin | CANX | 3 |
| U3KPS2 | Myeloblastin | PRTN3 | 3 |
| Q9UKU0 | Long-chain-fatty-acid--CoA ligase 6 | ACSL6 | 3 |
| P24666 | Low molecular weight phosphotyrosine protein phosphatase | ACP1 | 3 |
| H7C2G2 | NAD(P)(+)--arginine ADP-ribosyltransferase; Ecto-ADP-ribosyltransferase 4 | ART4 | 3 |
| I3L1K6 | Myosin light chain 4 | MYL4 | 3 |
| Q9UK41 | Vacuolar protein sorting-associated protein 28 homolog | VPS28 | 3 |
| Q9NUQ9 | Protein FAM49B | FAM49B | 3 |
| Q9UBQ7 | Glyoxylate reductase/hydroxypyruvate reductase | GRHPR | 3 |
| B8ZZG1 | MAGUK p55 subfamily member 6 | MPP6 | 3 |
| Q10567 | AP-1 complex subunit beta-1 | AP1B1 | 3 |
| O75387 | Large neutral amino acids transporter small subunit 3 | SLC43A1 | 3 |
| Q9BTU6 | Phosphatidylinositol 4-kinase type 2-alpha | PI4K2A | 3 |
| J3KS22 | L-xylulose reductase | DCXR | 3 |
| O15498 | Synaptobrevin homolog YKT6 | YKT6 | 3 |
| Q08211 | ATP-dependent RNA helicase A | DHX9 | 3 |
| P50416 | Carnitine O-palmitoyltransferase 1, liver isoform | CPT1A | 3 |
| P08237 | ATP-dependent 6-phosphofructokinase, muscle type | PFKM | 3 |
| P14735 | Insulin-degrading enzyme | IDE | 3 |
| Q9H0R3 | Transmembrane protein 222 | TMEM222 | 3 |
| Q14166 | Tubulin--tyrosine ligase-like protein 12 | TTLL12 | 3 |
| Q14558 | Phosphoribosyl pyrophosphate synthase-associated protein 1 | PRPSAP1 | 3 |
| A0A087WTB8 | Ubiquitin carboxyl-terminal hydrolase; Ubiquitin carboxyl-terminal hydrolase isozyme L3 | UCHL3 | 3 |
| Q9NPQ8 | Synembryn-A | RIC8A | 3 |
| F6WQW2 | Ran-specific GTPase-activating protein | RANBP1 | 3 |
| Q15691 | Microtubule-associated protein RP/EB family member 1 | MAPRE1 | 3 |
| A0A0A0MR50 | Cullin-4A | CUL4A | 3 |
| Q96IU4 | Alpha/beta hydrolase domain-containing protein 14B | ABHD14B | 3 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| Q9P0L0 | Vesicle-associated membrane protein-associated protein A | VAPA | 3 |
| E9PRY8 | Elongation factor 1-delta | EEF1D | 3 |
| Q16543 | Hsp90 co-chaperone Cdc37 | CDC37 | 3 |
| P06702 | Protein S100-A9 | S100A9 | 3 |
| P13639 | Elongation factor 2 | EEF2 | 3 |
| E9PJC7 | Tetraspanin; CD82 antigen | CD82 | 3 |
| Q01432 | AMP deaminase 3 | AMPD3 | 3 |
| B1AUU8 | Epidermal growth factor receptor substrate 15 | EPS15 | 3 |
| P54709 | Sodium/potassium-transporting ATPase subunit beta-3 | ATP1B3 | 3 |
| P54727 | UV excision repair protein RAD23 homolog B | RAD23B | 3 |
| P36507 | Dual specificity mitogen-activated protein kinase kinase 2 | MAP2K2 | 3 |
| Q9Y2V2 | Calcium-regulated heat stable protein 1 | CARHSP1 | 3 |
| P31146 | Coronin-1A; Coronin | CORO1A | 3 |
| Q8IY17 | Neuropathy target esterase | PNPLA6 | 3 |
| E7EQR4 | Ezrin | EZR | 3 |
| F8WDS9 | LanC-like protein 1 | LANCL1 | 3 |
| X6RJP6 | Transgelin-2 | TAGLN2 | 3 |
| A0A0J9YXM6 | WD repeat-containing protein 81 | WDR81 | 3 |
| P62140 | Serine/threonine-protein phosphatase PP1-beta catalytic subunit; Serine/threonine-protein phosphatase | PPP1CB | 3 |
| H0YLJ3 | Mortality factor 4-like protein 1 | MORF4L1 | 3 |
| E7EPV7 | Alpha-synuclein | SNCA | 3 |
| K7EK07 | Histone H3 | H3F3B | 3 |
| P05109 | Protein S100-A8; Protein S100-A8, N-terminally processed | S100A8 | 3 |
| I3L0A0 | Ubiquitin-conjugating enzyme E2 variant 1; Ubiquitin-conjugating enzyme E2 variant 2 | TMEM189-UBE2V1; UBE2V1; UBE2V2 | 3 |
| Q6B0K9 | Hemoglobin subunit mu | HBM | 3 |
| O75368 | SH3 domain-binding glutamic acid-rich-like protein | SH3BGRL | 3 |
| A0A0J9YXB3 | Ras-related protein Rap-1b; Ras-related protein Rap-1A; Ras-related protein Rap-1b-like protein | RAP1B; RAP1A | 3 |
| P60953 | Cell division control protein 42 homolog | CDC42 | 3 |
| A0A087WTI1 | Ras-related protein Rab-1B; Ras-related protein Rab-1A | RAB1B; RAB1A | 3 |
| B5MDF5 | GTP-binding nuclear protein Ran | RAN | 3 |
| P61088 | Ubiquitin-conjugating enzyme E2 N | UBE2N | 3 |
| Q00013 | 55 kDa erythrocyte membrane protein | MPP1 | 3 |
| B1AKQ8 | Guanine nucleotide-binding protein G(I)/G(S)/G(T) subunit beta-1; Guanine nucleotide-binding protein G(I)/G(S)/G(T) subunit beta-3; Guanine nucleotide-binding protein G(I)/G(S)/G(T) subunit beta-2 | GNB1; GNB2; GNB3 | 3 |
| P04406 | Glyceraldehyde-3-phosphate dehydrogenase | GAPDH | 3 |
| Q9UJC5 | SH3 domain-binding glutamic acid-rich-like protein 2 | SH3BGRL2 | 3 |
| P04921 | Glycophorin-C | GYPC | 2 |
| Q9NP59 | Solute carrier family 40 member 1 | SLC40A1 | 2 |
| K7EKH5 | Fructose-bisphosphate aldolase; Fructose-bisphosphate aldolase C | ALDOC | 2 |
| P11233 | Ras-related protein Ral-A | RALA | 2 |
| F8WBR5 | Calmodulin | CALM2; CALM3; CALM1 | 2 |
| P00441 | Superoxide dismutase [Cu—Zn] | SOD1 | 2 |
| H0YDI1 | Lymphocyte function-associated antigen 3 | CD58 | 2 |
| H0YNE9 | Ras-related protein Rab-8B | RAB8B | 2 |
| J3KN67 | | TPM3 | 2 |
| P20160 | Azurocidin | AZU1 | 2 |
| A0A087WZZ4 | Ammonium transporter Rh type A | RHAG | 2 |
| F5GXS0 | Complement C4-A; Complement C4-B | C4B; C4A | 2 |
| Q8ND76 | Cyclin-Y | CCNY | 2 |
| Q14739 | Lamin-B receptor | LBR | 2 |
| Q15181 | Inorganic pyrophosphatase | PPA1 | 2 |
| J3QS92 | Galectin-9 | LGALS9 | 2 |
| I3L471 | Phosphatidylinositol transfer protein alpha isoform | PITPNA | 2 |
| P01111 | GTPase NRas | NRAS; KRAS | 2 |
| F5H4Q5 | Vacuolar protein sorting-associated protein 37C | VPS37C | 2 |
| A0A0A0MSW4 | Phosphatidylinositol transfer protein beta isoform | PITPNB | 2 |
| P67775 | Serine/threonine-protein phosphatase 2A catalytic subunit alpha isoform; Serine/threonine-protein phosphatase | PPP2CA; PPP2CB | 2 |
| P41091 | Eukaryotic translation initiation factor 2 subunit 3; Putative eukaryotic translation initiation factor 2 subunit 3-like protein | EIF2S3; EIF2S3L | 2 |
| A0A087WWS7 | Syntaxin-binding protein 2 | STXBP2 | 2 |
| F8VQX6 | Methyltransferase-like protein 7A | METTL7A | 2 |
| B3KT28 | FAS-associated factor 1 | FAF1 | 2 |
| K7EIJ8 | Katanin p60 ATPase-containing subunit A-like 2 | KATNAL2 | 2 |

TABLE 4-continued

Proteins identified in the EEV proteome. Lists of the proteins identified by LC-MS/MS analysis using Andromeda ™/MaxQuant ™ search engine in the Uniprot Complete Proteome Homo sapiens database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P20339 | Ras-related protein Rab-5A | RAB5A | 2 |
| O95456 | Proteasome assembly chaperone 1 | PSMG1 | 2 |
| K7EK45 | Polypyrimidine tract-binding protein 1 | PTBP1 | 2 |
| Q15365 | Poly(rC)-binding protein 1; Poly(rC)-binding protein 3 | PCBP1; PCBP3 | 2 |
| Q9BSJ8 | Extended synaptotagmin-1 | ESYT1 | 2 |
| H3BP35 | Diphosphomevalonate decarboxylase | MVD | 2 |
| H0Y8C4 | Serine/threonine-protein phosphatase 2A 56 kDa regulatory subunit delta isoform | PPP2R5D | 2 |
| K7EP09 | Bifunctional coenzyme A synthase; Phosphopantetheine adenylyltransferase; Dephospho-CoA kinase | COASY | 2 |
| F8VNT9 | Tetraspanin; CD63 antigen | CD63 | 2 |
| Q8NEV1 | Casein kinase II subunit alpha 3; Casein kinase II subunit alpha | CSNK2A3; CSNK2A1 | 2 |
| F8VTQ5 | Heterogeneous nuclear ribonucleoprotein A1 | HNRNPA1 | 2 |
| A0A087X2E2 | Carcinoembryonic antigen-related cell adhesion molecule 8; Carcinoembryonic antigen-related cell adhesion molecule 1; Carcinoembryonic antigen-related cell adhesion molecule 5 | CEACAM8; CEACAM5; CEACAM1 | 2 |
| H0YAS8 | Clusterin; Clusterin beta chain; Clusterin alpha chain; Clusterin | CLU | 2 |
| E9PP54 | Tubulin-specific chaperone cofactor E-like protein | TBCEL | 2 |
| P43034 | Platelet-activating factor acetylhydrolase IB subunit alpha | PAFAH1B1 | 2 |
| Q9NT62 | Ubiquitin-like-conjugating enzyme ATG3 | ATG3 | 2 |
| K7ERZ3 | Perilipin-3 | PLIN3 | 2 |
| Q6DD88 | Atlastin-3 | ATL3 | 2 |
| Q15084-3 | Protein disulfide-isomerase A6 | PDIA6 | 2 |
| K7EQH4 | ATP synthase subunit alpha, mitochondrial | ATP5A1 | 2 |
| G3V1U5 | Vesicle transport protein GOT1B | GOLT1B | 2 |
| O00186 | Syntaxin-binding protein 3 | STXBP3 | 2 |
| Q5T6W2 | Heterogeneous nuclear ribonucleoprotein K | HNRNPK | 2 |
| H0YEY4 | ADP-sugar pyrophosphatase | NUDT5 | 2 |
| P35580 | Myosin-10 | MYH10 | 2 |
| F5H081 | Solute carrier family 2, facilitated glucose transporter member 4 | SLC2A4 | 2 |
| Q9H1C7 | Cysteine-rich and transmembrane domain-containing protein 1 | CYSTM1 | 2 |
| K7EJ83 | Cyclin-dependent kinase 2; Cyclin-dependent kinase 3 | CDK3; CDK2 | 2 |
| C9J352 | Importin subunit alpha-5; Importin subunit alpha-5, N-terminally processed | KPNA1 | 2 |
| H9KV75 | Alpha-actinin-1; Alpha-actinin-4; Alpha-actinin-2; Alpha-actinin-3 | ACTN1; ACTN4; ACTN3; ACTN2 | 2 |
| A0A0A0MQS1 | Pyrroline-5-carboxylate reductase; Pyrroline-5-carboxylate reductase 3 | PYCRL | 2 |
| D6RBY0 | Rieske domain-containing protein | RFESD | 2 |
| C9JC71 | Low affinity immunoglobulin gamma Fc region receptor III-A | FCGR3A | 2 |
| P51811 | Membrane transport protein XK | XK | 2 |
| C9J1G2 | DnaJ homolog subfamily B member 2 | DNAJB2 | 2 |
| Q9UN37 | Vacuolar protein sorting-associated protein 4A; Vacuolar protein sorting-associated protein 4B; Fidgetin-like protein 1 | VPS4A; VPS4B; FIGNL1 | 2 |
| P61160 | Actin-related protein 2 | ACTR2 | 2 |
| P16930 | Fumarylacetoacetase | FAH | 2 |
| A0A087X0K4 | CUB and sushi domain-containing protein 2 | CSMD2 | 2 |
| P10746 | Uroporphyrinogen-III synthase | UROS | 2 |
| K7EQ02 | DAZ-associated protein 1 | DAZAP1 | 2 |
| F5GYN4 | Ubiquitin thioesterase OTUB1 | OTUB1 | 2 |
| P10599 | Thioredoxin | TXN | 2 |
| O95197 | Reticulon-3 | RTN3 | 2 |
| E7ETB3 | Aspartyl aminopeptidase | DNPEP | 2 |
| P14868 | Aspartate--tRNA ligase, cytoplasmic | DARS | 2 |
| Q08AM6 | Protein VAC14 homolog | VAC14 | 2 |
| Q93034 | Cullin-5 | CUL5 | 2 |
| Q9BQA1 | Methylosome protein 50 | WDR77 | 2 |
| A0A0B4J2G9 | Ubiquitin-conjugating enzyme E2 L3 | UBE2L3 | 2 |
| Q04446 | 1,4-alpha-glucan-branching enzyme | GBE1 | 2 |
| Q96NA2 | Rab-interacting lysosomal protein | RILP | 2 |
| Q92539 | Phosphatidate phosphatase LPIN2 | LPIN2 | 2 |
| P28482 | Mitogen-activated protein kinase 1 | MAPK1 | 2 |
| Q7Z406 | Myosin-14; Myosin-11 | MYH14; 11 | 2 |
| Q8IU68 | Transmembrane channel-like protein 8 | TMC8 | 2 |
| Q96BJ3 | Axin interactor, dorsalization-associated protein | AIDA | 2 |
| P20042 | Eukaryotic translation initiation factor 2 subunit 2 | EIF2S2 | 2 |
| A0A0A0MQR0 | Docosahexaenoic acid omega-hydroxylase CYP4F3; Phylloquinone omega-hydroxylase CYP4F2; Cytochrome P450 4F12; Phylloquinone omega-hydroxylase CYP4F11 | CYP4F2; CYP4F3; CYP4F11; CYP4F12 | 2 |
| Q9BS26 | Endoplasmic reticulum resident protein 44 | ERP44 | 2 |
| O00178 | GTP-binding protein 1 | GTPBP1 | 2 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
| --- | --- | --- | --- |
| P27797 | Calreticulin | CALR | 2 |
| G3V0E5 | Transferrin receptor protein 1; Transferrin receptor protein 1, serum form | TFRC | 2 |
| P48147 | Prolyl endopeptidase | PREP | 2 |
| H7BZC1 | Hippocalcin-like protein 1; Neuron-specific calcium-binding protein hippocalcin; Neurocalcin-delta | HPCAL1; NCALD; HPCA | 2 |
| F8VPD4 | CAD protein; Glutamine-dependent carbamoyl-phosphate synthase; Aspartate carbamoyltransferase; Dihydroorotase | CAD | 2 |
| Q9NTJ5 | Phosphatidylinositide phosphatase SAC1 | SACM1L | 2 |
| P26447 | Protein S100-A4 | S100A4 | 2 |
| Q9UIW2 | Plexin-A1 | PLXNA1 | 2 |
| H0YJS0 | V-type proton ATPase subunit D | ATP6V1D | 2 |
| P25445 | Tumor necrosis factor receptor superfamily member 6 | FAS | 2 |
| C9JEU5 | Fibrinogen gamma chain | FGG | 2 |
| F5H562 | Copper-transporting ATPase 2; WND/140 kDa | ATP7B | 2 |
| B5MCF3 | Protein GUCD1 | GUCD1 | 2 |
| Q96TA1 | Niban-like protein 1 | FAM129B | 2 |
| F5GWT4 | Serine/threonine-protein kinase WNK1 | WNK1 | 2 |
| E9PLT1 | Platelet glycoprotein 4 | CD36 | 2 |
| Q8TDB8 | Solute carrier family 2, facilitated glucose transporter member 14; Solute carrier family 2, facilitated glucose transporter member 3 | SLC2A14; SLC2A3 | 2 |
| B4DDD6 | Drebrin-like protein | DBNL | 2 |
| E9PII3 | Band 4.1-like protein 2 | EPB41L2 | 2 |
| E9PNF5 | Glutamine-dependent NAD(+) synthetase | NADSYN1 | 2 |
| K7ELL7 | Glucosidase 2 subunit beta | PRKCSH | 2 |
| Q9BV20 | Methylthioribose-1-phosphate isomerase | MRI1 | 2 |
| J3KNB4 | Cathelicidin antimicrobial peptide; Antibacterial protein FALL-39; Antibacterial protein LL-37 | CAMP | 2 |
| Q5T1Z0 | Phospholysine phosphohistidine inorganic pyrophosphate phosphatase | LHPP | 2 |
| H3BLV0 | Complement decay-accelerating factor | CD55 | 2 |
| Q9Y3E7 | Charged multivesicular body protein 3 | CHMP3 | 2 |
| Q5T6H7 | Xaa-Pro aminopeptidase 1 | XPNPEP1 | 2 |
| O94779 | Contactin-5 | CNTN5 | 2 |
| E9PNR2 | Ras and Rab interactor 1 | RIN1 | 2 |
| E7ESJ7 | Protein FAM114A2 | FAM114A2 | 2 |
| A0A0A0MS99 | Multidrug resistance-associated protein 1 | ABCC1 | 2 |
| A0A0G2JM15 | Large neutral amino acids transporter small subunit 4 | SLC43A2 | 2 |
| H0YBF7 | Arf-GAP with SH3 domain, ANK repeat and PH domain-containing protein 1; Arf-GAP with SH3 domain, ANK repeat and PH domain-containing protein 2 | ASAP1; ASAP2 | 2 |
| P29992 | Guanine nucleotide-binding protein subunit alpha-11 | GNA11 | 2 |
| F8WF69 | Clathrin light chain A | CLTA | 2 |
| B5MCN0 | Atlastin-2 | ATL2 | 2 |
| F8W9F9 | Serine/threonine-protein kinase WNK2; Serine/threonine-protein kinase WNK3 | WNK2; WNK3 | 2 |
| A2A3F3 | Transient receptor potential cation channel subfamily M member 3 | TRPM3 | 2 |
| Q5KU26 | Collectin-12 | COLEC12 | 2 |
| O14523 | C2 domain-containing protein 2-like | C2CD2L | 2 |
| Q96DG6 | Carboxymethylenebutenolidase homolog | CMBL | 2 |
| Q5THJ4 | Vacuolar protein sorting-associated protein 13D | VPS13D | 2 |
| Q02790 | Peptidyl-prolyl cis-trans isomerase FKBP4; Peptidyl-prolyl cis-trans isomerase FKBP4, N-terminally processed | FKBP4 | 2 |
| A0A0G2JQD2 | Glutathione S-transferase theta-1 | GSTT1 | 2 |
| Q9NV96 | Cell cycle control protein 50A; Cell cycle control protein 50B | TMEM30A; TMEM30B | 2 |
| P62330 | ADP-ribosylation factor 6 | ARF6 | 2 |
| Q9UPU5 | Ubiquitin carboxyl-terminal hydrolase 24 | USP24 | 2 |
| B2R4S9 | Histone H2B | HIST1H2BI | 2 |
| P10599 | Thioredoxin | TXN | 2 |
| R4GN98 | Protein S100; Protein S100-A6 | S100A6 | 2 |
| H3BS66 | Small integral membrane protein 1 | SMIM1 | 2 |
| Q8NHG7 | Small VCP/p97-interacting protein | SVIP | 2 |
| C9JIG9 | Serine/threonine-protein kinase OSR1; STE20/SPS1-related proline-alanine-rich protein kinase | OXSR1; STK39 | 2 |
| Q5VZR0 | Golgi-associated plant pathogenesis-related protein 1 | GLIPR2 | 2 |
| F8WD49 | Anion exchange protein 3; Anion exchange protein; Anion exchange protein 2 | SLC4A3; SLC4A2 | 2 |
| P61626 | Lysozyme C; Lysozyme | LYZ | 2 |
| Q5T123 | SH3 domain-binding glutamic acid-rich-like protein 3 | SH3BGRL3 | 2 |
| F5H571 | Ubiquitin carboxyl-terminal hydrolase 5 | USP5 | 2 |
| Q9H3K6 | BolA-like protein 2 | BOLA2; BOLA2B | 2 |
| P05164 | Myeloperoxidase; Myeloperoxidase; 89 kDa myeloperoxidase; 84 kDa myeloperoxidase; Myeloperoxidase light chain; Myeloperoxidase heavy chain | MPO | 2 |

TABLE 4-continued

Proteins identified in the EEV proteome. Lists of the proteins identified by LC-MS/MS analysis using Andromeda™/MaxQuant™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| P50395 | Rab GDP dissociation inhibitor beta | GDI2 | 2 |
| G3V2U7 | Acylphosphatase; Acylphosphatase-1 | ACYP1 | 2 |
| J3KNB4 | Cathelicidin antimicrobial peptide; Antibacterial protein FALL-39; Antibacterial protein LL-37 | CAMP | 2 |
| H0Y9X3 | Programmed cell death protein 6 | PDCD6 | 2 |
| A6NJA2 | Ubiquitin carboxyl-terminal hydrolase; Ubiquitin carboxyl-terminal hydrolase 14 | USP14 | 2 |
| P35998 | 26S protease regulatory subunit 7 | PSMC2 | 2 |
| P30041 | Peroxiredoxin-6 | PRDX6 | 2 |
| P35612 | Beta-adducin | ADD2 | 2 |
| P00918 | Carbonic anhydrase 2 | CA2 | 2 |
| A0A0C4DGH5 | Cullin-associated NEDD8-dissociated protein 1 | CAND1 | 2 |
| C9JZN1 | Guanine nucleotide-binding protein G(I)/G(S)/G(T) subunit beta-2; Guanine nucleotide-binding protein subunit beta-4 | GNB2; GNB4 | 1 |
| I3L4X8 | Integrin beta; Integrin beta-3 | ITGB3 | 1 |
| H7BZJ3 | | PDIA3 | 1 |
| P17066 | Heat shock 70 kDa protein 6; Putative heat shock 70 kDa protein 7 | HSPA6; HSPA7 | 1 |
| J3KT70 | Arf-GAP with dual PH domain-containing protein 2 | ADAP2; CENTA2 | 1 |
| Q9Y6M5 | Zinc transporter 1 | SLC30A1 | 1 |
| P54725 | UV excision repair protein RAD23 homolog A | RAD23A | 1 |
| F8WD59 | 40S ribosomal protein SA | RPSA; RPSAP58 | 1 |
| P06753 | | | 1 |
| E9PMI6 | Methylosome subunit pICln | CLNS1A | 1 |
| Q9BVK6 | Transmembrane emp24 domain-containing protein 9 | TMED9 | 1 |
| C9JJV6 | Myeloid-associated differentiation marker | MYADM | 1 |
| Q8IXQ3 | Uncharacterized protein C9orf40 | C9orf40 | 1 |
| Q8NDC0 | MAPK-interacting and spindle-stabilizing protein-like | MAPK1IP1L | 1 |
| Q99747 | Gamma-soluble NSF attachment protein | NAPG | 1 |
| E7EWE1 | Ubiquitin-like modifier-activating enzyme 5 | UBA5 | 1 |
| J3KNE3 | Platelet-activating factor acetylhydrolase IB subunit beta | PAFAH1B2 | 1 |
| Q8IUI8 | Cytokine receptor-like factor 3 | CRLF3 | 1 |
| Q9BTX7 | Alpha-tocopherol transfer protein-like | TTPAL | 1 |
| P63261 | Actin, cytoplasmic 2; Actin, cytoplasmic 2, N-terminally processed | ACTG1 | 1 |
| P31153 | S-adenosylmethionine synthase isoform type-2 | MAT2A | 1 |
| O00560 | Syntenin-1 | SDCBP | 1 |
| Q4VB86 | Protein 4.1 | EPB41 | 1 |
| Q8WUD1 | Ras-related protein Rab-2B | RAB2B; DKFZp313C1541 | 1 |
| Q9NWV4 | UPF0587 protein C1orf123 | C1orf123 | 1 |
| Q9Y2Z0 | Suppressor of G2 allele of SKP1 homolog | SUGT1 | 1 |
| H0YK48 | Tropomyosin alpha-1 chain | TPM1 | 1 |
| H3BS66 | Small integral membrane protein 1 | SMIM1 | 1 |
| Q5VTS0 | Neurensin-1 | NRSN1 | 1 |
| H0Y904 | Multidrug resistance-associated protein 7 | ABCC10 | 1 |
| P08F94 | Fibrocystin | PKHD1 | 1 |
| G3V5X4 | Nesprin-2 | SYNE2 | 1 |
| P48507 | Glutamate--cysteine ligase regulatory subunit | GCLM | 1 |
| H3BUF4 | Cyclin-D1-binding protein 1 | CCNDBP1 | 1 |
| F8WB30 | Target of Myb protein 1 | TOM1 | 1 |
| E5RJI8 | | CA1 | 1 |
| S4R3E5 | Importin subunit alpha-7 | KPNA6 | 1 |
| E7EVS6 | | ACTB | 1 |
| P04206 | Ig kappa chain V-III region GOL; Ig kappa chain V-III region WOL; Ig kappa chain V-III region Ti; Ig kappa chain V-III region SIE | | 1 |
| Q5SSV3 | N(G),N(G)-dimethylarginine dimethylaminohydrolase 2 | DDAH2 | 1 |
| H0YG54 | Oligoribonuclease, mitochondrial | REXO2 | 1 |
| P08246 | Neutrophil elastase | ELANE | 1 |
| P40926 | Malate dehydrogenase, mitochondrial | MDH2 | 1 |
| P98172 | Ephrin-B1 | EFNB1 | 1 |
| Q96DD7 | Protein shisa-4 | SHISA4 | 1 |
| Q71RC9 | Small integral membrane protein 5 | SMIM5 | 1 |
| P68133 | Actin, alpha skeletal muscle; Actin, alpha cardiac muscle 1; Actin, gamma-enteric smooth muscle; Actin, aortic smooth muscle | ACTA1; ACTC1; ACTG2; ACTA2 | 1 |
| H0Y9Q6 | Clathrin light chain B | CLTB | 1 |
| G3V5P0 | | KTN1 | 1 |
| Q9NWX6 | Probable tRNA(His) guanylyltransferase | THG1L | 1 |
| Q15404 | Ras suppressor protein 1 | RSU1 | 1 |
| B2R4S9 | Histone H2B | HIST1H2B | 1 |
| K7EK06 | Phenylalanine--tRNA ligase alpha subunit | FARSA | 1 |
| H7C3S9 | COP9 signalosome complex subunit 8 | COPS8 | 1 |

TABLE 4-continued

Proteins identified in the EEV proteome. Lists of the proteins identified by LC-MS/MS analysis using Andromeda™/MaxQuant™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
|---|---|---|---|
| J3KRV4 | Dual specificity mitogen-activated protein kinase kinase 3 | MAP2K3 | 1 |
| Q15042 | Rab3 GTPase-activating protein catalytic subunit | RAB3GAP1 | 1 |
| P01893 | Putative HLA class I histocompatibility antigen, alpha chain H; HLA class I histocompatibility antigen, Cw-6 alpha chain; HLA class I histocompatibility antigen, B-38 alpha chain; HLA class I histocompatibility antigen, B-67 alpha chain; HLA class I histocompatibility antigen, B-82 alpha chain; HLA class I histocompatibility antigen, B-39 alpha chain; HLA class I histocompatibility antigen, Cw-18 alpha chain; HLA class I histocompatibility antigen, Cw-7 alpha chain; HLA class I histocompatibility antigen, B-42 alpha chain; HLA class I histocompatibility antigen, B-14 alpha chain; HLA class I histocompatibility antigen, B-8 alpha chain; HLA class I histocompatibility antigen, B-7 alpha chain | HLA-H; HLA-C; HLA-B | 1 |
| Q9UNW1 | Multiple inositol polyphosphate phosphatase 1 | MINPP1 | 1 |
| Q6B0K9 | Hemoglobin subunit mu | HBM | 1 |
| O75915 | PRA1 family protein 3 | ARL6IP5 | 1 |
| O95376 | E3 ubiquitin-protein ligase ARIH2 | ARIH2 | 1 |
| E9PBW4 | Hemoglobin subunit gamma-2 | HBG2 | 1 |
| C9J1X0 | WD repeat-containing protein 91 | WDR91 | 1 |
| Q8NCV1 | | | 1 |
| Q9Y4P8 | WD repeat domain phosphoinositide-interacting protein 2 | WIPI2 | 1 |
| A0A087WUX6 | Proteasomal ubiquitin receptor ADRM1 | ADRM1 | 1 |
| Q9NQS7 | Inner centromere protein | INCENP | 1 |
| P62805 | Histone H4 | HIST1H4A | 1 |
| Q8TDY2 | RB1-inducible coiled-coil protein 1 | RB1CC1 | 1 |
| C9JFM5 | Syntaxin-4 | STX4 | 1 |
| B0QZ43 | Erlin-2; Erlin-1 | ERLIN1; ERLIN2 | 1 |
| C9J8T0 | Selenocysteine-specific elongation factor | EEFSEC | 1 |
| P61224 | Ras-related protein Rap-1b; Ras-related protein Rap-1b-like protein | RAP1B | 1 |
| Q99828 | Calcium and integrin-binding protein 1 | CIB1 | 1 |
| Q53GQ0 | Very-long-chain 3-oxoacyl-CoA reductase | HSD17B12 | 1 |
| H0Y9Q9 | ADP-ribosyl cyclase/cyclic ADP-ribose hydrolase 2 | BST1 | 1 |
| R4GN98 | Protein S100; Protein S100-A6 | S100A6 | 1 |
| Q8TB73 | Protein NDNF | NDNF | 1 |
| Q6P1A2 | Lysophospholipid acyltransferase 5 | LPCAT3 | 1 |
| F2Z2Y4 | Pyridoxal kinase | PDXK | 1 |
| Q9HA65 | TBC1 domain family member 17 | TBC1D17 | 1 |
| G3V126 | V-type proton ATPase subunit H | ATP6V1H | 1 |
| D6RGE2 | Isochorismatase domain-containing protein 1 | ISOC1 | 1 |
| A0A0B4J222 | ADP-ribosylation factor-like protein 15 | ARL15 | 1 |
| F8W7W4 | Androglobin | ADGB | 1 |
| Q9GZR7 | | | 1 |
| A0A087WVC4 | cAMP-dependent protein kinase catalytic subunit beta | PRKACB | 1 |
| A8MU39 | Serine/threonine-protein phosphatase; Serine/threonine-protein phosphatase 5 | PPP5C | 1 |
| G3V1N2 | | HBA2 | 1 |
| P69892 | Hemoglobin subunit gamma-2 | HBG2 | 1 |
| F8WEZ0 | 1-phosphatidylinositol 3-phosphate 5-kinase | PIKFYVE | 1 |
| A0A087WZZ4 | Ammonium transporter Rh type A | RHAG | 1 |
| Q1JUQ3 | Peptidyl-prolyl cis-trans isomerase; Peptidyl-prolyl cis-trans isomerase FKBP1A | FKBP12-Exin; FKBP1A | 1 |
| F8VWZ5 | H2.0-like homeobox protein | HLX | 1 |
| P62877 | E3 ubiquitin-protein ligase RBX1; E3 ubiquitin-protein ligase RBX1, N-terminally processed | RBX1 | 1 |
| Q7Z5P9 | Mucin-19 | MUC19 | 1 |
| F8VPB3 | | TPK1 | 1 |
| F8WBF4 | Transmembrane protein 50B | TMEM50B | 1 |
| C9JL85 | Myotrophin | MTPN | 1 |
| Q53EQ6 | Tigger transposable element-derived protein 5 | TIGD5 | 1 |
| E3W974 | | DNPEP | 1 |
| H7BYV1 | Interferon-induced transmembrane protein 1; Interferon-induced transmembrane protein 2; Interferon-induced transmembrane protein 3 | IFITM2; IFITM3; IFITM1 | 1 |
| D6RC06 | Histidine triad nucleotide-binding protein 1 | HINT1 | 1 |
| E9PNW4 | CD59 glycoprotein | CD59 | 1 |
| H7C2Z6 | Grancalcin | GCA | 1 |
| Q9H1C7 | Cysteine-rich and transmembrane domain-containing protein 1 | CYSTM1 | 1 |
| H0YK07 | ATP-dependent Clp protease ATP-binding subunit clpX-like, mitochondrial | CLPX | 1 |
| E9PG15 | 14-3-3 protein theta | YWHAQ | 1 |
| K7ENK9 | Vesicle-associated membrane protein 3; Vesicle-associated membrane protein 2 | VAMP2; VAMP3 | 1 |
| F8WDD6 | Cation channel sperm-associated protein subunit gamma | CATSPERG | 1 |
| P35754 | Glutaredoxin-1 | GLRX | 1 |
| Q5THJ4 | Vacuolar protein sorting-associated protein 13D | VPS13D | 1 |
| B4E3H6 | Transforming acidic coiled-coil-containing protein 1 | TACC1 | 1 |
| B0YJC4 | Vimentin | VIM | 1 |
| H7C5R6 | AT-rich interactive domain-containing protein 4B | ARID4B | 1 |

TABLE 4-continued

Proteins identified in the EEV proteome. Lists of the proteins identified by LC-MS/MS analysis using Andromeda ™/MaxQuant ™ search engine in the Uniprot Complete Proteome *Homo sapiens* database for the non-hemoglobin-depleted sample (356 proteins) (A), or when the hemoglobin-depleted and hemoglobin-containing fractions were analyzed separately (818 proteins) (B). The lists were filtered at 1% False Discovery Rate using a target/decoy database search.

| Protein ID | Protein names | Gene names | Razor + unique peptides |
| --- | --- | --- | --- |
| P49755 | Transmembrane emp24 domain-containing protein 10 | TMED10 | 1 |
| E9PMJ3 | Ribonuclease inhibitor | RNH1 | 1 |
| B1AHA9 | DNA replication licensing factor MCM5 | MCM5 | 1 |
| P23634 | Plasma membrane calcium-transporting ATPase 4 | ATP2B4 | 1 |
| Q14152 | Eukaryotic translation initiation factor 3 subunit A | EIF3A | 1 |
| C9IY70 | 60S ribosomal export protein NMD3 | NMD3 | 1 |
| A0A087WUS7 | Ig delta chain C region | IGHD | 1 |
| P07384 | Calpain-1 catalytic subunit | CAPN1 | 1 |
| G3V2C9 | Guanine nucleotide-binding protein subunit gamma; Guanine nucleotide-binding protein G(I)/G(S)/G(O) subunit gamma-2 | GNG2 | 1 |
| Q9Y2Y8 | Proteoglycan 3 | PRG3 | 1 |
| V9GY70 |  | DNAJB12 | 1 |
| U5GXS0 | MAM and LDL-receptor class A domain-containing protein 1 | MALRD1 | 1 |
| Q92625 | Ankyrin repeat and SAM domain-containing protein 1A | ANKS1A | 1 |

The present description refers to a number of documents, the contents of which are herein incorporated by reference in their entirety.

REFERENCES

Cox et al., *Nat Biotechnol* (2008); 26(12):1367-72.
Havlis et al., *Anal Chem* (2003); 75(6):1300-6.
Lacroix et al, *Journal of Thrombosis and Haemostasis* (2012), 10:437-446.
Lotvall et al., *J Extracell Vesicles* (2014), 3:26913.
Maere et al., *Bioinformatics* (2005); 21(16):3448-9.
Martinez-Martin et al., *Parkinsonism & related disorders* (2015). 21(1):50-4.
Minetti et al., *Biochem J* (2004); 377(Pt 2):489-97.
Prudent et al., *Transfus Apher Sci*. (2015). 53(2):153-8.
R Core Team (2016). R: A language and environment for statistical computing. R Foundation for Statistical Computing, Vienna, Austria. URL https://www.R-project.org/.
Rousseau et al., *PLoS One* (2015), 10(1):e0116812.
Shevchenko et al., *Anal Chem* (1996); 68(5):850-8.
Suzuki et al., *Bioinformatics* (2006); 22(12):1540-2.
Wither et al., Mass Spectrometry-Based Bottom-Up Proteomics: Sample Preparation, LC-MS/MS Analysis, and Database Query Strategies. *Curr Protoc Protein Sci* (2016); 86:16.4.1-16.4.20.

What is claimed is:

1. An in vitro method for preparing a clinical human blood sample, the method comprising
    (a) obtaining a preparation of isolated erythrocyte-derived extracellular vesicles (EEV) from a blood sample of a subject having or suspected of having Parkinson's disease;
    (b) removing hemoglobin from the preparation of isolated EEV, thereby obtaining a processed blood sample depleted of hemoglobin; and
    (c) quantifying the expression levels of one or more proteins in the processed blood sample of (b).

2. The method of claim 1, wherein the quantification in (c) is performed on EEVs having a diameter of between 100 nm and 1000 nm.

3. The method of claim 1, wherein the EEV are CD235a+ extracellular vesicles.

4. The method of claim 1, wherein the EEV are TSG101+, Rabs+, CD9+, CD63+, CD81+, or any combination thereof.

5. The method of claim 1, wherein said blood sample is platelet-free plasma.

6. The method of claim 1, further comprising, prior to (a), inducing calcium-dependent production of EEV from activated erythrocytes in the blood sample of the subject using a calcium ionophore, cold-storage, or ATP-depletion.

7. The method of claim 1, wherein the preparation of isolated EEV is obtained by separating the EEV by flow cytometry, differential centrifugation, nanomembrane ultrafiltration, immunoabsorbent capture, size-exclusion chromatography, ultracentrifugation, magnetic activated cell sorting (MACS), nanoparticle tracking analysis, light scattering, electrophoretic light scattering, dynamic light scattering, electron microscopy, or any combination thereof.

8. The method of claim 1, wherein the quantification in (c) comprises mass spectrometry.

9. The method of claim 1, wherein the quantification in (c) comprises nano liquid chromatography tandem mass spectrometry (nanoLC MS/MS).

10. An in vitro method for preparing a clinical human blood sample, the method comprising
    (a) obtaining a preparation of isolated erythrocyte-derived extracellular vesicles (EEV) depleted of hemoglobin from a blood sample of a subject having or suspected of having Parkinson's disease; and
    (b) quantifying the expression levels of one or more proteins biomarkers, in the preparation of isolated EEV depleted of hemoglobin.

* * * * *

UNITED STATES PATENT AND TRADEMARK OFFICE
CERTIFICATE OF CORRECTION

PATENT NO. : 12,411,147 B2
APPLICATION NO. : 18/306992
DATED : September 9, 2025
INVENTOR(S) : Francesca Cicchetti and Eric Boilard It is certified that error appears in the above-identified patent and that said Letters Patent is hereby corrected as shown below:

In the Claims

In Claim 10, Column 76, Line 58, delete "proteins biomarkers, in" and insert -- proteins in --.

Signed and Sealed this
Ninth Day of December, 2025

John A. Squires
*Director of the United States Patent and Trademark Office*